US011021710B2

(12) United States Patent
Bui

(10) Patent No.: US 11,021,710 B2
(45) Date of Patent: Jun. 1, 2021

(54) COMPOUNDS AND METHODS FOR REDUCING FXI EXPRESSION

(71) Applicant: Ionis Pharmaceuticals, Inc., Carlsbad, CA (US)

(72) Inventor: Huynh-Hoa Bui, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/091,891

(22) Filed: Nov. 6, 2020

(65) Prior Publication Data

US 2021/0087569 A1 Mar. 25, 2021

Related U.S. Application Data

(63) Continuation of application No. PCT/US2019/031277, filed on May 8, 2019.

(60) Provisional application No. 62/699,572, filed on Jul. 17, 2018, provisional application No. 62/669,280, filed on May 9, 2018.

(51) Int. Cl.
*C12N 15/113* (2010.01)

(52) U.S. Cl.
CPC ...... *C12N 15/1137* (2013.01); *C12N 2310/14* (2013.01); *C12N 2310/315* (2013.01)

(58) Field of Classification Search
None
See application file for complete search history.

(56) References Cited

U.S. PATENT DOCUMENTS 3,687,808 A 8/1972 Merigan et al.
4,415,732 A 11/1983 Caruthers et al.
4,469,863 A 9/1984 Ts'o et al.
4,476,301 A 10/1984 Imbach et al.
4,500,707 A 2/1985 Caruthers et al.
4,725,677 A 2/1988 Koster et al.
4,845,205 A 7/1989 Huynh Dinh et al.
4,973,679 A 11/1990 Caruthers et al.
4,981,957 A 1/1991 Lebleu et al.
5,013,830 A 5/1991 Ohutsuka et al.
5,023,243 A 6/1991 Tullis
5,034,506 A 7/1991 Summerton et al.
5,118,800 A 6/1992 Smith et al.
5,130,302 A 7/1992 Spielvogel et al.
5,132,418 A 7/1992 Caruthers et al.
5,134,066 A 7/1992 Rogers et al.
RE34,036 E 8/1992 McGeehan
5,149,797 A 9/1992 Pederson et al.
5,166,315 A 11/1992 Summerton et al.
5,175,273 A 12/1992 Bischofberger et al.
5,177,196 A 1/1993 Meyer, Jr. et al.
5,177,198 A 1/1993 Spielvogel et al.
5,188,897 A 2/1993 Suhadolnik et al.
5,194,599 A 3/1993 Froehler et al.
5,214,134 A 5/1993 Weis et al.
5,216,141 A 6/1993 Benner
5,220,007 A 6/1993 Pederson et al.
5,223,618 A 6/1993 Cook et al.
5,235,033 A 8/1993 Summerton et al.
5,252,217 A 10/1993 Burnouf-Radosevich
5,256,775 A 10/1993 Froehler
5,264,423 A 11/1993 Cohen et al.
5,264,562 A 11/1993 Matteucci
5,264,564 A 11/1993 Matteucci
5,185,444 A 12/1993 Summerton et al.
5,276,019 A 1/1994 Cohen et al.
5,286,717 A 2/1994 Cohen et al.
5,319,080 A 6/1994 Leumann
5,321,131 A 6/1994 Agrawal et al.
5,359,044 A 10/1994 Cook et al.
5,366,878 A 11/1994 Pederson et al.
5,367,066 A 11/1994 Urdea et al.
5,378,825 A 1/1995 Cook et al.
5,386,023 A 1/1995 Sanghvi et al.

(Continued)

FOREIGN PATENT DOCUMENTS

EP 2222707 9/2010
WO WO 2016/105516 6/1916

(Continued)

OTHER PUBLICATIONS

Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(Continued)

*Primary Examiner* — Tracy Vivlemore

(74) *Attorney, Agent, or Firm* — Knobbe, Martens, Olson & Bear, LLP

(57) ABSTRACT

Provided are compounds, methods, and pharmaceutical compositions for reducing the amount or activity of FXI RNA in a cell or subject, and in certain instances reducing the amount of FXI protein in a cell or subject. Such compounds, methods, and pharmaceutical compositions are useful to prevent, treat, or ameliorate at least one symptom of a thromboembolic condition without a significant increase in a bleeding risk. Such thromboembolic conditions include deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. Such symptoms include decreased blood flow through an affected vessel, death of tissue, and death.

18 Claims, 6 Drawing Sheets

Specification includes a Sequence Listing.

(56) References Cited

U.S. PATENT DOCUMENTS 5,393,878 A 2/1995 Leumann
5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Buie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,801,154 A 9/1998 Baracchini et al.
5,808,027 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'o
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,566,140 B2 5/2003 Mann et al.
6,582,908 B2 6/2003 Fodor et al.
6,600,032 B1 7/2003 Manoharan et al.
6,660,720 B2 12/2003 Manoharan
6,770,748 B2 8/2004 Imanishi et al.
7,015,315 B1 3/2006 Cook et al.
7,053,207 B2 5/2006 Wengel et al.
7,101,993 B1 9/2006 Cook et al.
7,176,303 B2 2/2007 Freier et al.
7,217,572 B2 5/2007 Ward et al.
7,262,177 B2 8/2007 Ts'o et al.
7,399,845 B2 7/2008 Seth et al.
7,427,672 B2 9/2008 Imanishi et al.
7,491,805 B2 2/2009 Vargeese et al.
7,521,213 B2 4/2009 Hantash
7,547,684 B2 6/2009 Seth et al.
7,569,686 B1 8/2009 Bhat et al.
7,666,854 B2 2/2010 Seth et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,888,497 B2 2/2011 Bentwich et al.
7,939,677 B2 5/2011 Bhat et al.
8,022,193 B2 9/2011 Swayze et al.
8,030,467 B2 10/2011 Seth et al.
8,071,291 B2 12/2011 Bare et al.
8,080,644 B2 12/2011 Wengel et al.
8,088,746 B2 1/2012 Seth et al.
8,088,904 B2 1/2012 Swayze et al.
8,090,542 B2 1/2012 Khvorova et al.
8,106,022 B2 1/2012 Manoharan et al.
8,124,745 B2 2/2012 Allerson et al.
8,143,230 B2 3/2012 Bhanot et al.
8,153,365 B2 4/2012 Wengel et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,334,372 B2 12/2012 Freier et al.
8,440,803 B2 5/2013 Swayze et al.
8,481,701 B2 7/2013 Prado et al.
8,501,805 B2 8/2013 Seth et al.
8,530,640 B2 9/2013 Seth et al.
8,546,556 B2 10/2013 Seth et al.
RE44,779 E 2/2014 Imanishi et al.
8,828,956 B2 9/2014 Manoharan et al.
9,005,906 B2 4/2015 Swayze et al.
9,012,421 B2 4/2015 Migawa et al.
9,127,276 B2 8/2015 Prakash et al.
9,290,760 B2 3/2016 Rajeev et al.
2001/0053519 A1 12/2001 Fodor et al.
2003/0158403 A1 8/2003 Manoharan et al.
2003/0175906 A1 9/2003 Manoharan et al.
2003/0228597 A1 12/2003 Cowsert et al.
2004/0171570 A1 9/2004 Allerson et al.
2004/0180855 A1 9/2004 Schumacher et al.
2005/0130923 A1 6/2005 Bhat et al.
2005/0181978 A1 8/2005 Rojkjaer et al.
2006/0063730 A1 3/2006 Monia et al.
2006/0134663 A1 6/2006 Harkin et al.
2006/0148740 A1 7/2006 Platenburg

(56) References Cited

U.S. PATENT DOCUMENTS

2007/0031844 A1 2/2007 Khvorova et al.
2007/0083334 A1 4/2007 Mintz et al.
2008/0015162 A1 1/2008 Bhanot et al.
2008/0039618 A1 2/2008 Allerson et al.
2008/0058266 A1 3/2008 Rojkjaer et al.
2008/0131876 A1 6/2008 Hantash
2008/0146788 A1 6/2008 Bhat et al.
2008/0219998 A1 9/2008 Gruber
2010/0190837 A1 7/2010 Migawa et al.
2010/0197762 A1 8/2010 Swayze et al.
2011/0172107 A1 7/2011 Katz et al.
2013/0130378 A1 5/2013 Manoharan et al.
2013/0171144 A1 7/2013 Gruber et al.
2013/0274308 A1 10/2013 Freier et al.
2014/0107330 A1 4/2014 Freier et al.
2015/0018540 A1 1/2015 Prakash et al.
2015/0184153 A1 7/2015 Freier et al.
2015/0191727 A1 7/2015 Migawa et al.
2015/0267195 A1 9/2015 Seth et al.
2015/0275212 A1 10/2015 Albaek et al.
2017/0145424 A1 5/2017 Prakash et al.

FOREIGN PATENT DOCUMENTS

WO WO 2019/182037 9/1919
WO WO 1995/017420 6/1995
WO WO 2000/056885 9/2000
WO WO 02/072882 9/2002
WO WO 03/004602 1/2003
WO WO 2005/116204 12/2004
WO WO 2005/106042 11/2005
WO WO 2006/034348 3/2006
WO WO 2007/027894 3/2007
WO WO 2007/146511 12/2007
WO WO 2008/066776 6/2008
WO WO 2010/045509 4/2010
WO WO 2010/121074 10/2010
WO WO 2013/070771 5/2013
WO WO 2014/179620 11/2014
WO WO-2015179693 A1 * 11/2015 ........... C12N 15/113
WO WO 2015/188194 12/2015

OTHER PUBLICATIONS

Crooke et al., RNA-Targeted Therapeutics: Cell Metabolism (2018) 27(4):714-739.
Crooke, St., et al., "Antisense Drug Technology" Second Edition, CRC Press (2008) Chapters 1-28.
Crosby et al., "Antisense Oligonucleotide Mediated Depletion of Factor XI Results in Effective Anticoagulation with a Favorable Risk/Benefit Profile in Mice" Arteriosclerosis Thrombosis and Vascular Biology (2009) 29(7):E21; Abstract.
Davis et al., "Improved targeting of miRNA with antisense oligonucleotides" Nucleic Acids Research (2006) 34(8):2294-2304.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Fujikawa et al., NCBI publication of GenBank M13142.1 (1994).
Gailani, "Gene targeting in hemostasis: factor XI" Front. Biosci. (2001) 6:D201-D207.
Gailani et al., "The intrinsic pathway of coagulation: a target for treating thromboembolic disease" Journal of Thrombosis and Haemostasis (2007) 5(6):1106-1112.
Gaynor et al., "Synthesis, Properties and Application of Nucleic Acids Containing Phosphorothiolate Linkages" Current Organic Chemistry Epub (2008) 12(4):291-308.
GenBank Direct Submission AX609519, sequence 544 from Patent WO02072882, Feb. 17, 2003.
GenBank Submission AY402921, Feb. 3, 2006.
GenBank accession No. NM_000128.3.
GenBank accession No. FW775436.1.
Howard et al., "Factor Ixa Inhibitors as Novel Anticoagulants" Arterioscler Thromb Vascl Biol (2007) 27(4):722-727.
Kubitza et al., "Rivaroxaban (BAY 59/7939)—an oral, direct Factor Xa inhibitor—has no clinically relevant interaction with naproxen." Br. J. Clin. Pharmacol. (2006) 63(4):469-476.
Leumann, "DNA Analogues: From Supramolecular Principles to Biological Properties" Bioorganic & Medicinal Chemistry (2002) 10:841-854.
Lowenberg et al., "Coagulation factor XI as a novel target for antithrombotic treatment" Journal of Thrombosis and Haemostasis (2010) 8(11):2349-2357.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Schumacher et al., "Antithrombotic and hemostatic effects of a small molecule factor Xia inhibitor in rats" European Journal of Pharmacology (2007) 570(1-3):167-174.
Seth et al., "Short Antisense Oligonucleotides with Novell 2'-4' Conformationaly Restricted Nucleoside Analogues Show Improved Potency Without Increased Toxicity in Animals." J Med Chem (2009) 52:10-13.
Tucker et al. "Survival Advantage of Coagulation Factor XI-Deficient Mice during Peritoneal Sepsis" J. Infect Dis. (2008) 198(2): 271-274.
Wong et al., "Apixaban, an oral, direct and highly selective factor Xa inhibitor: in vitro, antithrombotic and antihemostatic studies" J. Thromb. Haemost. (2008) 6(5):820-829.
Wong et al., "Arterial antithrombotic and bleeding time effects of apixaban, a direct factor Xa inhibitor, in combination with antiplatelet therapy in rabbits" Journal of Thrombosis and Haemostasis (2008) 6(10):1736-1741.
Woolf et al., "Specificity of antisense oligonucleotides in vivo" PNAS (1992) 89:7305-7309.
Yamashita et al., "Factor XI contributes to thrombus propagation on injured neointima of the rabbit iliac artery" Journal of Thrombosis and Haemostasis (2006) 4(7):1496-1501.
Younis et al., "Antisense inhibition of coagulation factor XI prolongs APTT without increased bleeding risk in cynomolgus monkeys" Blood (2012) 119(10):2401-2408.
Zhang et al., "Inhibition of the intrinsic coagulation pathway factor XI by antisense oligonucleotides: a novel antithrombotic strategy with lowered bleeding risk" Blood (2010) 116(22):4684-4692.
European Search Report for application EP 09821293.9 dated May 9, 2012.
European Search Report for application Ep 17201814.5 dated Jul. 6, 2018.
International Search Report for application PCT/US09/060922 dated May 26, 2010.
International Search Report for application PCT/US19/31277 dated.

* cited by examiner

COMPOUNDS AND METHODS FOR REDUCING FXI EXPRESSION

SEQUENCE LISTING

The present application is being filed along with a Sequence Listing in electronic format. The Sequence Listing is provided as a file entitled BIOL0337USC1SEQ_ST25.txt, created on Nov. 6, 2020, which is 40 KB in size. The information in the electronic format of the sequence listing is incorporated herein by reference in its entirety.

FIELD

Provided herein are compounds, methods, and pharmaceutical compositions for reducing an amount of Factor XI (FXI) RNA in a cell or animal, and in certain instances reducing the amount of FXI protein in a cell or animal. Such compounds, methods, and pharmaceutical compositions are useful to treat or prevent a thromboembolic condition. In certain embodiments, the compounds, methods, and pharmaceutical compositions are useful to treat or prevent a thromboembolic condition without increasing bleeding risk. Such thromboembolic conditions include deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition.

BACKGROUND

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor Ha, or factor 2a). Thrombin activates platelets, converts fibrinogen to fibrin and promotes fibrin cross-linking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII to XIIa. Factor XIIa converts XI to XIa, and XIa converts IX to IXa. IXa associates with its cofactor Villa to convert X to Xa. The two pathways converge at this point as factor Xa associates with factor Va to activate prothrombin (factor II) to thrombin (factor Ha). Factor XI enhances both the formation and stability of clots in vitro, but is not thought to be involved in the initiation of clotting. Rather, Factor XI is important in the propagation phase of clot growth (von de Borne, et al., *Blood Coagulation and Fibrinolysis,* 2006, 17:251-257). Additionally, Factor XI-dependent amplification of thrombin formation leads to activation of TAFI (thrombin activatable fibrinolysis inhibitor), which renders clots less sensitive to fibrinolysis (Bouma et al, *J Thromb Haemost* 1999; 82: 1703-1708).

Inhibition of Coagulation.

At least three mechanisms keep the coagulation cascade in check, namely the action of activated protein C, antithrombin, and tissue factor pathway inhibitor. Activated protein C is a serine protease that degrades cofactors Va and Villa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., *Trends Cardiovasc Med.* 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. *American Journal of Clinical Pathology.* 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bertina R M et al. *Nature* 1994; 369:64-67.)

Treatment

The most commonly used anticoagulants, warfarin, heparin, low molecular weight heparin (LMWH), and newer direct oral anticoagulants (DOAC), all possess significant drawbacks.

Warfarin is typically used to treat patients suffering from atrial fibrillation. The drug interacts with vitamin K-dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) resulting in increased bleeding and requires patient monitoring. Prolonged treatment with heparin may also lead to osteoporosis. LMWH can also inhibit Factor II, but to a lesser degree than unfractioned heparin (UFH). LMWH has been implicated in the development of HIT.

Several direct oral anticoagulants have been FDA-approved for the treatment of thrombotic disease, including four Factor Xa inhibitors Betrixaban, Apixaban, Rivaroxaban, and Edoxaban and one direct thrombin inhibitor, Dabigatran. (Smith, M., *Surg Clin N Am* 2018 98:219-238). Rivaroxaban, Dabigatran, and Edoxaban all exhibit increased bleeding, especially increased GI bleeding risk compared to warfarin.

Currently there remains a need for therapies to treat thromboembolic conditions without risk of increased bleeding. It is therefore an object herein to provide compounds, methods, and pharmaceutical compositions for the treatment of such diseases.

BRIEF DESCRIPTION OF THE DRAWINGS

FIG. 1A shows levels of plasma FXI protein activity. FIG. 1B shows percent change in plasma FXI protein activity relative to baseline.

FIG. 2A shows concentrations of plasma FXI protein. FIG. 2B shows percent change in plasma FXI protein concentrations relative to baseline.

FIG. 3A shows levels of plasma FXI protein activity. FIG. 3B shows percent change in plasma FXI protein activity relative to baseline.

FIG. 4A shows concentrations of plasma FXI protein. FIG. 4B shows change in plasma FXI protein concentrations relative to baseline.

FIG. 5A shows levels of plasma FXI protein activity. FIG. 5B shows mean percent change in plasma FXI protein activity.

FIG. 6A shows plasma FXI protein concentrations. FIG. 6B shows percent change in plasma FXI protein concentrations.

SUMMARY OF THE INVENTION

Figure 1A:
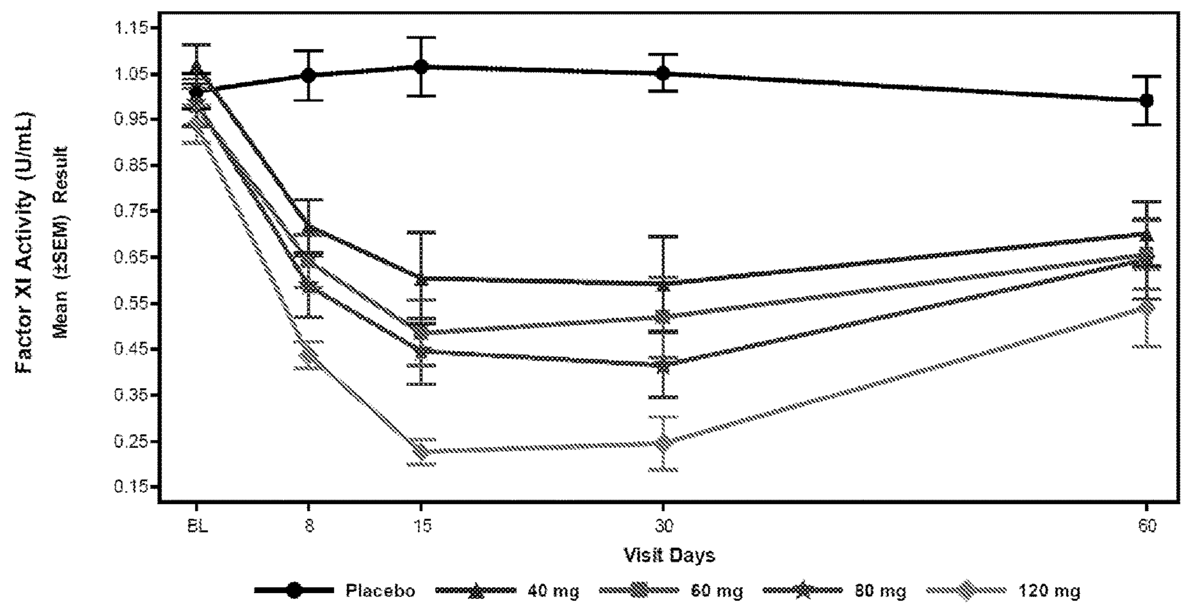
FIGS. 1A and 1B show pharmacodynamic results over time for single dose cohorts receiving Compound No. 957943, as measured by relative plasma FXI protein activity.

Provided herein are compounds, methods and pharmaceutical compositions for reducing an amount of FXI RNA, and in certain embodiments reducing the amount of FXI protein in a cell or animal. In certain embodiments, methods and pharmaceutical compositions disclosed herein reduce FXI protein activity in the blood of an animal. In certain embodiments, the animal has or is at risk for a thromboembolic condition. In certain embodiments, the animal has or is at risk for deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition.

In certain embodiments, compounds useful for reducing a FXI RNA are oligomeric compounds. In certain embodiments, compounds useful for reducing a FXI RNA are modified oligonucleotides. In certain embodiments, compounds useful for reducing a FXI RNA are oligomeric compounds comprising a conjugate group and a modified oligonucleotide. In certain embodiments, compounds useful for reducing a FXI RNA are oligomeric compounds consisting of a conjugate group and a modified oligonucleotide.

Also provided are methods useful for treating, preventing, or ameliorating a thromboembolic condition. In certain embodiments, the thromboembolic condition is deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition.

Also provided are methods useful treating, preventing, or ameliorating a thromboembolic condition without increasing bleeding risk in an individual. In certain embodiments, the individual is at risk for a thromboembolic condition, including, but not limited to infarct, thrombosis, embolism, thromboembolism such as deep vein thrombosis, pulmonary embolism, myocardial infarction, and stroke. Such diseases, disorders, and conditions can have one or more risk factors, causes, or outcomes in common. Certain risk factors and causes for development of a thromboembolic condition include immobility, surgery (particularly orthopedic surgery), dialysis, malignancy, pregnancy, older age, use of oral contraceptives, atrial fibrillation, previous thromboembolic condition, chronic inflammatory disease, inherited or acquired prothrombotic clotting disorders and thrombosis associated with chronic kidney disease or end-stage renal disease (ESRD). Certain outcomes associated with development of a thromboembolic condition include decreased blood flow through an affected vessel, death of tissue, and death.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, “2'-substituted nucleoside” means a nucleoside comprising a 2'-substituted sugar moiety. As used herein, “2'-substituted” in reference to a sugar moiety means a sugar moiety comprising at least one 2'-substituent group other than H or OH.

As used herein, “5-methyl cytosine” means a cytosine modified with a methyl group attached to the 5 position. A 5-methyl cytosine is a modified nucleobase.

As used herein, “about” means plus or minus 7% of the provided value.

As used herein, “administering” means providing a pharmaceutical agent to an animal.

As used herein, “animal” means a human or non-human animal. In certain embodiments, the animal is a human.

As used herein, “antisense activity” means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, “antisense compound” means an oligomeric compound capable of achieving at least one antisense activity.

As used herein, “cleavable moiety” means a bond or group of atoms that is cleaved under physiological conditions, for example, inside a cell or an animal.

As used herein, “complementary” in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, “fully complementary” or “100% complementary” in reference to oligonucleotides means that oligonucleotides are complementary to another oligonucleotide or nucleic acid at each nucleoside of the oligonucleotide.

As used herein, “conjugate group” means a group of atoms that is directly attached to an oligonucleotide. Conjugate groups include a conjugate moiety and a conjugate linker that attaches the conjugate moiety to the oligonucleotide.

As used herein, “conjugate linker” means a single bond or group of atoms comprising at least one bond that connects a conjugate moiety to an oligonucleotide. In certain embodiments, a conjugate linker comprises a cleavable moiety.

As used herein, “conjugate moiety” means a group of atoms that is attached to an oligonucleotide via a conjugate linker. In certain embodiments, a conjugate moiety comprises a cell-targeting moiety.

As used herein, “contiguous” in the context of an oligonucleotide refers to nucleosides, nucleobases, sugar moieties, or internucleoside linkages that are immediately adjacent to each other. For example, “contiguous nucleobases” means nucleobases that are immediately adjacent to each other in a sequence.

As used herein, “chirally enriched population” means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are oligomeric compounds disclosed herein. In certain embodiments, the oligomeric compounds are antisense compounds. In certain embodiments, the molecules are modified oligonucleotides. In certain embodiments, the molecules are oligomeric compounds comprising modified oligonucleotides.

As used herein, “dosage unit” means a formulation of an oligomeric compound, or pharmaceutical composition thereof, for administration, wherein the oligomeric compound is provided at a quantity of a single selected dose. The term dosage unit, as used herein, may comprise packaging or a container that contains the pharmaceutical composition, such as a vial or syringe. As used herein, “gapmer” means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the “gap” and the external regions may be referred to as the “wings.” Unless otherwise indicated, “gapmer” refers to a sugar motif. Unless otherwise indicated, the sugar moieties of the nucleosides of the gap of a gapmer are unmodified 2'-deoxyribosyl. Thus, the term “MOE gapmer” indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, “hybridization” means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, “identifying an animal at risk for developing a thromboembolic condition” means identifying an animal having been diagnosed with a thromboembolic condition or identifying an animal predisposed to develop a thromboembolic condition. Individuals predisposed to develop a thromboembolic condition include those having one or more risk factors for thromboembolic conditions including immobility, surgery (particularly orthopedic surgery), dialysis, malignancy, pregnancy, older age, use of oral contraceptives, inherited or acquired prothrombotic clotting disorders, chronic kidney disease, and end-stage renal disease (ESRD). Such identification may be accomplished by any method including evaluating an individual's medical history and standard clinical tests or assessments.

As used herein, the term “internucleoside linkage” is the covalent linkage between adjacent nucleosides in an oligonucleotide. As used herein “modified internucleoside linkage” means any internucleoside linkage other than a phosphodiester internucleoside linkage. “Phosphorothioate internucleoside linkage” is a modified internucleoside linkage in which one of the non-bridging oxygen atoms of a phosphodiester internucleoside linkage is replaced with a sulfur atom.

As used herein, the term "linker region" in reference to a conjugate moiety refers that part of a conjugate linker that is not a cleavable moiety.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-$OCH_2CH_2OCH_3$ group in place of the 2'-OH group of a ribosyl sugar moiety.

As used herein, "2'-MOE nucleoside" means a nucleoside comprising a 2'-MOE modified sugar.

As used herein, "monthly" means every 28 to 31 days.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), and guanine (G).

As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by an animal. In certain embodiments, a pharmaceutically acceptable carrier or diluent is sterile water, distilled water for injection, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to an animal. For example, a pharmaceutical composition may comprise an oligomeric compound and a sterile aqueous solution. In certain embodiments, a pharmaceutical composition shows activity in free uptake assay in certain cell lines.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "stereorandom chiral center" in the context of a population of molecules of identical molecular formula means a chiral center having a random stereochemical configuration. For example, in a population of molecules comprising a stereorandom chiral center, the number of molecules having the (5) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "thromboembolic condition" means any disease or condition involving an embolism caused by a thrombus. Examples of such diseases=and conditions include the categories of thrombosis, embolism, and thromboembolism. In certain embodiments, such diseases and conditions include deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. Thromboembolic conditions may also be referred to as thromboembolic events or thrombotic events.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "therapeutically effective amount" means an amount of a pharmaceutical agent that provides a therapeutic benefit to an animal. For example, a therapeutically effective amount of a pharmaceutical agent treats, prevents, or ameliorates a thromboembolic condition.

As used herein, "weekly" means every six to eight days.

Certain Embodiments

The present disclosure provides the following non-limiting numbered embodiments:

Embodiment 1. An oligomeric compound according to the following formula:

(SEQ ID NO: 3)

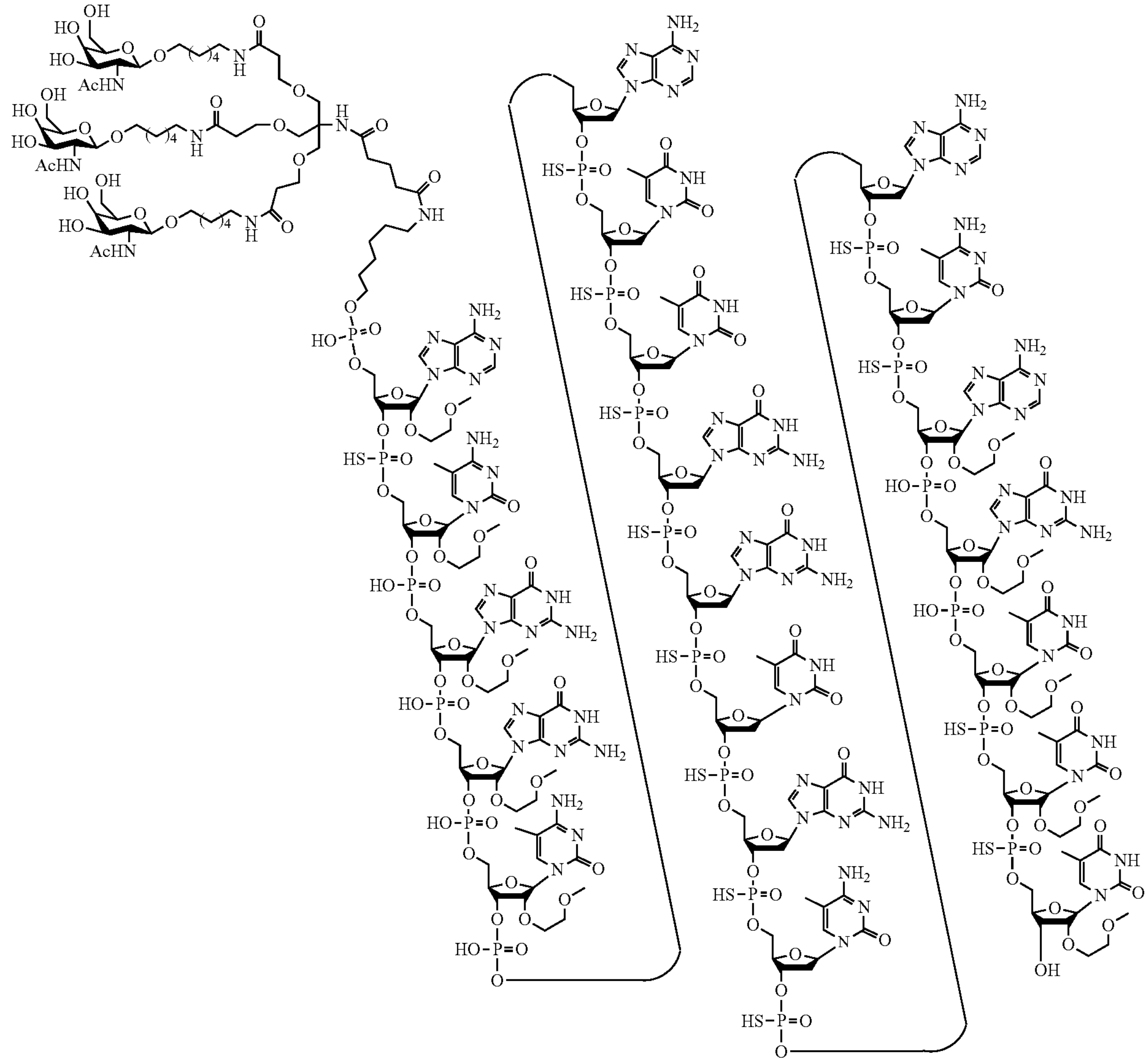

or a salt thereof.

Embodiment 2. An oligomeric compound according to the following formula:
(SEQ ID NO: 3)
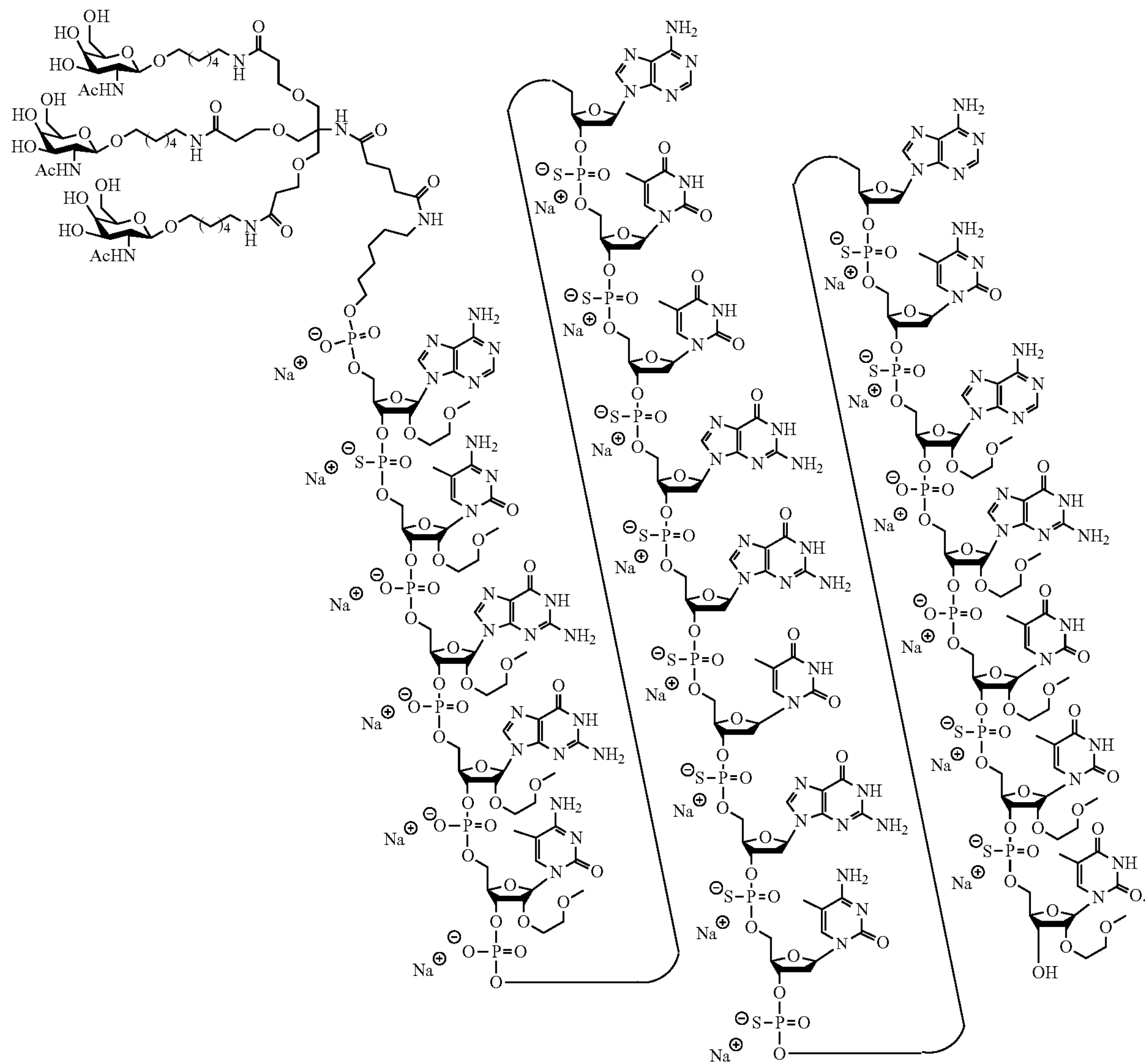

Embodiment 3. An oligomeric compound comprising a modified oligonucleotide according to the following formula:
(SEQ ID NO: 3)
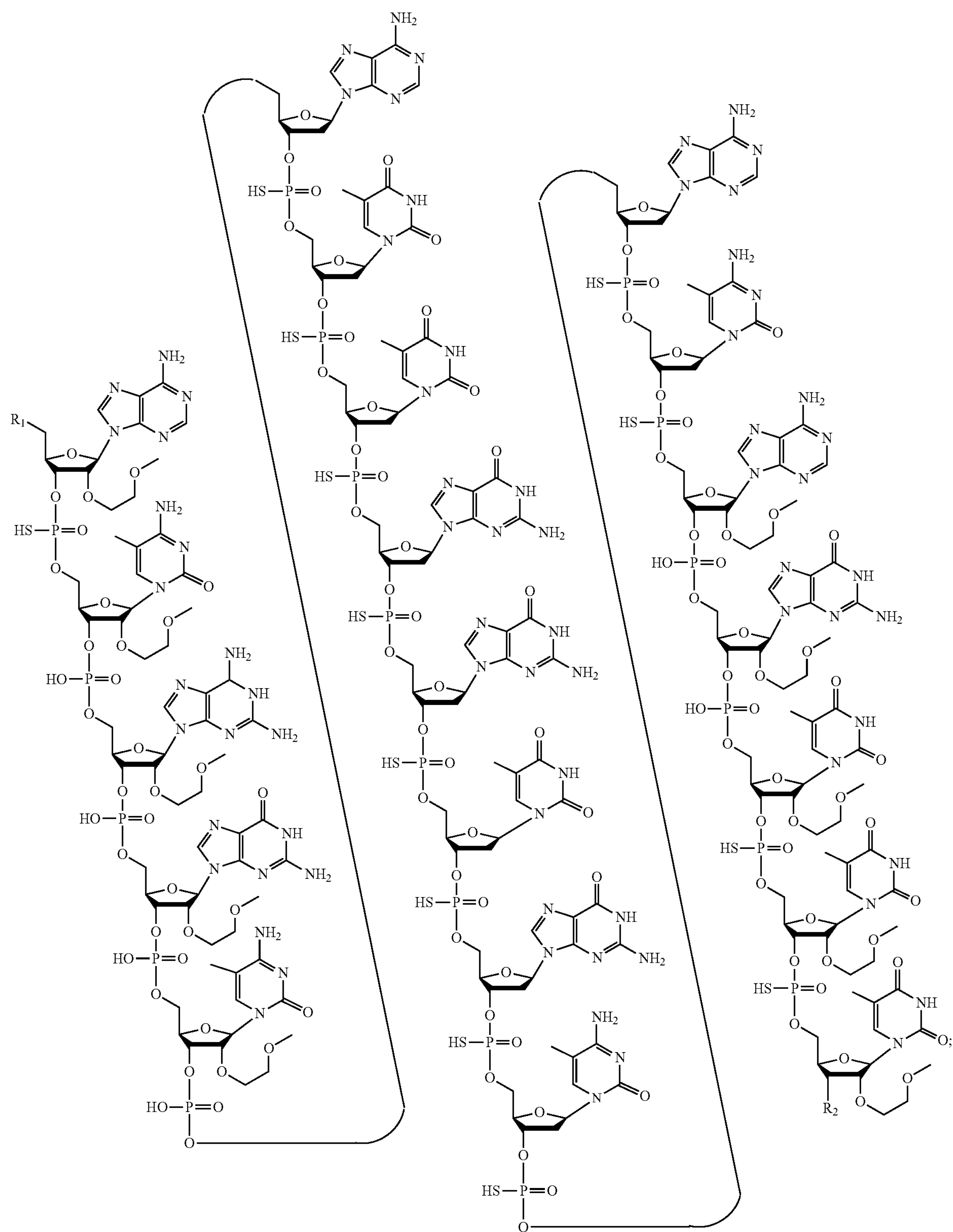

wherein one of $R_1$ or $R_2$ is a conjugate group comprising at least one, two, or three GalNAc ligands, and the other of $R_1$ or $R_2$ is —OH;

or a salt thereof.

Embodiment 4. An oligomeric compound comprising a modified oligonucleotide according to the following formula:

(THA-GalNAc$_3$)o Aes mCeo Geo Geo mCeo Ads Tds Tds Gds Gds Tds Gds mCds Ads mCds Aeo Geo Tes Tes Te (SEQ ID NO: 3); wherein, (THA-GalNAc3)o is represented by the following structure:

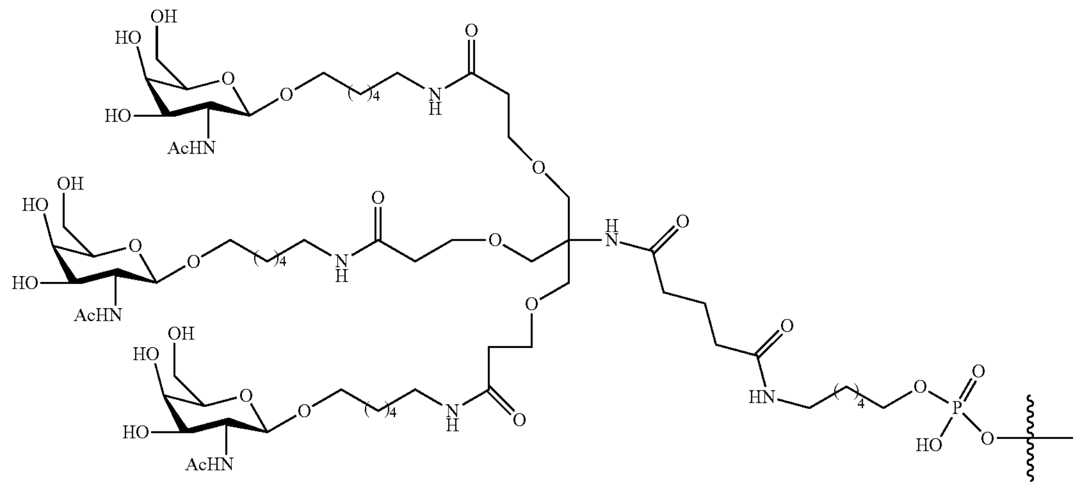

and wherein,

A=an adenine nucleobase, mC=a 5'-methyl cytosine nucleobase,

G=a guanine nucleobase,

T=a thymine nucleobase, e=a 2'-MOE modified sugar, d=a 2'-deoxyribose sugar, s=a phosphorothioate internucleoside linkage, and o=a phosphodiester internucleoside linkage;

or a salt thereof.

Embodiment 5. The oligomeric compound of any one of embodiments 1, 3 or 5, which is a sodium salt.

Embodiment 6. A chirally enriched population of the oligomeric compound of any of embodiments 1-5 wherein the population is enriched for oligomeric compounds having a modified oligonucleotide comprising at least one particular phosphorothioate internucleoside linkage having a particular stereochemical configuration.

Embodiment 7. The chirally enriched population of embodiment 6, wherein the population is enriched for oligomeric compounds having a modified oligonucleotide comprising at least one particular phosphorothioate internucleoside linkage having the (Sp) configuration.

Embodiment 8. The chirally enriched population of embodiment 6 or 7, wherein the population is enriched for oligomeric compounds having a modified oligonucleotides comprising at least one particular phosphorothioate internucleoside linkage having the (Rp) configuration.

Embodiment 9. The chirally enriched population of embodiment 6, wherein the population is enriched for oligomeric compounds having a modified oligonucleotide having a particular, independently selected stereochemical configuration at each phosphorothioate internucleoside linkage.

Embodiment 10. The chirally enriched population of embodiment 9, wherein the population is enriched for oligomeric compounds having a modified oligonucleotide having the (Sp) configuration at each phosphorothioate internucleoside linkage.

Embodiment 11. The chirally enriched population of embodiment 9, wherein the population is enriched for oligomeric compounds having a modified oligonucleotide having the (Rp) configuration at each phosphorothioate internucleoside linkage.

Embodiment 12. The chirally enriched population of embodiment 6 or 9 wherein the population is enriched for oligomeric compounds having a modified oligonucleotide having at least 3 contiguous phosphorothioate internucleoside linkages in the Sp-Sp-Rp configurations, in the 5' to 3' direction.

Embodiment 13. A population of oligomeric compounds having a modified oligonucleotide of any of embodiments 1-5, wherein all of the phosphorothioate internucleoside linkages of the modified oligonucleotide are stereorandom.

Embodiment 14. A pharmaceutical composition comprising the oligomeric compound of any one of embodiments 1-5, the chirally enriched population of any one of embodiments 6-12, or the population of embodiment 13, and a pharmaceutically acceptable carrier or diluent.

Embodiment 15. The pharmaceutical composition of embodiment 14, wherein the pharmaceutically acceptable diluent is phosphate buffered saline.

Embodiment 16. The pharmaceutical composition of embodiment 14, wherein the pharmaceutical composition consists or consists essentially of the oligomeric compound and phosphate buffered saline.

Embodiment 17. The pharmaceutical composition of any one of embodiments 14-16, wherein the concentration of the oligomeric compound in the pharmaceutically acceptable carrier or diluent is selected from:

a) 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml;

b) about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml; and c) 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml, 61 mg/ml, 62 mg/ml, 63 mg/ml, 64 mg/ml, 65 mg/ml, 66 mg/ml, 67 mg/ml, 68 mg/ml, 69 mg/ml, 70 mg/ml, 71 mg/ml, 72 mg/ml, 73 mg/ml, 74 mg/ml, 75 mg/ml, 76 mg/ml, 77 mg/ml, 78 mg/ml, 79 mg/ml, 80 mg/ml, 81 mg/ml, 82 mg/ml, 83 mg/ml, 84 mg/ml, 85 mg/ml, 86 mg/ml, 87 mg/ml, 88 mg/ml, 89 mg/ml, 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, 101 mg/ml, 102 mg/ml, 103 mg/ml, 104 mg/ml, 105 mg/ml, 106 mg/ml, 107 mg/ml, 108 mg/ml, 109 mg/ml, 110 mg/ml, 111 mg/ml, 112 mg/ml, 113 mg/ml, 114 mg/ml, 115 mg/ml, 116 mg/ml, 117 mg/ml, 118 mg/ml, 119 mg/ml, 120 mg/ml, 121 mg/ml, 122 mg/ml, 123 mg/ml, 124 mg/ml, 125 mg/ml, 126 mg/ml, 127 mg/ml, 128 mg/ml, 129 mg/ml, 130 mg/ml, 131 mg/ml, 132 mg/ml, 133 mg/ml, 134 mg/ml, 135 mg/ml, 136 mg/ml, 137 mg/ml, 138 mg/ml, 139 mg/ml, 140 mg/ml;

d) about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 61 mg/ml, about 62 mg/ml, about 63 mg/ml, about 64 mg/ml, about 65 mg/ml, about 66 mg/ml, about 67 mg/ml, about 68 mg/ml, about 69 mg/ml, about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 133 mg/ml, about 134 mg/ml, about 135 mg/ml, about 136 mg/ml, about 137 mg/ml, about 138 mg/ml, about 139 mg/ml, and about 140 mg/ml.

Embodiment 18. The pharmaceutical composition of any one of embodiments 14-16, wherein the concentration of the oligomeric compound in the pharmaceutically acceptable carrier or diluent is selected from 20 mg/ml to 180 mg/ml, 20 mg/ml to 170 mg, 20 mg/ml to 160 mg/ml, 20 mg/ml to 150 mg/ml, 20 mg/ml to 140 mg/ml, 20 mg/ml to 130 mg/ml, 20 mg/ml to 120 mg/ml, 20 mg/ml to 110 mg/ml, 20 mg/ml to 100 mg/ml, 20 mg/ml to 90 mg/ml, 20 mg/ml to 80 mg/ml, 20 mg/ml to 70 mg/ml, 20 mg/ml to 60 mg/ml, 20 mg/ml to 50 mg/ml, 20 mg/ml to 40 mg/ml, 20 mg/ml to 30 mg/ml, 30 mg/ml to 180 mg/ml, 30 mg/ml to 170 mg, 30 mg/ml to 160 mg/ml, 30 mg/ml to 150 mg/ml, 30 mg/ml to 140 mg/ml, 30 mg/ml to 130 mg/ml, 30 mg/ml to 120 mg/ml, 30 mg/ml to 110 mg/ml, 30 mg/ml to 100 mg/ml, 30 mg/ml to 90 mg/ml, 30 mg/ml to 80 mg/ml, 30 mg/ml to 70 mg/ml, 30 mg/ml to 60 mg/ml, 30 mg/ml to 50 mg/ml, 30 mg/ml to 40 mg/ml, 40 mg/ml to 180 mg/ml, 40 mg/ml to 170 mg, 40 mg/ml to 160 mg/ml, 40 mg/ml to 150 mg/ml, 40 mg/ml to 140 mg/ml, 40 mg/ml to 130 mg/ml, 40 mg/ml to 120 mg/ml, 40 mg/ml to 110 mg/ml, 40 mg/ml to 100 mg/ml, 40 mg/ml to 90 mg/ml, 40 mg/ml to 80 mg/ml, 40 mg/ml to 70 mg/ml, 40 mg/ml to 60 mg/ml, 40 mg/ml to 50 mg/ml, 50 mg/ml to 180 mg/ml, 50 mg/ml to 170 mg, 50 mg/ml to 160 mg/ml, 50 mg/ml to 150 mg/ml, 50 mg/ml to 140 mg/ml, 50 mg/ml to 130 mg/ml, 50 mg/ml to 120 mg/ml, 50 mg/ml to 110 mg/ml, 50 mg/ml to 100 mg/ml, 50 mg/ml to 90 mg/ml, 50 mg/ml to 80 mg/ml, 50 mg/ml to 70 mg/ml, 50 mg/ml to 60 mg/ml, 60 mg/ml to 180 mg/ml, 60 mg/ml to 170 mg, 60 mg/ml to 160 mg/ml, 60 mg/ml to 150 mg/ml, 60 mg/ml to 140 mg/ml, 60 mg/ml to 130 mg/ml, 60 mg/ml to 120 mg/ml, 60 mg/ml to 110 mg/ml, 60 mg/ml to 100 mg/ml, 60 mg/ml to 90 mg/ml, 60 mg/ml to 80 mg/ml, 60 mg/ml to 70 mg/ml, 70 mg/ml to 180 mg/ml, 70 mg/ml to 170 mg, 70 mg/ml to 160 mg/ml, 70 mg/ml to 150 mg/ml, 70 mg/ml to 140 mg/ml, 70 mg/ml to 130 mg/ml, 70 mg/ml to 120 mg/ml, 70 mg/ml to 110 mg/ml, 70 mg/ml to 100 mg/ml, 70 mg/ml to 90 mg/ml, 70 mg/ml to 80 mg/ml, 80 mg/ml to 180 mg/ml, 80 mg/ml to 170 mg, 80 mg/ml to 160 mg/ml, 80 mg/ml to 150 mg/ml, 80 mg/ml to 140 mg/ml, 80 mg/ml to 130 mg/ml, 80 mg/ml to 120 mg/ml, 80 mg/ml to 110 mg/ml, 80 mg/ml to 100 mg/ml, 80 mg/ml to 90 mg/ml, 90 mg/ml to 180 mg/ml, 90 mg/ml to 170 mg, 90 mg/ml to 160 mg/ml, 90 mg/ml to 150 mg/ml, 90 mg/ml to 140 mg/ml, 90 mg/ml to 130 mg/ml, 90 mg/ml to 120 mg/ml, 90 mg/ml to 110 mg/ml, 90 mg/ml to 100 mg/ml, 100 mg/ml to 180 mg/ml, 100 mg/ml to 170 mg, 100 mg/ml to 160 mg/ml, 100 mg/ml to 150 mg/ml, 100 mg/ml to 140 mg/ml, 100 mg/ml to 130 mg/ml, 100 mg/ml to 120 mg/ml, 100 mg/ml to 110 mg/ml, 110 mg/ml to 180 mg/ml, 110 mg/ml to 170 mg, 110 mg/ml to 160 mg/ml, 110 mg/ml to 150 mg/ml, 110 mg/ml to 140 mg/ml, 110 mg/ml to 130 mg/ml, 110 mg/ml to 120 mg/ml, 120 mg/ml to 180 mg/ml, 120 mg/ml to 170 mg, 120 mg/ml to 160 mg/ml, 120 mg/ml to 150 mg/ml, 120 mg/ml to 140 mg/ml, 120 mg/ml to 130 mg/ml, 130 mg/ml to 180 mg/ml, 130 mg/ml to 170 mg, 130 mg/ml to 160 mg/ml, 130 mg/ml to 150 mg/ml, 130 mg/ml to 140 mg/ml, 140 mg/ml to 180 mg/ml, 140 mg/ml to 170 mg/ml, 140 mg/ml to 160 mg/ml, 140 mg/ml to 150 mg/ml, 150 mg/ml to 180 mg/ml, 150 mg/ml to 170 mg/ml, 150 mg/ml to 160 mg/ml, 160 mg/ml to 180 mg/ml, 160 mg/ml to 170 mg/ml, and 170 mg/ml to 180 mg/ml.

Embodiment 19. The pharmaceutical composition of any one of embodiments 14-18, wherein the pharmaceutical composition is in a form of a dosage unit.

Embodiment 20. The pharmaceutical composition of embodiment 19, wherein the oligomeric compound is present in the dosage unit at an amount selected from:

a) 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg;

b) about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg;

c) 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg;

d) about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 128 mg, about 129 mg, about 130 mg, about 131 mg, about 132 mg, about 133 mg, about 134 mg, about 135 mg, about 136 mg, about 137 mg, about 138 mg, about 139 mg, about 140 mg;

e) 75.0 mg, 75.1 mg, 75.2 mg, 75.3 mg, 75.4 mg, 75.5 mg, 75.6 mg, 75.7 mg, 75.8 mg, 75.9 mg, 76.0 mg, 76.1 mg, 76.2 mg, 76.3 mg. 76.4 mg, 76.5 mg, 76.6 mg, 76.7 mg, 76.8 mg, 76.9 mg, 77.0 mg, 77.1 mg, 77.2 mg, 77.3 mg, 77.4 mg, 77.5 mg, 77.6 mg, 77.7 mg, 77.8 mg, 77.9 mg, 78.0 mg, 78.1 mg, 78.2 mg, 78.3 mg. 78.4 mg, 78.5 mg, 78.6 mg, 78.7 mg, 78.8 mg, 78.9 mg, 79.0 mg, 79.1 mg, 79.2 mg, 79.3 mg, 79.4 mg, 79.5 mg, 79.6 mg, 79.7 mg, 79.8 mg, 79.9 mg, 80.0 mg, 80.1 mg, 80.2 mg, 80.3 mg. 80.4 mg, 80.5 mg, 80.6 mg, 80.7 mg, 80.8 mg, 80.9 mg, 81.0 mg, 81.1 mg, 81.2 mg, 81.3 mg, 81.4 mg, 81.5 mg, 81.6 mg, 81.7 mg, 81.8 mg, 81.9 mg, 82.0 mg, 82.1 mg, 82.2 mg, 82.3 mg. 82.4 mg, 82.5 mg, 82.6 mg, 82.7 mg, 82.8 mg, 82.9 mg, 83.0 mg, 83.1 mg, 83.2 mg, 83.3 mg, 83.4 mg, 83.5 mg, 83.6 mg, 83.7 mg, 83.8 mg, 83.9 mg, 84.0 mg, 84.1 mg, 84.2 mg, 84.3 mg. 84.4 mg, 84.5 mg, 84.6 mg, 84.7 mg, 84.8 mg, 84.9 mg, 85.0 mg; and f) about 75.0 mg, about 75.1 mg, about 75.2 mg, about 75.3 mg, about 75.4 mg, about 75.5 mg, about 75.6 mg, about 75.7 mg, about 75.8 mg, about 75.9 mg, about 76.0 mg, about 76.1 mg, about 76.2 mg, about 76.3 mg. about 76.4 mg, about 76.5 mg, about 76.6 mg, about 76.6 about 76.7 mg, about 76.8 mg, about 76.9 mg, about 77.0 mg, about 77.1 mg, about 77.2 mg, about 77.3 mg, about 77.4 mg, about 77.5 mg, about 77.6 mg, about 77.7 mg, about 77.8 mg, about 77.9 mg, about 78.0 mg, about 78.1 mg, about 78.2 mg, about 78.3 mg. about 78.4 mg, about 78.5 mg, about 78.6 mg, about 78.7 mg, about 78.8 mg, about 78.9 mg, about 79.0 mg, about 79.1 mg, about 79.2 mg, about 79.3 mg, about 79.4 mg, about 79.5 mg, about 79.6 mg, about 79.7 mg, about 79.8 mg, about 79.9 mg, about 80.0 mg, about 80.1 mg, about 80.2 mg, about 80.3 mg. about 80.4 mg, about 80.5 mg, about 80.6 mg, about 80.7 mg, about 80.8 mg, about 80.9 mg, about 81.0 mg, about 81.1 mg, about 81.2 mg, about 81.3 mg, about 81.4 mg, about 81.5 mg, about 81.6 mg, about 81.7 mg, about 81.8 mg, about 81.9 mg, about 82.0 mg, about 82.1 mg, about 82.2 mg, about 82.3 mg. about 82.4 mg, about 82.5 mg, about 82.6 mg, about 82.7 mg, about 82.8 mg, about 82.9 mg, about 83.0 mg, about 83.1 mg, about 83.2 mg, about 83.3 mg, about 83.4 mg, about 83.5 mg, about 83.6 mg, about 83.7 mg, about 83.8 mg, about 83.9 mg, about 84.0 mg, about 84.1 mg, about 84.2 mg, about 84.3 mg. about 84.4 mg, about 84.5 mg, about 84.6 mg, about 84.7 mg, about 84.8 mg, about 84.9 mg, and about 85.0 mg.

Embodiment 21. The pharmaceutical composition of embodiment 17, wherein the oligomeric compound is present in the dosage unit at an amount selected from: less than about 300 mg, less than about 295 mg, less than about 290 mg, less than about 285 mg, less than about 280 mg, less than about 275 mg, less than about 270 mg, less than about 265 mg, less than about 260 mg, less than about 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, and less than about 20 mg.

Embodiment 22. The pharmaceutical composition of embodiment 19, wherein the oligomeric compound is present in the dosage unit at an amount selected from:

a) 10 mg to 140 mg, from 10 mg to 130 mg, from 10 mg to 120 mg, from 10 mg to 110 mg, from 10 mg to 100 mg, from 10 mg to 90 mg, from 10 mg to 80 mg, from 10 mg to 70 mg, from 10 mg to 60 mg, from 10 mg to 50 mg, from 10 mg to 40 mg, from 10 mg to 30 mg, from 10 mg to 20 mg, from 20 mg to 140 mg, from 20 mg to 130 mg, from 20 mg to 120 mg, from 20 mg to 110 mg, from 20 mg to 100 mg, from 20 mg to 90 mg, from 20 mg to 80 mg, from 20 mg to 70 mg, from 20 mg to 60 mg, from 20 mg to 50 mg, from 20 mg to 40 mg, from 20 mg to 30 mg, from 30 mg to 140 mg, from 30 mg to 130 mg, from 30 mg to 120 mg, from 30 mg to 110 mg, from 30 mg to 100 mg, from 30 mg to 90 mg, from 30 mg to 80 mg, from 30 mg to 70 mg, from 30 mg to 60 mg, from 30 mg to 50 mg, from 30 mg to 40 mg, from 40 mg to 140 mg, from 40 mg to 130 mg, from 40 mg to 120 mg, from 40 mg to 110 mg, from 40 mg to 100 mg, from 40 mg to 90 mg, from 40 mg to 80 mg, from 40 mg to 70 mg, from 40 mg to 60 mg, from 40 mg to 50 mg, from 50 mg to 140 mg, from 50 mg to 130 mg, from 50 mg to 120 mg, from 50 mg to 110 mg, from 50 mg to 100 mg, from 50 mg to 90 mg, from 50 mg to 80 mg, from 50 mg to 70 mg, from 50 mg to 60 mg, from 60 mg to 140 mg, from 60 mg to 130 mg, from 60 mg to 120 mg, from 60 mg to 110 mg, from 60 mg to 100 mg, from 60 mg to 90 mg, from 60 mg to 80 mg, from 60 mg to 70 mg, from 70 mg to 140 mg, from 70 mg to 130 mg, from 70 mg to 120 mg, from 70 mg to 110 mg, from 70 mg to 100 mg, from 70 mg to 90 mg, from 70 mg to 80 mg, from 80 mg to 140 mg, from 80 mg to 130 mg, from 80 mg to 120 mg, from 80 mg to 110 mg, from 80 mg to 100 mg, from 80 mg to 90 mg, from 90 mg to 140 mg, from 90 mg to 130 mg, from 90 mg to 120 mg, from 90 mg to 110 mg, from 90 mg to 100 mg, from 100 mg to 140 mg, from 100 mg to 130 mg, from 100 mg to 120 mg, from 100 mg to 110 mg, from 110 mg to 140 mg, from 110 mg to 130 mg, from 110 mg to 120 mg, from 120 mg to 140 mg, from 120 mg to 130 mg, from 130 mg to 140 mg, from 65 mg to 95 mg, from 65 mg to 90 mg, from 65 mg to 85 mg from 65 mg to 80 mg, from 65 mg to 75 mg, from 65 mg to 70 mg, from 70 mg to 95 mg, from 70 mg to 85 mg, from 70 mg to 75 mg, from 75 mg to 100 mg, from 75 mg to 95 mg, from 75 mg to 90 mg, from 75 mg to 85 mg, from 75 mg to 80 mg, from 80 mg to 95 mg, from 80 mg to 85 mg, from 85 mg to 100 mg, from 85 mg to 90 mg, from 90 mg to 95 mg, from 95 mg to 100 mg, from 80 mg to 89 mg, from 80 mg to 88 mg, from 80 mg to 87 mg, from 80 mg to 86 mg, from 80 mg to 84 mg, from 80 mg to 83 mg, from 80 mg to 82 mg, from 80 mg to 81 mg, from 81 mg to 90 mg, from 82 mg to 89 mg, from 82 mg to 88 mg, from 82 mg to 87 mg, from 82 mg to 86 mg, from 82 mg to 85 mg, from 82 mg to 84 mg, from 82 mg to 83 mg, from 83 mg to 90 mg, from 83 mg to 89 mg, from 83 mg to 88 mg, from 83 mg to 87 mg, from 83 mg to 86 mg, from 83 mg to 85 mg, from 83 mg to 84 mg, from 84 mg to 90 mg, from 84 mg to 89 mg, from 84 mg to 88 mg, from 84 mg to 87 mg, from 84 mg to 86 mg, from 84 mg to 85 mg, from 85 mg to 89 mg, from 85 mg to 88 mg, from 85 mg to 87 mg, from 85 mg to 86 mg, from 86 mg to 90 mg, from 86 mg to 89 mg, from 86 mg to 88 mg, from 86 mg to 87 mg, from 87 mg to 90 mg, from 87 mg to 89 mg, from 87 mg to 88 mg, from 88 mg to 90 mg, from 88 mg to 89 mg, from 89 mg to 90 mg; and b) less than about 300 mg, less than about 295 mg, less than about 290 mg, less than about 285 mg, less than about 280 mg, less than about 275 mg, less than 270 mg, less than 265 mg, less than about 260 mg, less than 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, and less than about 20 mg.

Embodiment 23. The pharmaceutical composition of embodiment 19, wherein the oligomeric compound is present in the dosage unit at an amount selected from:

a) at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 115 mg, at least about 120 mg, at least about 125 mg, at least about 130 mg, at least about 135 mg, at least about 140 mg, at least about 145 mg, at least about 150 mg; and b) at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least about 100 mg, at least 105 mg, at least 115 mg, at least 120 mg, at least 125 mg, at least 130 mg, at least 135 mg, at least 140 mg, at least 145 mg, and at least 150 mg.

Embodiment 24. The pharmaceutical composition of any one of embodiments 19-23, wherein the dosage unit has a volume selected from:

a) 0.1 ml to 1.5 ml, 0.1 ml to 1.4 ml, 0.1 ml to 1.3 ml, 0.1 ml to 1.2 ml, 0.1 ml to 1.1 ml, 0.1 ml to 1.0 ml, 0.1 ml to 0.9 ml, 0.1 ml to 0.8 ml, 0.1 ml to 0.7 ml, 0.1 ml to 0.6 ml, 0.1 ml to 0.5 ml, 0.1 ml to 0.4 ml, 0.1 ml to 0.3 ml, 0.1 ml to 0.2 ml, 0.2 ml to 1.5 ml, 0.2 ml to 1.4 ml, 0.2 ml to 1.3 ml, 0.2 ml to 1.2 ml, 0.2 ml to 1.1 ml, 0.2 ml to 1.0 ml, 0.2 ml to 0.9 ml, 0.2 ml to 0.8 ml, 0.2 ml to 0.7 ml, 0.2 ml to 0.6 ml, 0.2 ml to 0.5 ml, 0.2 ml to 0.4 ml, 0.2 ml to 0.3 ml, 0.3 ml to 1.5 ml, 0.3 ml to 1.4 ml, 0.3 ml to 1.3 ml, 0.3 ml to 1.2 ml, 0.3 ml to 1.1 ml, 0.3 ml to 1.0 ml, 0.3 ml to 0.9 ml, 0.3 ml to 0.8 ml, 0.3 ml to 0.7 ml, 0.3 ml to 0.6 ml, 0.3 ml to 0.5 ml, 0.3 ml to 0.4 ml, 0.4 ml to 1.5 ml, 0.4 ml to 1.4 ml, 0.4 ml to 1.3 ml, 0.4 ml to 1.2 ml, 0.4 ml to 1.1 ml, 0.4 ml to 1.0 ml, 0.4 ml to 0.9 ml, 0.4 ml to 0.8 ml, 0.4 ml to 0.7 ml, 0.4 ml to 0.6 ml, 0.4 ml to 0.5 ml, 0.5 ml to 1.5 ml, 0.5 ml to 1.4 ml, 0.5 ml to 1.3 ml, 0.5. ml to 1.2 ml, 0.5 ml to 1.1 ml, 0.5 ml to 1.0 ml, 0.5 ml to 0.9 ml, 0.5 ml to 0.8 ml, 0.5 ml to 0.7 ml, 0.5 ml to 0.6 ml, 0.6 ml to 1.5 ml, 0.6 ml to 1.4 ml, 0.6 mo to 1.3 ml, 0.6 ml to 1.2 ml, 0.6 ml to 1.1 ml, 0.6 ml to 1.0 ml, 0.6 ml to 0.9 ml, 0.6 ml to 0.8 ml, 0.6 ml to 0.7 ml, 0.7 ml, to 1.5 ml, 0.7 ml to 1.4 ml, 0.7 ml to 1.3 ml, 0.7 ml to 1.2 ml, 0.7 ml to 1.1 ml, 0.7 ml to 1.0 ml, 0.7 ml to 0.9 ml, 0.7 ml to 0.8 ml, 0.8 ml to 1.5 ml, 0.8 ml to 1.4 ml, 0.8 ml to 1.3 ml, 0.8 ml to 1.2 ml, 0.8 ml to 1.1 ml, 0.8 ml to 1.0 ml. 0.8 ml to 0.9 ml, 0.9 ml, to 1.5 ml, 0.9 ml to 1.4 ml, 0.9 ml to 1.3 ml, 0.9 ml to 1.2 ml, 0.9 ml, to 1.1 ml, 0.9 ml to 1.0 ml, 1.0 ml to 1.5 ml, 1.0 ml to 1.4 ml, 1.0 ml to 1.3 ml, 1.0 ml to 1.2 ml, 1.0 ml to 1.1 ml, 1.1 ml to 1.5 ml, 1.1 ml to 1.4 ml, 1.1 ml to 1.3 ml, 1.1 ml to 1.2 ml, 1.2 ml to 1.5 ml, 1.2 ml to 1.4 ml, 1.2 ml to 1.3 ml, 1.3 ml to 1.5 ml, 1.3 ml to 1.4 ml, 1.4 ml to, 1.5 ml; and b) about 0.1 ml to about 1.5 ml, about 0.1 ml to about 1.4 ml, about 0.1 ml to about 1.3 ml, about 0.1 ml to about 1.2 ml, about 0.1 ml to about 1.1 ml, about 0.1 ml to about 1.0 ml, about 0.1 ml to about 0.9 ml, about 0.1 ml to about 0.8 ml, about 0.1 ml to about 0.7 ml, about 0.1 ml to about 0.6 ml, about 0.1 ml to about 0.5 ml, about 0.1 ml to about 0.4 ml, about 0.1 ml to about 0.3 ml, about 0.1 ml to about 0.2 ml, about 0.2 ml to about 1.5 ml, about 0.2 ml to about 1.4 ml, about 0.2 ml to about 1.3 ml, about 0.2 ml to about 1.2 ml, about 0.2 ml to about 1.1 ml, about 0.2 ml to about 1.0 ml, about 0.2 ml to about 0.9 ml, about 0.2 ml to about 0.8 ml, about 0.2 ml to about 0.7 ml, about 0.2 ml to about 0.6 ml, about 0.2 ml to about 0.5 ml, about 0.2 ml to about 0.4 ml, about 0.2 ml to about 0.3 ml, about 0.3 ml to about 1.5 ml, about 0.3 ml to about 1.4 ml, about 0.3 ml to about 1.3 ml, about 0.3 ml to about 1.2 ml, about 0.3 ml to about 1.1 ml, about 0.3 ml to about 1.0 ml, about 0.3 ml to about 0.9 ml, about 0.3 ml to about 0.8 ml, about 0.3 ml to about 0.7 ml, about 0.3 ml to about 0.6 ml, about 0.3 ml to about 0.5 ml, about 0.3 ml to about 0.4 ml, about 0.4 ml to about 1.5 ml, about 0.4 ml to about 1.4 ml, about 0.4 ml to about 1.3 ml, about 0.4 ml to about 1.2 ml, about 0.4 ml to about 1.1 ml, about 0.4 ml to about 1.0 ml, about 0.4 ml to about 0.9 ml, about 0.4 ml to about 0.8 ml, about 0.4 ml to about 0.7 ml, about 0.4 ml to about 0.6 ml, about 0.4 ml to about 0.5 ml, about 0.5 ml to about 1.5 ml, about 0.5 ml to about 1.4 ml, about 0.5 ml to about 1.3 ml, about 0.5. ml to about 1.2 ml, about 0.5 ml to about 1.1 ml, about 0.5 ml to about 1.0 ml, about 0.5 ml to about 0.9 ml, about 0.5 ml to about 0.8 ml, about 0.5 ml to about 0.7 ml, about 0.5 ml to about 0.6 ml, about 0.6 ml to about 1.5 ml, about 0.6 ml to about 1.4 ml, about 0.6 ml to about 1.3 ml, about 0.6 ml to about 1.2 ml, about 0.6 ml to about 1.1 ml, about 0.6 ml to about 1.0 ml, about 0.6 ml to about 0.9 ml, about 0.6 ml to about 0.8 ml, about 0.6 ml to about 0.7 ml, about 0.7 ml, about to about 1.5 ml, about 0.7 ml to about 1.4 ml, about 0.7 ml to about 1.3 ml, about 0.7 ml to about 1.2 ml, about 0.7 ml to about 1.1 ml, about 0.7 ml to about 1.0 ml, about 0.7 ml to about 0.9 ml, about 0.7 ml to about 0.8 ml, about 0.8 ml to about 1.5 ml, about 0.8 ml to about 1.4 ml, about 0.8 ml to about 1.3 ml, about 0.8 ml to about 1.2 ml, about 0.8 ml to about 1.1 ml, about 0.8 ml to about 1.0 ml. 0.8 ml to about 0.9 ml, about 0.9 ml, about to about 1.5 ml, about 0.9 ml to about 1.4 ml, about 0.9 ml to about 1.3 ml, about 0.9 ml to about 1.2 ml, about 0.9 ml, about to about 1.1 ml, about 0.9 ml to about 1.0 ml, about 1.0 ml to about 1.5 ml, about 1.0 ml to about 1.4 ml, about 1.0 ml to about 1.3 ml, about 1.0 ml to about 1.2 ml, about 1.0 ml to about 1.1 ml, about 1.1 ml to about 1.5 ml, about 1.1 ml to about 1.4 ml, about 1.1 ml to about 1.3 ml, about 1.1 ml to about 1.2 ml, about 1.2 ml to about 1.5 ml, about 1.2 ml to about 1.4 ml, about 1.2 ml to about 1.3 ml, about 1.3 ml to about 1.5 ml, about 1.3 ml to about 1.4 ml, and about 1.4 ml to about 1.5 ml.

Embodiment 25. The pharmaceutical composition of any one of embodiments 14-24, wherein the pharmaceutical composition is packaged in a pre-filled syringe.

Embodiment 26. A method comprising contacting a cell with the oligomeric compound of any of embodiments 1-5.

Embodiment 27. A method comprising administering to an animal a pharmaceutical composition comprising a therapeutically effective amount of an oligomeric compound according to the following formula:

Embodiment 31. The method of embodiment 30, wherein the therapeutically effective amount does not significantly alter platelet levels or platelet activity in the animal or does not cause bleeding in the animal compared to an animal not administered the pharmaceutical composition.

(SEQ ID NO: 3)

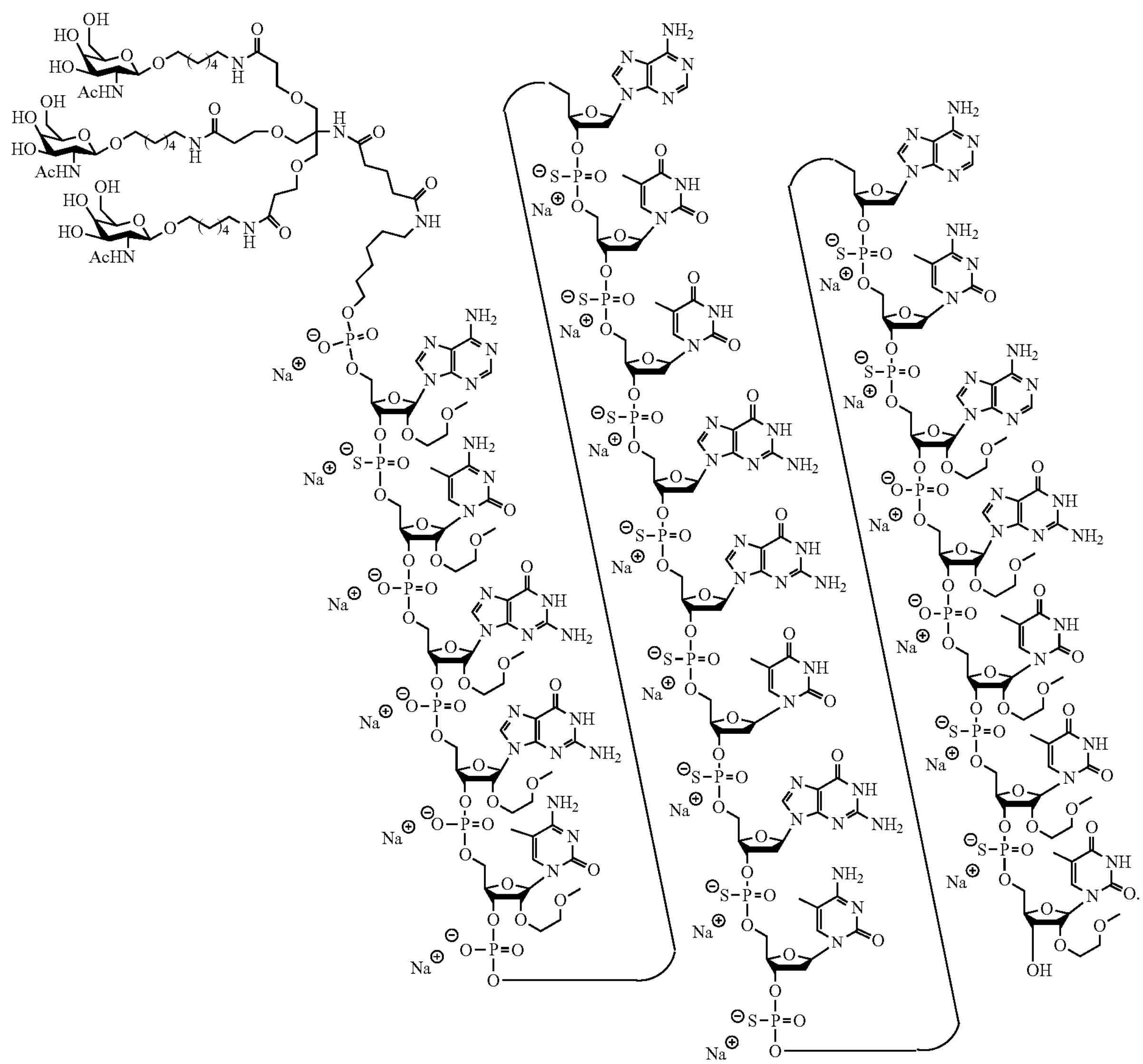

Embodiment 28. A method comprising administering to an animal a therapeutically effective amount of the oligomeric compound of any of embodiments 1-5 in the form of a pharmaceutical composition.

Embodiment 29. The method of embodiment 27 or 28, wherein the pharmaceutical composition consists or consists essentially of the oligomeric compound and phosphate buffered saline.

Embodiment 30. A method comprising administering to an animal the pharmaceutical compositions of any one of embodiments 14-25, wherein the pharmaceutical composition comprises a therapeutically effective amount of the oligomeric compound.

Embodiment 32. The method of any one of embodiments 27 to 31, comprising administering an amount of the oligomeric compound selected from:

a) 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg;

b) about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg;

c) 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg;

d) about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 128 mg, about 129 mg, about 130 mg, about 131 mg, about 132 mg, about 133 mg, about 134 mg, about 135 mg, about 136 mg, about 137 mg, about 138 mg, about 139 mg, about 140 mg;

e) 75.0 mg, 75.1 mg, 75.2 mg, 75.3 mg, 75.4 mg, 75.5 mg, 75.6 mg, 75.7 mg, 75.8 mg, 75.9 mg, 76.0 mg, 76.1 mg, 76.2 mg, 76.3 mg. 76.4 mg, 76.5 mg, 76.6 mg, 76.7 mg, 76.8 mg, 76.9 mg, 77.0 mg, 77.1 mg, 77.2 mg, 77.3 mg, 77.4 mg, 77.5 mg, 77.6 mg, 77.7 mg, 77.8 mg, 77.9 mg, 78.0 mg, 78.1 mg, 78.2 mg, 78.3 mg. 78.4 mg, 78.5 mg, 78.6 mg, 78.7 mg, 78.8 mg, 78.9 mg, 79.0 mg, 79.1 mg, 79.2 mg, 79.3 mg, 79.4 mg, 79.5 mg, 79.6 mg, 79.7 mg, 79.8 mg, 79.9 mg, 80.0 mg, 80.1 mg, 80.2 mg, 80.3 mg. 80.4 mg, 80.5 mg, 80.6 mg, 80.7 mg, 80.8 mg, 80.9 mg, 81.0 mg, 81.1 mg, 81.2 mg, 81.3 mg, 81.4 mg, 81.5 mg, 81.6 mg, 81.7 mg, 81.8 mg, 81.9 mg, 82.0 mg, 82.1 mg, 82.2 mg, 82.3 mg. 82.4 mg, 82.5 mg, 82.6 mg, 82.7 mg, 82.8 mg, 82.9 mg, 83.0 mg, 83.1 mg, 83.2 mg, 83.3 mg, 83.4 mg, 83.5 mg, 83.6 mg, 83.7 mg, 83.8 mg, 83.9 mg, 84.0 mg, 84.1 mg, 84.2 mg, 84.3 mg. 84.4 mg, 84.5 mg, 84.6 mg, 84.7 mg, 84.8 mg, 84.9 mg, 85.0 mg; and f) about 75.0 mg, about 75.1 mg, about 75.2 mg, about 75.3 mg, about 75.4 mg, about 75.5 mg, about 75.6 mg, about 75.7 mg, about 75.8 mg, about 75.9 mg, about 76.0 mg, about 76.1 mg, about 76.2 mg, about 76.3 mg. about 76.4 mg, about 76.5 mg, about 76.6 mg, about 76.6 about 76.7 mg, about 76.8 mg, about 76.9 mg, about 77.0 mg, about 77.1 mg, about 77.2 mg, about 77.3 mg, about 77.4 mg, about 77.5 mg, about 77.6 mg, about 77.7 mg, about 77.8 mg, about 77.9 mg, about 78.0 mg, about 78.1 mg, about 78.2 mg, about 78.3 mg. about 78.4 mg, about 78.5 mg, about 78.6 mg, about 78.7 mg, about 78.8 mg, about 78.9 mg, about 79.0 mg, about 79.1 mg, about 79.2 mg, about 79.3 mg, about 79.4 mg, about 79.5 mg, about 79.6 mg, about 79.7 mg, about 79.8 mg, about 79.9 mg, about 80.0 mg, about 80.1 mg, about 80.2 mg, about 80.3 mg. about 80.4 mg, about 80.5 mg, about 80.6 mg, about 80.7 mg, about 80.8 mg, about 80.9 mg, about 81.0 mg, about 81.1 mg, about 81.2 mg, about 81.3 mg, about 81.4 mg, about 81.5 mg, about 81.6 mg, about 81.7 mg, about 81.8 mg, about 81.9 mg, about 82.0 mg, about 82.1 mg, about 82.2 mg, about 82.3 mg. about 82.4 mg, about 82.5 mg, about 82.6 mg, about 82.7 mg, about 82.8 mg, about 82.9 mg, about 83.0 mg, about 83.1 mg, about 83.2 mg, about 83.3 mg, about 83.4 mg, about 83.5 mg, about 83.6 mg, about 83.7 mg, about 83.8 mg, about 83.9 mg, about 84.0 mg, about 84.1 mg, about 84.2 mg, about 84.3 mg. about 84.4 mg, about 84.5 mg, about 84.6 mg, about 84.7 mg, about 84.8 mg, about 84.9 mg, and about 85.0 mg.

Embodiment 33. The method of any one of embodiments 27 to 31, comprising administering an amount of the oligomeric compound selected from: less than about 300 mg, less than about 295 mg, less than about 290 mg, less than about 285 mg, less than about 280 mg, less than about 275 mg, less than about 270 mg, less than about 265 mg, less than about 260 mg, less than about 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, and less than about 20 mg.

Embodiment 34. The method of any one of embodiments 27 to 31, comprising administering an amount of the oligomeric compound selected from:

a) 10 mg to 140 mg, from 10 mg to 130 mg, from 10 mg to 120 mg, from 10 mg to 110 mg, from 10 mg to 100 mg, from 10 mg to 90 mg, from 10 mg to 80 mg, from 10 mg to 70 mg, from 10 mg to 60 mg, from 10 mg to 50 mg, from 10 mg to 40 mg, from 10 mg to 30 mg, from 10 mg to 20 mg, from 20 mg to 140 mg, from 20 mg to 130 mg, from 20 mg to 120 mg, from 20 mg to 110 mg, from 20 mg to 100 mg, from 20 mg to 90 mg, from 20 mg to 80 mg, from 20 mg to 70 mg, from 20 mg to 60 mg, from 20 mg to 50 mg, from 20 mg to 40 mg, from 20 mg to 30 mg, from 30 mg to 140 mg, from 30 mg to 130 mg, from 30 mg to 120 mg, from 30 mg to 110 mg, from 30 mg to 100 mg, from 30 mg to 90 mg, from 30 mg to 80 mg, from 30 mg to 70 mg, from 30 mg to 60 mg, from 30 mg to 50 mg, from 30 mg to 40 mg, from 40 mg to 140 mg, from 40 mg to 130 mg, from 40 mg to 120 mg, from 40 mg to 110 mg, from 40 mg to 100 mg, from 40 mg to 90 mg, from 40 mg to 80 mg, from 40 mg to 70 mg, from 40 mg to 60 mg, from 40 mg to 50 mg, from 50 mg to 140 mg, from 50 mg to 130 mg, from 50 mg to 120 mg, from 50 mg to 110 mg, from 50 mg to 100 mg, from 50 mg to 90 mg, from 50 mg to 80 mg, from 50 mg to 70 mg, from 50 mg to 60 mg, from 60 mg to 140 mg, from 60 mg to 130 mg, from 60 mg to 120 mg, from 60 mg to 110 mg, from 60 mg to 100 mg, from 60 mg to 90 mg, from 60 mg to 80 mg, from 60 mg to 70 mg, from 70 mg to 140 mg, from 70 mg to 130 mg, from 70 mg to 120 mg, from 70 mg to 110 mg, from 70 mg to 100 mg, from 70 mg to 90 mg, from 70 mg to 80 mg, from 80 mg to 140 mg, from 80 mg to 130 mg, from 80 mg to 120 mg, from 80 mg to 110 mg, from 80 mg to 100 mg, from 80 mg to 90 mg, from 90 mg to 140 mg, from 90 mg to 130 mg, from 90 mg to 120 mg, from 90 mg to 110 mg, from 90 mg to 100 mg, from 100 mg to 140 mg, from 100 mg to 130 mg, from 100 mg to 120 mg, from 100 mg to 110 mg, from 110 mg to 140 mg, from 110 mg to 130 mg, from 110 mg to 120 mg, from 120 mg to 140 mg, from 120 mg to 130 mg, from 130 mg to 140 mg, from 65 mg to 95 mg, from 65 mg to 90 mg, from 65 mg to 85 mg from 65 mg to 80 mg, from 65 mg to 75 mg, from 65 mg to 70 mg, from 70 mg to 95 mg, from 70 mg to 85 mg, from 70 mg to 75 mg, from 75 mg to 100 mg, from 75 mg to 95 mg, from 75 mg to 90 mg, from 75 mg to 85 mg, from 75 mg to 80 mg, from 80 mg to 95 mg, from 80 mg to 85 mg, from 85 mg to 100 mg, from 85 mg to 90 mg, from 90 mg to 95 mg, from 95 mg to 100 mg, from 80 mg to 89 mg, from 80 mg to 88 mg, from 80 mg to 87 mg, from 80 mg to 86 mg, from 80 mg to 84 mg, from 80 mg to 83 mg, from 80 mg to 82 mg, from 80 mg to 81 mg, from 81 mg to 90 mg, from 82 mg to 89 mg, from 82 mg to 88 mg, from 82 mg to 87 mg, from 82 mg to 86 mg, from 82 mg to 85 mg, from 82 mg to 84 mg, from 82 mg to 83 mg, from 83 mg to 90 mg, from 83 mg to 89 mg, from 83 mg to 88 mg, from 83 mg to 87 mg, from 83 mg to 86 mg, from 83 mg to 85 mg, from 83 mg to 84 mg, from 84 mg to 90 mg, from 84 mg to 89 mg, from 84 mg to 88 mg, from 84 mg to 87 mg, from 84 mg to 86 mg, from 84 mg to 85 mg, from 85 mg to 89 mg, from 85 mg to 88 mg, from 85 mg to 87 mg, from 85 mg to 86 mg, from 86 mg to 90 mg, from 86 mg to 89 mg, from 86 mg to 88 mg, from 86 mg to 87 mg, from 87 mg to 90 mg, from 87 mg to 89 mg, from 87 mg to 88 mg, from 88 mg to 90 mg, from 88 mg to 89 mg, from 89 mg to 90 mg; and b) less than about 300 mg, less than about 295 mg, less than about 290 mg, less than about 285 mg, less than about 280 mg, less than about 275 mg, less than 270 mg, less than 265 mg, less than about 260 mg, less than 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, and less than about 20 mg.

Embodiment 35. The method of any one of embodiments 27 to 31, comprising administering an amount of the oligomeric compound selected from:

a) at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 115 mg, at least about 120 mg, at least about 125 mg, at least about 130 mg, at least about 135 mg, at least about 140 mg, at least about 145 mg, at least about 150 mg; and b) at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least about 100 mg, at least 105 mg, at least 115 mg, at least 120 mg, at least 125 mg, at least 130 mg, at least 135 mg, at least 140 mg, at least 145 mg, and at least 150 mg.

Embodiment 36. The method of any one of embodiments 27 to 35, wherein the concentration of the oligomeric compound in the pharmaceutically acceptable carrier or diluent is selected from:

a) 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml;

b) about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, about 160 mg/ml; and c) 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml, 61 mg/ml, 62 mg/ml, 63 mg/ml, 64 mg/ml, 65 mg/ml, 66 mg/ml, 67 mg/ml, 68 mg/ml, 69 mg/ml, 70 mg/ml, 71 mg/ml, 72 mg/ml, 73 mg/ml, 74 mg/ml, 75 mg/ml, 76 mg/ml, 77 mg/ml, 78 mg/ml, 79 mg/ml, 80 mg/ml, 81 mg/ml, 82 mg/ml, 83 mg/ml, 84 mg/ml, 85 mg/ml, 86 mg/ml, 87 mg/ml, 88 mg/ml, 89 mg/ml, 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, 101 mg/ml, 102 mg/ml, 103 mg/ml, 104 mg/ml, 105 mg/ml, 106 mg/ml, 107 mg/ml, 108 mg/ml, 109 mg/ml, 110 mg/ml, 111 mg/ml, 112 mg/ml, 113 mg/ml, 114 mg/ml, 115 mg/ml, 116 mg/ml, 117 mg/ml, 118 mg/ml, 119 mg/ml, 120 mg/ml, 121 mg/ml, 122 mg/ml, 123 mg/ml, 124 mg/ml, 125 mg/ml, 126 mg/ml, 127 mg/ml, 128 mg/ml, 129 mg/ml, 130 mg/ml, 131 mg/ml, 132 mg/ml, 133 mg/ml, 134 mg/ml, 135 mg/ml, 136 mg/ml, 137 mg/ml, 138 mg/ml, 139 mg/ml, 140 mg/ml;

d) about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 61 mg/ml, about 62 mg/ml, about 63 mg/ml, about 64 mg/ml, about 65 mg/ml, about 66 mg/ml, about 67 mg/ml, about 68 mg/ml, about 69 mg/ml, about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 133 mg/ml, about 134 mg/ml, about 135 mg/ml, about 136 mg/ml, about 137 mg/ml, about 138 mg/ml, about 139 mg/ml, and about 140 mg/ml.

Embodiment 37. The method of any one of embodiments 27 to 35, wherein the concentration of the oligomeric compound in the pharmaceutically acceptable carrier or diluent is selected from: 20 mg/ml to 180 mg/ml, 20 mg/ml to 170 mg, 20 mg/ml to 160 mg/ml, 20 mg/ml to 150 mg/ml, 20 mg/ml to 140 mg/ml, 20 mg/ml to 130 mg/ml, 20 mg/ml to 120 mg/ml, 20 mg/ml to 110 mg/ml, 20 mg/ml to 100 mg/ml, 20 mg/ml to 90 mg/ml, 20 mg/ml to 80 mg/ml, 20 mg/ml to 70 mg/ml, 20 mg/ml to 60 mg/ml, 20 mg/ml to 50 mg/ml, 20 mg/ml to 40 mg/ml, 20 mg/ml to 30 mg/ml, 30 mg/ml to 180 mg/ml, 30 mg/ml to 170 mg, 30 mg/ml to 160 mg/ml, 30 mg/ml to 150 mg/ml, 30 mg/ml to 140 mg/ml, 30 mg/ml to 130 mg/ml, 30 mg/ml to 120 mg/ml, 30 mg/ml to 110 mg/ml, 30 mg/ml to 100 mg/ml, 30 mg/ml to 90 mg/ml, 30 mg/ml to 80 mg/ml, 30 mg/ml to 70 mg/ml, 30 mg/ml to 60 mg/ml, 30 mg/ml to 50 mg/ml, 30 mg/ml to 40 mg/ml, 40 mg/ml to 180 mg/ml, 40 mg/ml to 170 mg, 40 mg/ml to 160 mg/ml, 40 mg/ml to 150 mg/ml, 40 mg/ml to 140 mg/ml, 40 mg/ml to 130 mg/ml, 40 mg/ml to 120 mg/ml, 40 mg/ml to 110 mg/ml, 40 mg/ml to 100 mg/ml, 40 mg/ml to 90 mg/ml, 40 mg/ml to 80 mg/ml, 40 mg/ml to 70 mg/ml, 40 mg/ml to 60 mg/ml, 40 mg/ml to 50 mg/ml, 50 mg/ml to 180 mg/ml, 50 mg/ml to 170 mg, 50 mg/ml to 160 mg/ml, 50 mg/ml to 150 mg/ml, 50 mg/ml to 140 mg/ml, 50 mg/ml to 130 mg/ml, 50 mg/ml to 120 mg/ml, 50 mg/ml to 110 mg/ml, 50 mg/ml to 100 mg/ml, 50 mg/ml to 90 mg/ml, 50 mg/ml to 80 mg/ml, 50 mg/ml to 70 mg/ml, 50 mg/ml to 60 mg/ml, 60 mg/ml to 180 mg/ml, 60 mg/ml to 170 mg, 60 mg/ml to 160 mg/ml, 60 mg/ml to 150 mg/ml, 60 mg/ml to 140 mg/ml, 60 mg/ml to 130 mg/ml, 60 mg/ml to 120 mg/ml, 60 mg/ml to 110 mg/ml, 60 mg/ml to 100 mg/ml, 60 mg/ml to 90 mg/ml, 60 mg/ml to 80 mg/ml, 60 mg/ml to 70 mg/ml, 70 mg/ml to 180 mg/ml, 70 mg/ml to 170 mg, 70 mg/ml to 160 mg/ml, 70 mg/ml to 150 mg/ml, 70 mg/ml to 140 mg/ml, 70 mg/ml to 130 mg/ml, 70 mg/ml to 120 mg/ml, 70 mg/ml to 110 mg/ml, 70 mg/ml to 100 mg/ml, 70 mg/ml to 90 mg/ml, 70 mg/ml to 80 mg/ml, 80 mg/ml to 180 mg/ml, 80 mg/ml to 170 mg, 80 mg/ml to 160 mg/ml, 80 mg/ml to 150 mg/ml, 80 mg/ml to 140 mg/ml, 80 mg/ml to 130 mg/ml, 80 mg/ml to 120 mg/ml, 80 mg/ml to 110 mg/ml, 80 mg/ml to 100 mg/ml, 80 mg/ml to 90 mg/ml, 90 mg/ml to 180 mg/ml, 90 mg/ml to 170 mg, 90 mg/ml to 160 mg/ml, 90 mg/ml to 150 mg/ml, 90 mg/ml to 140 mg/ml, 90 mg/ml to 130 mg/ml, 90 mg/ml to 120 mg/ml, 90 mg/ml to 110 mg/ml, 90 mg/ml to 100 mg/ml, 100 mg/ml to 180 mg/ml, 100 mg/ml to 170 mg, 100 mg/ml to 160 mg/ml, 100 mg/ml to 150 mg/ml, 100 mg/ml to 140 mg/ml, 100 mg/ml to 130 mg/ml, 100 mg/ml to 120 mg/ml, 100 mg/ml to 110 mg/ml, 110 mg/ml to 180 mg/ml, 110 mg/ml to 170 mg, 110 mg/ml to 160 mg/ml, 110 mg/ml to 150 mg/ml, 110 mg/ml to 140 mg/ml, 110 mg/ml to 130 mg/ml, 110 mg/ml to 120 mg/ml, 120 mg/ml to 180 mg/ml, 120 mg/ml to 170 mg, 120 mg/ml to 160 mg/ml, 120 mg/ml to 150 mg/ml, 120 mg/ml to 140 mg/ml, 120 mg/ml to 130 mg/ml, 130 mg/ml to 180 mg/ml, 130 mg/ml to 170 mg, 130 mg/ml to 160 mg/ml, 130 mg/ml to 150 mg/ml, 130 mg/ml to 140 mg/ml, 140 mg/ml to 180 mg/ml, 140 mg/ml to 170 mg/ml, 140 mg/ml to 160 mg/ml, 140 mg/ml to 150 mg/ml, 150 mg/ml to 180 mg/ml, 150 mg/ml to 170 mg/ml, 150 mg/ml to 160 mg/ml, 160 mg/ml to 180 mg/ml, 160 mg/ml to 170 mg/ml, and 170 mg/ml to 180 mg/ml.

Embodiment 38. The method of any one of embodiments 27 to 37, wherein the pharmaceutical composition is a form of a dosage unit, wherein the dosage unit is characterized by a volume selected from:

a) 0.1 ml to 1.5 ml, 0.1 ml to 1.4 ml, 0.1 ml to 1.3 ml, 0.1 ml to 1.2 ml, 0.1 ml to 1.1 ml, 0.1 ml to 1.0 ml, 0.1 ml to 0.9 ml, 0.1 ml to 0.8 ml, 0.1 ml to 0.7 ml, 0.1 ml to 0.6 ml, 0.1 ml to 0.5 ml, 0.1 ml to 0.4 ml, 0.1 ml to 0.3 ml, 0.1 ml to 0.2 ml, 0.2 ml to 1.5 ml, 0.2 ml to 1.4 ml, 0.2 ml to 1.3 ml, 0.2 ml to 1.2 ml, 0.2 ml to 1.1 ml, 0.2 ml to 1.0 ml, 0.2 ml to 0.9 ml, 0.2 ml to 0.8 ml, 0.2 ml to 0.7 ml, 0.2 ml to 0.6 ml, 0.2 ml to 0.5 ml, 0.2 ml to 0.4 ml, 0.2 ml to 0.3 ml, 0.3 ml to 1.5 ml, 0.3 ml to 1.4 ml, 0.3 ml to 1.3 ml, 0.3 ml to 1.2 ml, 0.3 ml to 1.1 ml, 0.3 ml to 1.0 ml, 0.3 ml to 0.9 ml, 0.3 ml to 0.8 ml, 0.3 ml to 0.7 ml, 0.3 ml to 0.6 ml, 0.3 ml to 0.5 ml, 0.3 ml to 0.4 ml, 0.4 ml to 1.5 ml, 0.4 ml to 1.4 ml, 0.4 ml to 1.3 ml, 0.4 ml to 1.2 ml, 0.4 ml to 1.1 ml, 0.4 ml to 1.0 ml, 0.4 ml to 0.9 ml, 0.4 ml to 0.8 ml, 0.4 ml to 0.7 ml, 0.4 ml to 0.6 ml, 0.4 ml to 0.5 ml, 0.5 ml to 1.5 ml, 0.5 ml to 1.4 ml, 0.5 ml to 1.3 ml, 0.5. ml to 1.2 ml, 0.5 ml to 1.1 ml, 0.5 ml to 1.0 ml, 0.5 ml to 0.9 ml, 0.5 ml to 0.8 ml, 0.5 ml to 0.7 ml, 0.5 ml to 0.6 ml, 0.6 ml to 1.5 ml, 0.6 ml to 1.4 ml, 0.6 mo to 1.3 ml, 0.6 ml to 1.2 ml, 0.6 ml to 1.1 ml, 0.6 ml to 1.0 ml, 0.6 ml to 0.9 ml, 0.6 ml to 0.8 ml, 0.6 ml to 0.7 ml, 0.7 ml, to 1.5 ml, 0.7 ml to 1.4 ml, 0.7 ml to 1.3 ml, 0.7 ml to 1.2 ml, 0.7 ml to 1.1 ml, 0.7 ml to 1.0 ml, 0.7 ml to 0.9 ml, 0.7 ml to 0.8 ml, 0.8 ml to 1.5 ml, 0.8 ml to 1.4 ml, 0.8 ml to 1.3 ml, 0.8 ml to 1.2 ml, 0.8 ml to 1.1 ml, 0.8 ml to 1.0 ml. 0.8 ml to 0.9 ml, 0.9 ml, to 1.5 ml, 0.9 ml to 1.4 ml, 0.9 ml to 1.3 ml, 0.9 ml to 1.2 ml, 0.9 ml, to 1.1 ml, 0.9 ml to 1.0 ml, 1.0 ml to 1.5 ml, 1.0 ml to 1.4 ml, 1.0 ml to 1.3 ml, 1.0 ml to 1.2 ml, 1.0 ml to 1.1 ml, 1.1 ml to 1.5 ml, 1.1 ml to 1.4 ml, 1.1 ml to 1.3 ml, 1.1 ml to 1.2 ml, 1.2 ml to 1.5 ml, 1.2 ml to 1.4 ml, 1.2 ml to 1.3 ml, 1.3 ml to 1.5 ml, 1.3 ml to 1.4 ml, 1.4 ml to, 1.5 ml; and b) about 0.1 ml to about 1.5 ml, about 0.1 ml to about 1.4 ml, about 0.1 ml to about 1.3 ml, about 0.1 ml to about 1.2 ml, about 0.1 ml to about 1.1 ml, about 0.1 ml to about 1.0 ml, about 0.1 ml to about 0.9 ml, about 0.1 ml to about 0.8 ml, about 0.1 ml to about 0.7 ml, about 0.1 ml to about 0.6 ml, about 0.1 ml to about 0.5 ml, about 0.1 ml to about 0.4 ml, about 0.1 ml to about 0.3 ml, about 0.1 ml to about 0.2 ml, about 0.2 ml to about 1.5 ml, about 0.2 ml to about 1.4 ml, about 0.2 ml to about 1.3 ml, about 0.2 ml to about 1.2 ml, about 0.2 ml to about 1.1 ml, about 0.2 ml to about 1.0 ml, about 0.2 ml to about 0.9 ml, about 0.2 ml to about 0.8 ml, about 0.2 ml to about 0.7 ml, about 0.2 ml to about 0.6 ml, about 0.2 ml to about 0.5 ml, about 0.2 ml to about 0.4 ml, about 0.2 ml to about 0.3 ml, about 0.3 ml to about 1.5 ml, about 0.3 ml to about 1.4 ml, about 0.3 ml to about 1.3 ml, about 0.3 ml to about 1.2 ml, about 0.3 ml to about 1.1 ml, about 0.3 ml to about 1.0 ml, about 0.3 ml to about 0.9 ml, about 0.3 ml to about 0.8 ml, about 0.3 ml to about 0.7 ml, about 0.3 ml to about 0.6 ml, about 0.3 ml to about 0.5 ml, about 0.3 ml to about 0.4 ml, about 0.4 ml to about 1.5 ml, about 0.4 ml to about 1.4 ml, about 0.4 ml to about 1.3 ml, about 0.4 ml to about 1.2 ml, about 0.4 ml to about 1.1 ml, about 0.4 ml to about 1.0 ml, about 0.4 ml to about 0.9 ml, about 0.4 ml to about 0.8 ml, about 0.4 ml to about 0.7 ml, about 0.4 ml to about 0.6 ml, about 0.4 ml to about 0.5 ml, about 0.5 ml to about 1.5 ml, about 0.5 ml to about 1.4 ml, about 0.5 ml to about 1.3 ml, about 0.5. ml to about 1.2 ml, about 0.5 ml to about 1.1 ml, about 0.5 ml to about 1.0 ml, about 0.5 ml to about 0.9 ml, about 0.5 ml to about 0.8 ml, about 0.5 ml to about 0.7 ml, about 0.5 ml to about 0.6 ml, about 0.6 ml to about 1.5 ml, about 0.6 ml to about 1.4 ml, about 0.6 ml to about 1.3 ml, about 0.6 ml to about 1.2 ml, about 0.6 ml to about 1.1 ml, about 0.6 ml to about 1.0 ml, about 0.6 ml to about 0.9 ml, about 0.6 ml to about 0.8 ml, about 0.6 ml to about 0.7 ml, about 0.7 ml, about to about 1.5 ml, about 0.7 ml to about 1.4 ml, about 0.7 ml to about 1.3 ml, about 0.7 ml to about 1.2 ml, about 0.7 ml to about 1.1 ml, about 0.7 ml to about 1.0 ml, about 0.7 ml to about 0.9 ml, about 0.7 ml to about 0.8 ml, about 0.8 ml to about 1.5 ml, about 0.8 ml to about 1.4 ml, about 0.8 ml to about 1.3 ml, about 0.8 ml to about 1.2 ml, about 0.8 ml to about 1.1 ml, about 0.8 ml to about 1.0 ml. 0.8 ml to about 0.9 ml, about 0.9 ml, about to about 1.5 ml, about 0.9 ml to about 1.4 ml, about 0.9 ml to about 1.3 ml, about 0.9 ml to about 1.2 ml, about 0.9 ml, about to about 1.1 ml, about 0.9 ml to about 1.0 ml, about 1.0 ml to about 1.5 ml, about 1.0 ml to about 1.4 ml, about 1.0 ml to about 1.3 ml, about 1.0 ml to about 1.2 ml, about 1.0 ml to about 1.1 ml, about 1.1 ml to about 1.5 ml, about 1.1 ml to about 1.4 ml, about 1.1 ml to about 1.3 ml, about 1.1 ml to about 1.2 ml, about 1.2 ml to about 1.5 ml, about 1.2 ml to about 1.4 ml, about 1.2 ml to about 1.3 ml, about 1.3 ml to about 1.5 ml, about 1.3 ml to about 1.4 ml, and about 1.4 ml to about 1.5 ml.

Embodiment 39. The method of any one of embodiments 27-38, comprising administering a first dose and a second dose of the pharmaceutical composition.

Embodiment 40. The method of embodiment 39, wherein the first dose and the second dose are separated by 5, 10, 15, 20, 25, 30, 35, or 40 days.

Embodiment 41. The method of embodiment 39, wherein the first dose and the second dose are separated by 20, 21, 22, 23, 24, 25, 26, 27, 28, 29, 30, 31, 32, 33, 34, 35, 36, 37, 38, 39, or 40 days.

Embodiment 42. The method of embodiment 39, wherein the first dose and the second dose are separated by 1, 2, 3, 4, 5, 6, 7, 8, 9, or 10 weeks.

Embodiment 43. The method of embodiment 39, wherein the first dose and the second dose are separated by 1, 2, 3, 4, 5, or 6 months.

Embodiment 44. The method of embodiment 39, comprising administering the pharmaceutical composition monthly or about monthly.

Embodiment 45. The method of embodiment 44, comprising administering the pharmaceutical composition for at least two months, at least three months, at least four months, at least five months, or at least six months.

Embodiment 46. The method of embodiment 39, comprising administering the pharmaceutical composition weekly or about weekly.

Embodiment 47. The method of embodiment 46, comprising administering the pharmaceutical composition to the animal weekly or about weekly for less than 2 weeks, less than 3 weeks, less than 4 weeks, less than 5 weeks, less than 6 weeks, less than 8 week, less than 12 weeks, less than 16 weeks, or less than 20 weeks.

Embodiment 48. The method of any one of embodiments 27-47, wherein administering comprises performing a subcutaneous injection on the animal.

Embodiment 49. The method of any one of embodiments 27-48, wherein administering comprises self-administration.

Embodiment 50. The method of any one of embodiments 27-47, wherein administering comprises performing an intravenous injection on the animal.

Embodiment 51. The method of any one of embodiments 27-50, comprising administering the pharmaceutical composition at least 1, at least 2, at least 3, at least 4, at least 5, at least 6, at least 8, or at least 10 times.

Embodiment 52. The method of any one of embodiments 27-50, comprising administering the pharmaceutical composition less than 20 times, less than 15 times, less than 10 times, or less than 5 times.

Embodiment 53. The method of any one of embodiments 27-52, wherein the animal has been identified as having a thromboembolic condition or has been identified as being at risk of having a thromboembolic condition.

Embodiment 54. The method of embodiment 53, further comprising identifying the animal as having the thromboembolic condition or at risk for having the thromboembolic condition.

Embodiment 55. The method of any one of embodiments 27-54, wherein the animal has been identified as having a disease selected from end stage renal disease (ESRD), chronic kidney disease (CKD), and coronary artery disease (CAD), or has been identified as being at risk for a disease selected from ESRD, CKD, and CAD.

Embodiment 56. The method of embodiment 55, further comprising identifying the animal as having the disease, or identifying the animal as being at risk for having the disease.

Embodiment 57. A method comprising administering a first dose and a second dose of an oligomeric compound according to the following formula:

(SEQ ID NO: 3)

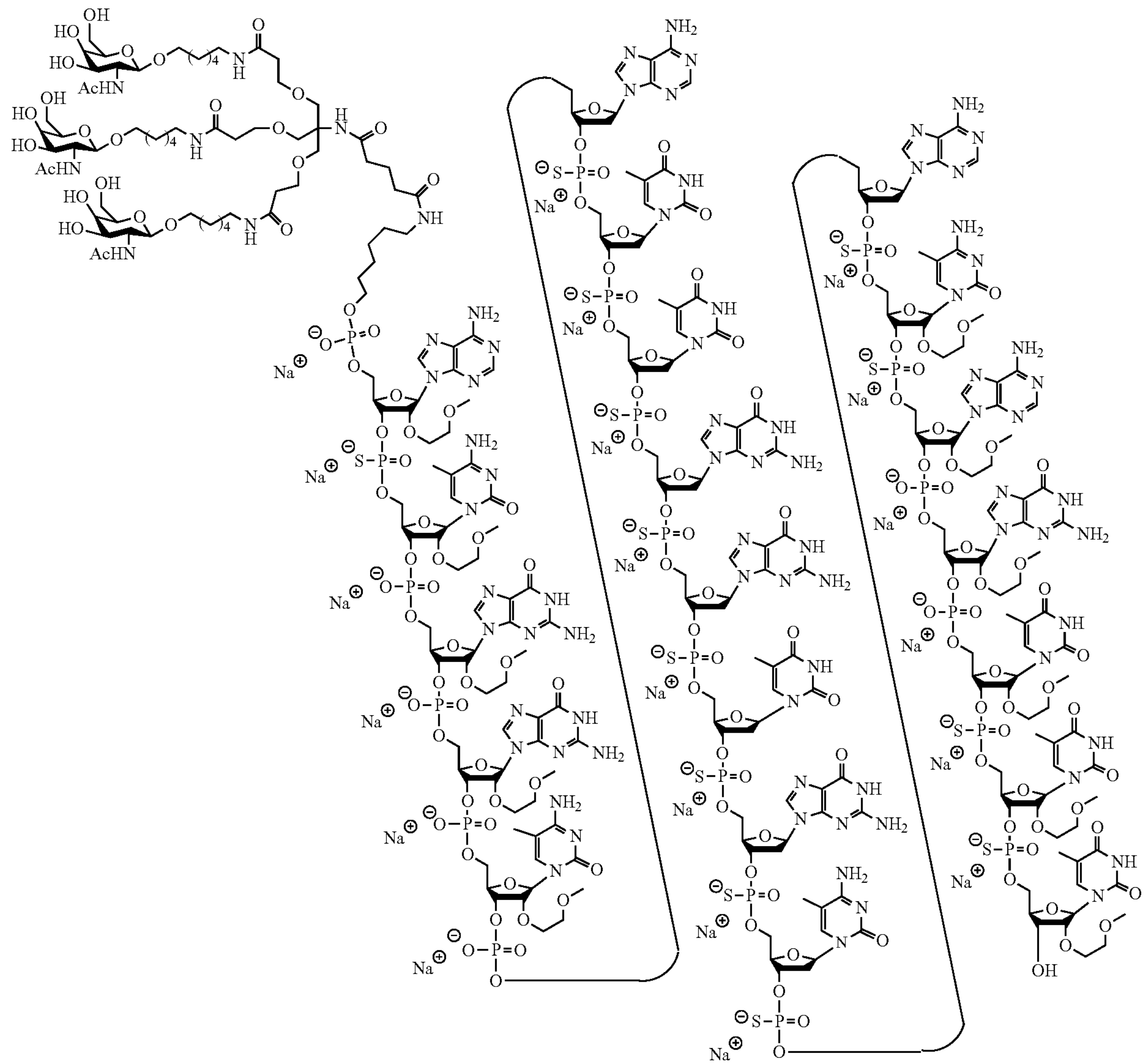

wherein the first dose and the second dose are separated by 20 to 40 days, and wherein the oligomeric compound is in the form of a dosage unit consisting or consisting essentially of about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg of the oligomeric compound and about 0.4 ml, about 0.5 ml, about 0.6 ml, about 0.7 ml, about 0.8 ml, about 0.9 ml, or about 1 ml of a pharmaceutically acceptable carrier or diluent.

Embodiment 58. The method of embodiment 57, wherein the first dose and the second dose are separated by 27 to 32 days, and wherein the dosage unit consists or consists essentially of 75 mg to 85 mg of the oligomeric compound and 0.7 ml to 0.9 ml of the pharmaceutically acceptable carrier or diluent.

Embodiment 59. The method of embodiment 57, wherein the dosage unit consists or consists essentially of about 80 mg of the oligomeric compound and about 0.8 ml of the pharmaceutically acceptable carrier or diluent.

Embodiment 60. A method comprising administering a dosage unit to an animal monthly, wherein the dosage unit consists or consists essentially of the oligomeric compound of any one of embodiments 1-5 and a pharmaceutically acceptable carrier or diluent, and wherein the concentration of the oligomeric compound is 80 mg/ml to 120 mg/ml.

Embodiment 61. A method comprising administering a dosage unit to an animal monthly, wherein the dosage unit consists or consists essentially of the oligomeric compound of any one of embodiments 1-5 and a pharmaceutically acceptable carrier or diluent, and wherein the concentration of the oligomeric compound is about 100 mg/ml.

Embodiment 62. The method of any one of embodiments 57 to 61, wherein the pharmaceutically acceptable carrier or diluent is phosphate buffered saline.

Embodiment 63. A lyophilized powder comprising the oligomeric compound of any one of claims 1-5.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836).

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, $OCH_3$, and $OCH_2CH_2OCH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("ENA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022, 193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J. Org. Client.,* 2009, 74, 118-134), 4'-$CH_2$—C(=$CH_2$)-2' and analogs thereof (see e.g., Seth et al., U.S. Pat. No. 8,278, 426), 4'C(—$R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —C($R_a$)=C($R_b$)—, —C($R_a$)=N—, C(=—$NR_a$)—, —C(=O)—, —C(=S)—, —O—, —$Si(R_a)_2$—, —$S(=O)_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794, 499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

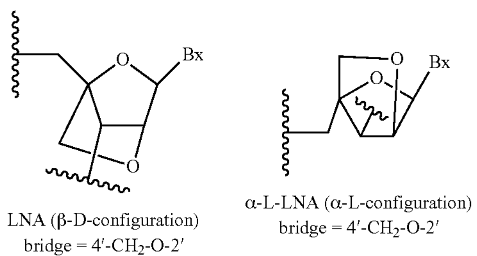

LNA (β-D-configuration) bridge = 4'-$CH_2$-O-2'    α-L-LNA (α-L-configuration) bridge = 4'-$CH_2$-O-2'

α-L-methyleneoxy (4'-$CH_2$—O-2') or α-L-LNA bicyclic nucleosides have been incorporated into oligonucleotides that showed antisense activity (Frieden et al., *Nucleic Acids Research,* 2003, 27, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

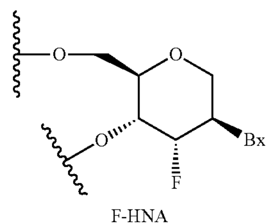

F-HNA ("F-HNA", see e.g., Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005, 906; F-HNA can also be referred to as a F-THP or 3'-fluoro tetrahydropyran), and nucleosides comprising additional modified THP compounds having the formula:

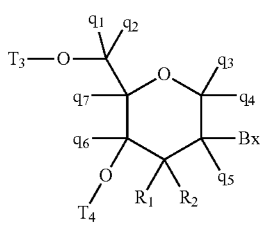

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, W and $q_7$ are each, independently, H, CVO, alkyl, substituted $C_1$-$C_6$ alkyl, $C_2$-$C_6$ alkenyl, substituted $C_2$-$C_6$, alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$, alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

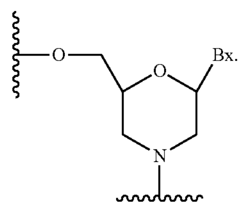

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, II, 5853-5865), and nucleosides and oligonucleotides described in Manoharan et al., WO2011/133876.

Many other bicyclic and tricyclic sugar and sugar surrogate ring systems are known in the art that can be used in modified nucleosides (see for example review article: Leumann, Bioorg. Med. Chem., 2002, 10, 841-854).

2. Certain Modified Nucleobases

In certain embodiments, modified oligonucleotides comprise one or more nucleosides comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C≡C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No.

5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters ("P═O") (also referred to as unmodified or naturally occurring linkages or phosphate linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—$CH_2$—N($CH_3$)—O—$CH_2$—), thiodiester, thionocarbamate (—O—C(═O)(NH)—S—); siloxane (—O—$SiH_2$—O—); and N,N'-dimethylhydrazine (—$CH_2$—N($CH_3$)—N($CH_3$)—). Modified internucleoside linkages, compared to naturally occurring phosphodiester linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

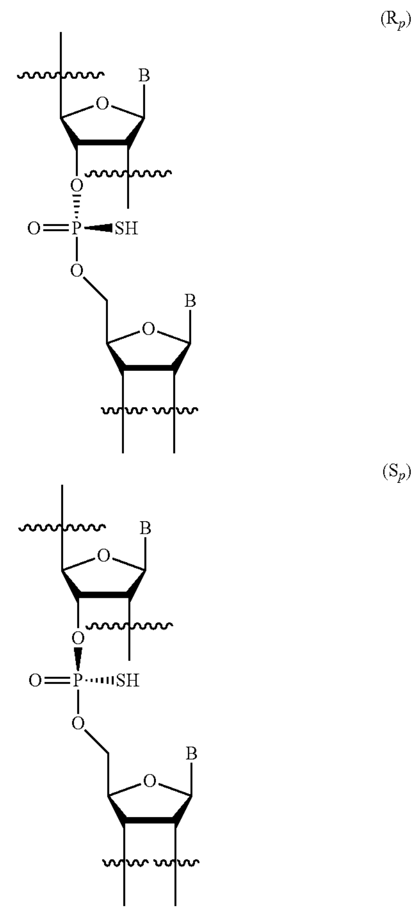

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleoside sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P═O). In certain embodiments, each internucleoside linking group of a modified oligonucleotide is a phosphorothioate internucleoside linkage (P═S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moieties and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups are attached to the 3' and/or 5' end of oligonucleotides. In certain embodiments, conjugate groups that are attached to either or both ends of an oligonucleotide are terminal groups. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 7264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 76, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to react with particular site on a parent compound and the other is selected to react with a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

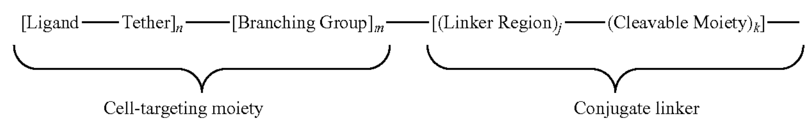

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactosamine (GalNAc), mannose, glucose, glucosamine and fucose. In certain embodiments, each ligand is N-acetyl galactosamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

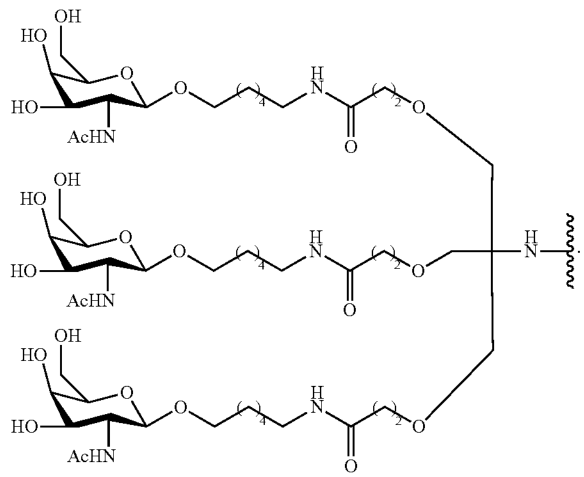

In certain embodiments, conjugate groups comprise a cell-targeting moiety having the formula:

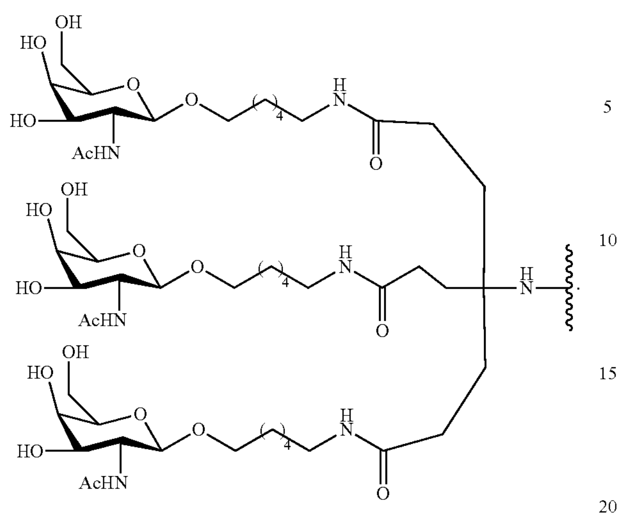
In certain embodiments, conjugate groups comprise a cell-targeting moiety having the formula:
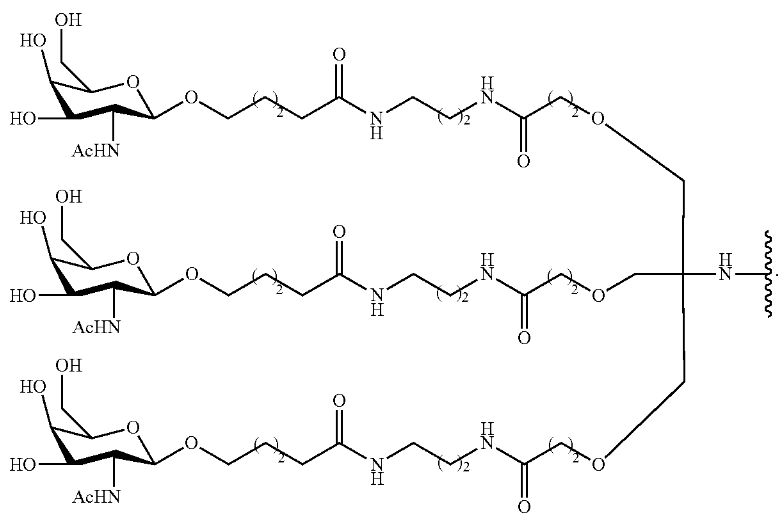
In certain embodiments, compounds described herein comprise a conjugate group described herein as "THA-GalNAac3". THA-GalNAc$_3$ is shown below without the optional cleavable moiety at the end of the linker region:

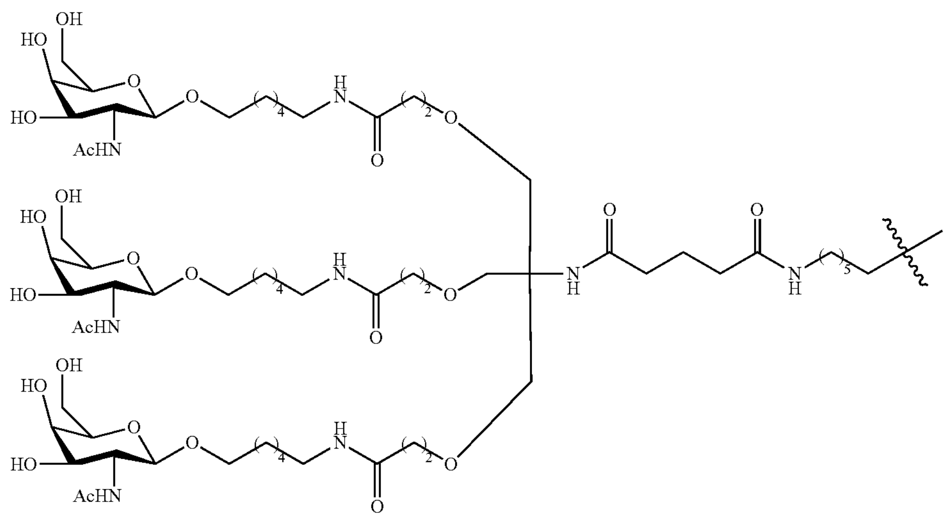

In certain embodiments, compounds described herein comprise THA-GalNAc$_3$-phosphate, also represented as (THA-GalNAc$_3$)o, having the formula:

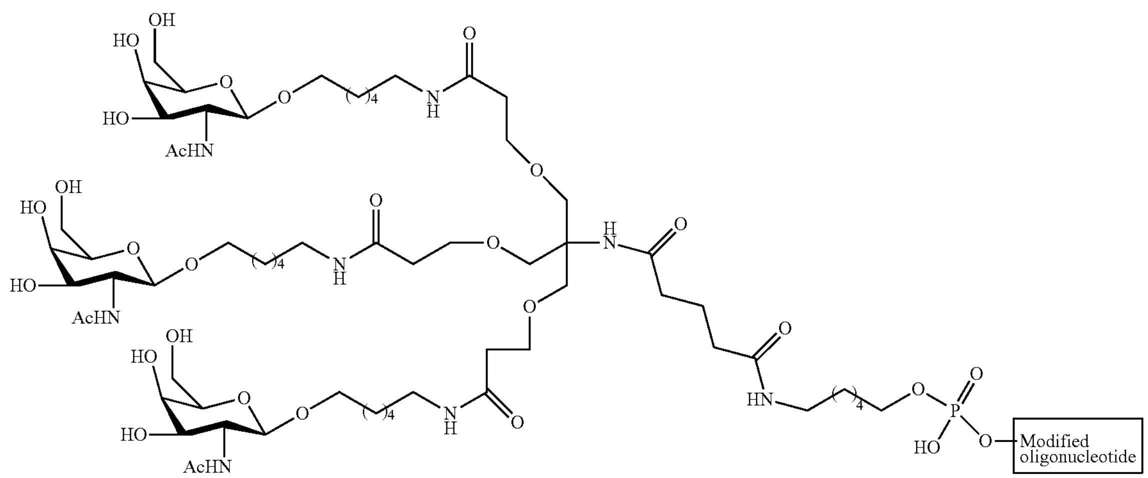

wherein modified oligonucleotide represents a modified oligonucleotide.

Representative publications that teach the preparation of certain of the above noted conjugate groups and compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, 9,127,276, US 2006/0148740, US 2011/0123520, WO 2013/033230 and WO 2012/037254, Biessen et al., *J. Med Chem.* 1995, 38, 1846-1852, Lee et al., *Bioorganic & Medicinal Chemistry* 2011, 19, 2494-2500, Rensen et al., *J. Biol. Chem.* 2001, 276, 37577-37584, Rensen et al., *J. Med. Chem.* 2004, 47, 5798-5808, Sliedregt et al., *J. Med. Chem.* 1999, 42, 609-618, and Valentijn et al., *Tetrahedron,* 1997, 53, 759-770, each of which is incorporated by reference herein in its entirety.

In certain embodiments, compounds described herein comprise modified oligonucleotides comprising a gapmer or fully modified motif and a conjugate group comprising at least one, two, or three GalNAc ligands. In certain embodiments compounds described herein comprise a conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., Analyt Biochem, 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618;

Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, *Antisense Nucleic Acid Drug Dev,* 2002, 12, 103-128; Merwin et al., *Bioconjug Chem,* 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO 1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, antisense compounds described herein are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. FXI

In certain embodiments, oligomeric compounds comprise or consist of an oligonucleotide comprising a region that is complementary to a target nucleic acid, wherein the target nucleic acid is FXI. In certain embodiments, FXI nucleic acid has the sequence set forth in SEQ ID NO: 1 (the complement of GENBANK Accession No: NT_022792.17 truncated from nucleobase 19598000 to Ser. No. 19/624,000) and SEQ ID NO: 2 (GENBANK Accession No: NM_000128.3).

In certain embodiments, methods comprise contacting a cell with an oligomeric compound disclosed herein. In certain embodiments, methods comprise administering an oligomeric compound disclosed herein to an animal, thereby contacting a cell in the animal. In certain embodiments, contacting a cell with an oligomeric compound comprising a modified oligonucleotide complementary to SEQ ID NO: 1 or SEQ ID NO: 2 reduces the amount of FXI RNA, and in certain embodiments reduces the amount of FXI protein. In certain embodiments, the oligomeric compound consists of a conjugate group attached to the 5' end of a modified oligonucleotide. In certain embodiments, contacting a cell in an animal with an oligomeric compound comprising a modified oligonucleotide complementary to SEQ ID NO: 1 or SEQ ID NO: 2 treats, prevents, or ameliorates a thromboembolic condition. In certain embodiments, the thromboembolic condition is deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. In certain embodiments, the oligomeric compound consists of a conjugate group attached to the 5' end of a modified oligonucleotide. In certain embodiments, contacting a cell in an animal with an oligomeric compound comprising a modified oligonucleotide complementary to SEQ ID NO: 1 or SEQ ID NO: 2 treats, prevents, or ameliorates a thromboembolic condition without increasing bleeding risk. In certain embodiments, the thromboembolic condition is deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. In certain embodiments, the oligomeric compound consists of a conjugate group attached to the 5' end of a modified oligonucleotide.

A FXI RNA may be quantified, e.g., by quantitative PCR. FXI proteins may be quantified with standard protein quantification tests, e.g., ELISA. The FXI protein may be an inactive form (zymogen). The FXI protein may be an active form (FXIa). The active form of FXI may promote converting FIX from its inactive form (FIX) to its active form (FIXa). FXI activity may be assessed with a blood test that characterizes coagulation of blood. Non-limiting examples of such blood tests are a partial thromboplastin time (PTT) test or activated partial thromboplastin time test (aPTT or APTT). FXI activity in a test plasma sample may be assayed by adding the test plasma sample to a plasma sample that is immunodepleted of FXI and comparing clotting of the resulting combined sample to a reference sample with a reference amount of FXI.

In certain embodiments, contacting a cell in an animal with an oligomeric compound comprising a modified oligonucleotide complementary to SEQ ID NO: 1 or SEQ ID NO: 2 treats, prevents, or ameliorates a thromboembolic condition. In certain embodiments, the thromboembolic condition is deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. In certain embodiments, the oligomeric compound consists of a conjugate group attached to the 5' end of a modified oligonucleotide. In certain embodiments, contacting a cell in an animal with an oligomeric compound comprising a modified oligonucleotide complementary to SEQ ID NO: 1 or SEQ ID NO: 2 treats, prevents, or ameliorates a thromboembolic condition without increasing bleeding risk. In certain embodiments, the thromboembolic condition is deep vein thrombosis, venous or arterial thrombosis, pulmonary embolism, myocardial infarction, stroke, thrombosis associated with chronic kidney disease or end-stage renal disease (ESRD), including thrombosis associated with dialysis, or other procoagulant condition. In certain embodiments, the oligomeric compound consists or consists essentially of a conjugate group attached to the 5' end of a modified oligonucleotide.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the alimentary and/or excretory system. Such cells and tissues include the liver, kidney, and pancreas.

VI. Certain Pharmaceutical Compositions

In certain embodiments, pharmaceutical compositions described herein comprise one or more oligomeric compounds. In certain embodiments, the one or more oligomeric compounds each comprise a modified oligonucleotide. In certain embodiments, the pharmaceutical composition comprises a pharmaceutically acceptable diluent or carrier. In certain embodiments, a pharmaceutical composition comprises a sterile saline solution and one or more oligomeric compounds. In certain embodiments, a pharmaceutical composition consists or consists essentially of a sterile saline solution and one or more oligomeric compounds. In certain embodiments, the sterile saline is pharmaceutical grade saline. In certain embodiments, a pharmaceutical composition comprises one or more oligomeric compounds and sterile water. In certain embodiments, a pharmaceutical composition consists or consists essentially of one or more oligomeric compounds and sterile water. In certain embodiments, the sterile water is pharmaceutical grade water. In certain embodiments, the pharmaceutically acceptable diluent or carrier is distilled water for injection. In certain embodiments, a pharmaceutical composition comprises one or more oligomeric compound and phosphate-buffered saline (PBS). In certain embodiments, a pharmaceutical composition consists or consists essentially of one or more oligomeric compounds and PBS. In certain embodiments, the sterile PBS is pharmaceutical grade PBS. In certain embodiments, a pharmaceutical composition comprises one or more oligomeric compound and artificial cerebrospinal fluid. In certain embodiments, the sterile PBS is pharmaceutical grade PBS. In certain embodiments, a pharmaceutical composition consists or consists essentially of artificial cerebrospinal fluid. In certain embodiments, the artificial cerebrospinal fluid is pharmaceutical grade.

In certain embodiments, pharmaceutical compositions comprise one or more oligomeric compounds disclosed herein and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound disclosed herein encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue.

In certain embodiments, a lipid moiety is selected to increase distribution of a pharmaceutical agent to muscle tissue.

In certain embodiments, pharmaceutical compositions disclosed herein comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver oligomeric compounds described herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions disclosed herein are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Under certain conditions, certain compounds disclosed herein act as acids. Although such compounds may be drawn or described in protonated (free acid) form, in ionized (anion) form, or ionized and in association with a cation (salt) form, aqueous solutions of such compounds exist in equilibrium among such forms. For example, a phosphate linkage of an oligonucleotide in aqueous solution exists in equilibrium among free acid, anion, and salt forms. Unless otherwise indicated, compounds described herein are intended to include ah such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include ah such forms. Drawn structures necessarily depict a single form. Nevertheless, unless otherwise indicated, such drawings are likewise intended to include corresponding forms. Herein, a structure depicting the free acid of a compound followed by the term "or salts thereof" expressly includes ah such forms that may be fully or partially protonated/de-protonated/in association with a cation. In certain instances, one or more specific cation is identified.

In certain embodiments, oligomeric compounds disclosed herein are in aqueous solution with sodium. In certain embodiments, oligomeric compounds are in aqueous solution with potassium. In certain embodiments, oligomeric compounds are in PBS. In certain embodiments, oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of an oligomeric compound in milligrams indicates the mass of the free acid form of the oligomeric compound. As described above, in aqueous solution, the free acid is in equilibrium with anionic and salt forms. However, for the purpose of calculating dose, it is assumed that the oligomeric compound exists as a solvent-free, sodium-acetate free, anhydrous, conjugated free acid. For example, where an oligomeric compound is in solution comprising sodium (e.g., saline), the oligomeric compound may be partially or fully de-protonated and in association with $Na^+$ ions. However, the mass of the protons are nevertheless counted toward the weight of the dose, and the mass of the $Na^+$ ions are not counted toward the weight of the dose. Thus, for example, a dose, or dosage unit, of 80 mg of Compound No. 957943 equals the number of fully protonated molecules that weighs 80 mg. This would be equivalent to 84 mg of solvent-free, sodium-acetate free, anhydrous sodiated Compound No. 957943. When an oligomeric compound comprises a conjugate, the mass of conjugate is included in calculating the dose of such oligomeric compound.

VII. Certain Dosage Amounts

In certain embodiments, pharmaceutical compositions described herein are administered in the form of a dosage unit. The dosage unit may be prepared for injection. The dosage unit may be prepared for infusion. In certain embodiments, the dosage unit comprises an oligomeric compound disclosed herein and a pharmaceutically acceptable carrier or diluent. In certain embodiments, the dosage unit consists or consists essentially of an oligomeric compound disclosed herein and a pharmaceutically acceptable carrier or diluent. In certain embodiments, the oligomeric compound comprises a modified oligonucleotide having the nucleobase sequence of SEQ ID NO: 3. In certain embodiments, the oligomeric compound is Compound No. 957943.

In certain embodiments, the oligomeric compound is present in the dosage unit at an amount selected from 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, and 300 mg. In certain embodiments, the oligomeric compound is present in the dosage unit at an amount selected from about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg.

In certain embodiments, the oligomeric compound is present in the dosage unit at an amount selected from 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, and 140 mg. In certain embodiments, the oligomeric compound is present in the dosage unit at an amount selected from about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 128 mg, about 129 mg, about 130 mg, about 131 mg, about 132 mg, about 133 mg, about 134 mg, about 135 mg, about 136 mg, about 137 mg, about 138 mg, about 139 mg, and about 140 mg.

In certain embodiments, the oligomeric compound is present in the dosage unit at an amount selected from 75.0 mg, 75.1 mg, 75.2 mg, 75.3 mg, 75.4 mg, 75.5 mg, 75.6 mg, 75.7 mg, 75.8 mg, 75.9 mg, 76.0 mg, 76.1 mg, 76.2 mg, 76.3 mg. 76.4 mg, 76.5 mg, 76.6 mg, 76.7 mg, 76.8 mg, 76.9 mg, 77.0 mg, 77.1 mg, 77.2 mg, 77.3 mg, 77.4 mg, 77.5 mg, 77.6 mg, 77.7 mg, 77.8 mg, 77.9 mg, 78.0 mg, 78.1 mg, 78.2 mg, 78.3 mg. 78.4 mg, 78.5 mg, 78.6 mg, 78.7 mg, 78.8 mg, 78.9 mg, 79.0 mg, 79.1 mg, 79.2 mg, 79.3 mg, 79.4 mg, 79.5 mg, 79.6 mg, 79.7 mg, 79.8 mg, 79.9 mg, 80.0 mg, 80.1 mg, 80.2 mg, 80.3 mg. 80.4 mg, 80.5 mg, 80.6 mg, 80.7 mg, 80.8 mg, 80.9 mg, 81.0 mg, 81.1 mg, 81.2 mg, 81.3 mg, 81.4 mg, 81.5 mg, 81.6 mg, 81.7 mg, 81.8 mg, 81.9 mg, 82.0 mg, 82.1 mg, 82.2 mg, 82.3 mg. 82.4 mg, 82.5 mg, 82.6 mg, 82.7 mg, 82.8 mg, 82.9 mg, 83.0 mg, 83.1 mg, 83.2 mg, 83.3 mg, 83.4 mg, 83.5 mg, 83.6 mg, 83.7 mg, 83.8 mg, 83.9 mg, 84.0 mg, 84.1 mg, 84.2 mg, 84.3 mg. 84.4 mg, 84.5 mg, 84.6 mg, 84.7 mg, 84.8 mg, 84.9 mg, and 85.0 mg. In certain embodiments, the oligomeric compound is present in the dosage unit at an amount selected from about 75.0 mg, about 75.1 mg, about 75.2 mg, about 75.3 mg, about 75.4 mg, about 75.5 mg, about 75.6 mg, about 75.7 mg, about 75.8 mg, about 75.9 mg, about 76.0 mg, about 76.1 mg, about 76.2 mg, about 76.3 mg. about 76.4 mg, about 76.5 mg, about 76.6 mg, about 76.6 about 76.7 mg, about 76.8 mg, about 76.9 mg, about 77.0 mg, about 77.1 mg, about 77.2 mg, about 77.3 mg, about 77.4 mg, about 77.5 mg, about 77.6 mg, about 77.7 mg, about 77.8 mg, about 77.9 mg, about 78.0 mg, about 78.1 mg, about 78.2 mg, about 78.3 mg. about 78.4 mg, about 78.5 mg, about 78.6 mg, about 78.7 mg, about 78.8 mg, about 78.9 mg, about 79.0 mg, about 79.1 mg, about 79.2 mg, about 79.3 mg, about 79.4 mg, about 79.5 mg, about 79.6 mg, about 79.7 mg, about 79.8 mg, about 79.9 mg, about 80.0 mg, about 80.1 mg, about 80.2 mg, about 80.3 mg. about 80.4 mg, about 80.5 mg, about 80.6 mg, about 80.7 mg, about 80.8 mg, about 80.9 mg, about 81.0 mg, about 81.1 mg, about 81.2 mg, about 81.3 mg, about 81.4 mg, about 81.5 mg, about 81.6 mg, about 81.7 mg, about 81.8 mg, about 81.9 mg, about 82.0 mg, about 82.1 mg, about 82.2 mg, about 82.3 mg. about 82.4 mg, about 82.5 mg, about 82.6 mg, about 82.7 mg, about 82.8 mg, about 82.9 mg, about 83.0 mg, about 83.1 mg, about 83.2 mg, about 83.3 mg, about 83.4 mg, about 83.5 mg, about 83.6 mg, about 83.7 mg, about 83.8 mg, about 83.9 mg, about 84.0 mg, about 84.1 mg, about 84.2 mg, about 84.3 mg. about 84.4 mg, about 84.5 mg, about 84.6 mg, about 84.7 mg, about 84.8 mg, about 84.9 mg, and about 85.0 mg.

In certain embodiments, the oligomeric compound is present in the dosage unit at an amount that falls within a range. In certain embodiments, the range is selected from 10 mg to 140 mg, from 10 mg to 130 mg, from 10 mg to 120 mg, from 10 mg to 110 mg, from 10 mg to 100 mg, from 10 mg to 90 mg, from 10 mg to 80 mg, from 10 mg to 70 mg, from 10 mg to 60 mg, from 10 mg to 50 mg, from 10 mg to 40 mg, from 10 mg to 30 mg, from 10 mg to 20 mg, from 20 mg to 140 mg, from 20 mg to 130 mg, from 20 mg to 120 mg, from 20 mg to 110 mg, from 20 mg to 100 mg, from 20 mg to 90 mg, from 20 mg to 80 mg, from 20 mg to 70 mg, from 20 mg to 60 mg, from 20 mg to 50 mg, from 20 mg to 40 mg, from 20 mg to 30 mg, from 30 mg to 140 mg, from 30 mg to 130 mg, from 30 mg to 120 mg, from 30 mg to 110 mg, from 30 mg to 100 mg, from 30 mg to 90 mg, from 30 mg to 80 mg, from 30 mg to 70 mg, from 30 mg to 60 mg, from 30 mg to 50 mg, from 30 mg to 40 mg, from 40 mg to 140 mg, from 40 mg to 130 mg, from 40 mg to 120 mg, from 40 mg to 110 mg, from 40 mg to 100 mg, from 40 mg to 90 mg, from 40 mg to 80 mg, from 40 mg to 70 mg, from 40 mg to 60 mg, from 40 mg to 50 mg, from 50 mg to 140 mg, from 50 mg to 130 mg, from 50 mg to 120 mg, from 50 mg to 110 mg, from 50 mg to 100 mg, from 50 mg to 90 mg, from 50 mg to 80 mg, from 50 mg to 70 mg, from 50 mg to 60 mg, from 60 mg to 140 mg, from 60 mg to 130 mg, from 60 mg to 120 mg, from 60 mg to 110 mg, from 60 mg to 100 mg, from 60 mg to 90 mg, from 60 mg to 80 mg, from 60 mg to 70 mg, from 70 mg to 140 mg, from 70 mg to 130 mg, from 70 mg to 120 mg, from 70 mg to 110 mg, from 70 mg to 100 mg, from 70 mg to 90 mg, from 70 mg to 80 mg, from 80 mg to 140 mg, from 80 mg to 130 mg, from 80 mg to 120 mg, from 80 mg to 110 mg, from 80 mg to 100 mg, from 80 mg to 90 mg, from 90 mg to 140 mg, from 90 mg to 130 mg, from 90 mg to 120 mg, from 90 mg to 110 mg, from 90 mg to 100 mg, from 100 mg to 140 mg, from 100 mg to 130 mg, from 100 mg to 120 mg, from 100 mg to 110 mg, from 110 mg to 140 mg, from 110 mg to 130 mg, from 110 mg to 120 mg, from 120 mg to 140 mg, from 120 mg to 130 mg, from 130 mg to 140 mg, from 65 mg to 95 mg, from 65 mg to 90 mg, from 65 mg to 85 mg from 65 mg to 80 mg, from 65 mg to 75 mg, from 65 mg to 70 mg, from 70 mg to 95 mg, from 70 mg to 85 mg, from 70 mg to 75 mg, from 75 mg to 100 mg, from 75 mg to 95 mg, from 75 mg to 90 mg, from 75 mg to 85 mg, from 75 mg to 80 mg, from 80 mg to 95 mg, from 80 mg to 85 mg, from 85 mg to 100 mg, from 85 mg to 90 mg, from 90 mg to 95 mg, from 95 mg to 100 mg, from 80 mg to 89 mg, from 80 mg to 88 mg, from 80 mg to 87 mg, from 80 mg to 86 mg, from 80 mg to 84 mg, from 80 mg to 83 mg, from 80 mg to 82 mg, from 80 mg to 81 mg, from 81 mg to 90 mg, from 82 mg to 89 mg, from 82 mg to 88 mg, from 82 mg to 87 mg, from 82 mg to 86 mg, from 82 mg to 85 mg, from 82 mg to 84 mg, from 82 mg to 83 mg, from 83 mg to 90 mg, from 83 mg to 89 mg, from 83 mg to 88 mg, from 83 mg to 87 mg, from 83 mg to 86 mg, from 83 mg to 85 mg, from 83 mg to 84 mg, from 84 mg to 90 mg, from 84 mg to 89 mg, from 84 mg to 88 mg, from 84 mg to 87 mg, from 84 mg to 86 mg, from 84 mg to 85 mg, from 85 mg to 89 mg, from 85 mg to 88 mg, from 85 mg to 87 mg, from 85 mg to 86 mg, from 86 mg to 90 mg, from 86 mg to 89 mg, from 86 mg to 88 mg, from 86 mg to 87 mg, from 87 mg to 90 mg, from 87 mg to 89 mg, from 87 mg to 88 mg, from 88 mg to 90 mg, from 88 mg to 89 mg, and from 89 mg to 90 mg.

In certain embodiments, the oligomeric compound is present in the dosage unit at an amount that is less than about 300 mg, less than about 295 mg, less than about 290 mg, less than about 285 mg, less than about 280 mg, less than about 275 mg, less than about 270 mg, less than about 265 mg, less than about 260 mg, less than about 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, or less than about 20 mg of an oligomeric compound disclosed herein. The dosage unit may contain more than about 5 mg or more than about 10 mg of the oligomeric compound.

In certain embodiments, the oligomeric compound is present in the dosage unit at an amount that is less than 300 mg, less than 295 mg, less than 290 mg, less than 285 mg, less than 280 mg, less than 275 mg, less than 270 mg, less than 265 mg, less than 260 mg, less than 255 mg, less than 250 mg, less than 245 mg, less than 240 mg, less than 235 mg, less than 230 mg, less than 225 mg, less than 220 mg, less than 215 mg, less than 210 mg, less than 205 mg, less than 200 mg, less than 195 mg, less than 190 mg, less than 185 mg, less than 180 mg, less than 175 mg, less than 170 mg, less than 165 mg, less than 160 mg, less than 150 mg, less than 145 mg, less than 140 mg, less than 135 mg, less than 130 mg, less than 125 mg, less than 120 mg, less than 115 mg, less than 110 mg, less than 105 mg, less than 100 mg, less than 95 mg, less than 90 mg, less than 85 mg, less than 80 mg, less than 75 mg, less than 70 mg, less than 65 mg, less than 60 mg, less than 55 mg, less than 50 mg, less than 45 mg, less than 40 mg, less than 35 mg, less than 30 mg, less than 25 mg, or less than 20 mg of an oligomeric compound disclosed herein. The dosage unit may contain more than 5 mg or more than 10 mg of the oligomeric compound.

In certain embodiments, the oligomeric compound is present in the dosage unit at an amount that is at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 115 mg, at least about 120 mg, at least about 125 mg, at least about 130 mg, at least about 135 mg, at least about 140 mg, at least about 145 mg, or at least about 150 mg of an oligomeric compound disclosed herein.

In certain embodiments, the oligomeric compound is present in the dosage unit at an amount that is at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least about 100 mg, at least 105 mg, at least 115 mg, at least 120 mg, at least 125 mg, at least 130 mg, at least 135 mg, at least 140 mg, at least 145 mg, or at least 150 mg of an oligomeric compound disclosed herein In certain embodiments, pharmaceutical compositions disclosed herein are provided as a volume of a solution comprising an oligomeric compound and a pharmaceutically acceptable carrier or diluent. In certain embodiments, the solution consists or consists essentially of an oligomeric compound disclosed herein and a pharmaceutically acceptable carrier or diluent. The volume may be provided in a suitable container, such as a vial or syringe. Since pharmaceutical compositions disclosed herein may be amenable to self-administration, the syringe may be a pre-filled syringe, an auto-injector syringe, or a combination thereof. For example, a dosage unit described herein may be provided as a fixed volume in a syringe for convenient administration. In certain embodiments, the volume of the solution is 0.1 ml, 0.2 ml, 0.3 ml, 0.4 ml, 0.5 ml, 0.6 ml, 0.7 ml, 0.8 ml, 0.9 ml, 1.0 ml, 1.1 ml, 1.2 ml, 1.3 ml, 1.4 ml, 1.5 ml, 1.6 ml, 1.7 ml, 1.8 ml, 1.9 ml, or 2.0 ml. In certain embodiments, the volume of the solution is about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, or about 2.0 ml. In certain embodiments, the volume of the solution is less than 1.0 ml, less than 1.5 ml, or 2.0 ml. In certain embodiments, the volume of the solution is less than 1.0 ml. A volume of less than 2.0 ml may be useful to reduce or avoid injection pain, adverse events at the injection site, and injection site leakage.

In certain embodiments, pharmaceutical compositions disclosed herein are provided as a volume of a solution comprising an oligomeric compound and a pharmaceutically acceptable carrier or diluent, wherein the volume of the solution is 0.1 ml to 1.5 ml, 0.1 ml to 1.4 ml, 0.1 ml to 1.3 ml, 0.1 ml to 1.2 ml, 0.1 ml to 1.1 ml, 0.1 ml to 1.0 ml, 0.1 ml to 0.9 ml, 0.1 ml to 0.8 ml, 0.1 ml to 0.7 ml, 0.1 ml to 0.6 ml, 0.1 ml to 0.5 ml, 0.1 ml to 0.4 ml, 0.1 ml to 0.3 ml, 0.1 ml to 0.2 ml, 0.2 ml to 1.5 ml, 0.2 ml to 1.4 ml, 0.2 ml to 1.3 ml, 0.2 ml to 1.2 ml, 0.2 ml to 1.1 ml, 0.2 ml to 1.0 ml, 0.2 ml to 0.9 ml, 0.2 ml to 0.8 ml, 0.2 ml to 0.7 ml, 0.2 ml to 0.6 ml, 0.2 ml to 0.5 ml, 0.2 ml to 0.4 ml, 0.2 ml to 0.3 ml, 0.3 ml to 1.5 ml, 0.3 ml to 1.4 ml, 0.3 ml to 1.3 ml, 0.3 ml to 1.2 ml, 0.3 ml to 1.1 ml, 0.3 ml to 1.0 ml, 0.3 ml to 0.9 ml, 0.3 ml to 0.8 ml, 0.3 ml to 0.7 ml, 0.3 ml to 0.6 ml, 0.3 ml to 0.5 ml, 0.3 ml to 0.4 ml, 0.4 ml to 1.5 ml, 0.4 ml to 1.4 ml, 0.4 ml to 1.3 ml, 0.4 ml to 1.2 ml, 0.4 ml to 1.1 ml, 0.4 ml to 1.0 ml, 0.4 ml to 0.9 ml, 0.4 ml to 0.8 ml, 0.4 ml to 0.7 ml, 0.4 ml to 0.6 ml, 0.4 ml to 0.5 ml, 0.5 ml to 1.5 ml, 0.5 ml to 1.4 ml, 0.5 ml to 1.3 ml, 0.5. ml to 1.2 ml, 0.5 ml to 1.1 ml, 0.5 ml to 1.0 ml, 0.5 ml to 0.9 ml, 0.5 ml to 0.8 ml, 0.5 ml to 0.7 ml, 0.5 ml to 0.6 ml, 0.6 ml to 1.5 ml, 0.6 ml to 1.4 ml, 0.6 mo to 1.3 ml, 0.6 ml to 1.2 ml, 0.6 ml to 1.1 ml, 0.6 ml to 1.0 ml, 0.6 ml to 0.9 ml, 0.6 ml to 0.8 ml, 0.6 ml to 0.7 ml, 0.7 ml, to 1.5 ml, 0.7 ml to 1.4 ml, 0.7 ml to 1.3 ml, 0.7 ml to 1.2 ml, 0.7 ml to 1.1 ml, 0.7 ml to 1.0 ml, 0.7 ml to 0.9 ml, 0.7 ml to 0.8 ml, 0.8 ml to 1.5 ml, 0.8 ml to 1.4 ml, 0.8 ml to 1.3 ml, 0.8 ml to 1.2 ml, 0.8 ml to 1.1 ml, 0.8 ml to 1.0 ml. 0.8 ml to 0.9 ml, 0.9 ml, to 1.5 ml, 0.9 ml to 1.4 ml, 0.9 ml to 1.3 ml, 0.9 ml to 1.2 ml, 0.9 ml, to 1.1 ml, 0.9 ml to 1.0 ml, 1.0 ml to 1.5 ml, 1.0 ml to 1.4 ml, 1.0 ml to 1.3 ml, 1.0 ml to 1.2 ml, 1.0 ml to 1.1 ml, 1.1 ml to 1.5 ml, 1.1 ml to 1.4 ml, 1.1 ml to 1.3 ml, 1.1 ml to 1.2 ml, 1.2 ml to 1.5 ml, 1.2 ml to 1.4 ml, 1.2 ml to 1.3 ml, 1.3 ml to 1.5 ml, 1.3 ml to 1.4 ml, 1.4 ml to, and 1.5 ml.

In certain embodiments, pharmaceutical compositions comprise a solution of an oligomeric compound disclosed herein in a pharmaceutically acceptable carrier or diluent at a concentration of 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, or 160 mg/ml. In certain embodiments, pharmaceutical compositions comprise a solution of an oligomeric compound disclosed herein in a pharmaceutically acceptable carrier or diluent at a concentration of about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, about 155 mg/ml, or about 160 mg/ml.

In certain embodiments, pharmaceutical compositions comprise a solution of an oligomeric compound disclosed herein in a pharmaceutically acceptable carrier or diluent at a concentration of 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml, 61 mg/ml, 62 mg/ml, 63 mg/ml, 64 mg/ml, 65 mg/ml, 66 mg/ml, 67 mg/ml, 68 mg/ml, 69 mg/ml, 70 mg/ml, 71 mg/ml, 72 mg/ml, 73 mg/ml, 74 mg/ml, 75 mg/ml, 76 mg/ml, 77 mg/ml, 78 mg/ml, 79 mg/ml, 80 mg/ml, 81 mg/ml, 82 mg/ml, 83 mg/ml, 84 mg/ml, 85 mg/ml, 86 mg/ml, 87 mg/ml, 88 mg/ml, 89 mg/ml, 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, 101 mg/ml, 102 mg/ml, 103 mg/ml, 104 mg/ml, 105 mg/ml, 106 mg/ml, 107 mg/ml, 108 mg/ml, 109 mg/ml, 110 mg/ml, 111 mg/ml, 112 mg/ml, 113 mg/ml, 114 mg/ml, 115 mg/ml, 116 mg/ml, 117 mg/ml, 118 mg/ml, 119 mg/ml, 120 mg/ml, 121 mg/ml, 122 mg/ml, 123 mg/ml, 124 mg/ml, 125 mg/ml, 126 mg/ml, 127 mg/ml, 128 mg/ml, 129 mg/ml, 130 mg/ml, 131 mg/ml, 132 mg/ml, 133 mg/ml, 134 mg/ml, 135 mg/ml, 136 mg/ml, 137 mg/ml, 138 mg/ml, 139 mg/ml, and 140 mg/ml. In certain embodiments, the oligomeric compound is present in the dosage unit at an amount selected from about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 61 mg/ml, about 62 mg/ml, about 63 mg/ml, about 64 mg/ml, about 65 mg/ml, about 66 mg/ml, about 67 mg/ml, about 68 mg/ml, about 69 mg/ml, about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 133 mg/ml, about 134 mg/ml, about 135 mg/ml, about 136 mg/ml, about 137 mg/ml, about 138 mg/ml, about 139 mg/ml, and about 140 mg/ml.

In certain embodiments, pharmaceutical compositions comprise a solution of an oligomeric compound disclosed herein in a pharmaceutically acceptable carrier or diluent at a concentration of 20 mg/ml to 180 mg/ml, 20 mg/ml to 170 mg, 20 mg/ml to 160 mg/ml, 20 mg/ml to 150 mg/ml, 20 mg/ml to 140 mg/ml, 20 mg/ml to 130 mg/ml, 20 mg/ml to 120 mg/ml, 20 mg/ml to 110 mg/ml, 20 mg/ml to 100 mg/ml, 20 mg/ml to 90 mg/ml, 20 mg/ml to 80 mg/ml, 20 mg/ml to 70 mg/ml, 20 mg/ml to 60 mg/ml, 20 mg/ml to 50 mg/ml, 20 mg/ml to 40 mg/ml, 20 mg/ml to 30 mg/ml, 30 mg/ml to 180 mg/ml, 30 mg/ml to 170 mg, 30 mg/ml to 160 mg/ml, 30 mg/ml to 150 mg/ml, 30 mg/ml to 140 mg/ml, 30 mg/ml to 130 mg/ml, 30 mg/ml to 120 mg/ml, 30 mg/ml to 110 mg/ml, 30 mg/ml to 100 mg/ml, 30 mg/ml to 90 mg/ml, 30 mg/ml to 80 mg/ml, 30 mg/ml to 70 mg/ml, 30 mg/ml to 60 mg/ml, 30 mg/ml to 50 mg/ml, 30 mg/ml to 40 mg/ml, 40 mg/ml to 180 mg/ml, 40 mg/ml to 170 mg, 40 mg/ml to 160 mg/ml, 40 mg/ml to 150 mg/ml, 40 mg/ml to 140 mg/ml, 40 mg/ml to 130 mg/ml, 40 mg/ml to 120 mg/ml, 40 mg/ml to 110 mg/ml, 40 mg/ml to 100 mg/ml, 40 mg/ml to 90 mg/ml, 40 mg/ml to 80 mg/ml, 40 mg/ml to 70 mg/ml, 40 mg/ml to 60 mg/ml, 40 mg/ml to 50 mg/ml, 50 mg/ml to 180 mg/ml, 50 mg/ml to 170 mg, 50 mg/ml to 160 mg/ml, 50 mg/ml to 150 mg/ml, 50 mg/ml to 140 mg/ml, 50 mg/ml to 130 mg/ml, 50 mg/ml to 120 mg/ml, 50 mg/ml to 110 mg/ml, 50 mg/ml to 100 mg/ml, 50 mg/ml to 90 mg/ml, 50 mg/ml to 80 mg/ml, 50 mg/ml to 70 mg/ml, 50 mg/ml to 60 mg/ml, 60 mg/ml to 180 mg/ml, 60 mg/ml to 170 mg, 60 mg/ml to 160 mg/ml, 60 mg/ml to 150 mg/ml, 60 mg/ml to 140 mg/ml, 60 mg/ml to 130 mg/ml, 60 mg/ml to 120 mg/ml, 60 mg/ml to 110 mg/ml, 60 mg/ml to 100 mg/ml, 60 mg/ml to 90 mg/ml, 60 mg/ml to 80 mg/ml, 60 mg/ml to 70 mg/ml, 70 mg/ml to 180 mg/ml, 70 mg/ml to 170 mg, 70 mg/ml to 160 mg/ml, 70 mg/ml to 150 mg/ml, 70 mg/ml to 140 mg/ml, 70 mg/ml to 130 mg/ml, 70 mg/ml to 120 mg/ml, 70 mg/ml to 110 mg/ml, 70 mg/ml to 100 mg/ml, 70 mg/ml to 90 mg/ml, 70 mg/ml to 80 mg/ml, 80 mg/ml to 180 mg/ml, 80 mg/ml to 170 mg, 80 mg/ml to 160 mg/ml, 80 mg/ml to 150 mg/ml, 80 mg/ml to 140 mg/ml, 80 mg/ml to 130 mg/ml, 80 mg/ml to 120 mg/ml, 80 mg/ml to 110 mg/ml, 80 mg/ml to 100 mg/ml, 80 mg/ml to 90 mg/ml, 90 mg/ml to 180 mg/ml, 90 mg/ml to 170 mg, 90 mg/ml to 160 mg/ml, 90 mg/ml to 150 mg/ml, 90 mg/ml to 140 mg/ml, 90 mg/ml to 130 mg/ml, 90 mg/ml to 120 mg/ml, 90 mg/ml to 110 mg/ml, 90 mg/ml to 100 mg/ml, 100 mg/ml to 180 mg/ml, 100 mg/ml to 170 mg, 100 mg/ml to 160 mg/ml, 100 mg/ml to 150 mg/ml, 100 mg/ml to 140 mg/ml, 100 mg/ml to 130 mg/ml, 100 mg/ml to 120 mg/ml, 100 mg/ml to 110 mg/ml, 110 mg/ml to 180 mg/ml, 110 mg/ml to 170 mg, 110 mg/ml to 160 mg/ml, 110 mg/ml to 150 mg/ml, 110 mg/ml to 140 mg/ml, 110 mg/ml to 130 mg/ml, 110 mg/ml to 120 mg/ml, 120 mg/ml to 180 mg/ml, 120 mg/ml to 170 mg, 120 mg/ml to 160 mg/ml, 120 mg/ml to 150 mg/ml, 120 mg/ml to 140 mg/ml, 120 mg/ml to 130 mg/ml, 130 mg/ml to 180 mg/ml, 130 mg/ml to 170 mg, 130 mg/ml to 160 mg/ml, 130 mg/ml to 150 mg/ml, 130 mg/ml to 140 mg/ml, 140 mg/ml to 180 mg/ml, 140 mg/ml to 170 mg/ml, 140 mg/ml to 160 mg/ml, 140 mg/ml to 150 mg/ml, 150 mg/ml to 180 mg/ml, 150 mg/ml to 170 mg/ml, 150 mg/ml to 160 mg/ml, 160 mg/ml to 180 mg/ml, 160 mg/ml to 170 mg/ml, or 170 mg/ml to 180 mg/ml.

In certain embodiments, pharmaceutical compositions disclosed herein comprise a sterile lyophilized oligomeric compound that can be reconstituted with a suitable diluent for injection. In certain embodiments, pharmaceutical compositions disclosed herein consist or consist essentially of a sterile lyophilized oligomeric compound that can be reconstituted with a suitable diluent for injection. In certain embodiments, the reconstituted product is administered as a subcutaneous injection after dilution. In certain embodiments, a sterile lyophilized oligomeric compound may consist of the oligomeric compound which has been prepared in distilled water for injection, adjusted to pH 7.0-9.0 with acid or base during preparation, and then lyophilized. The sterile lyophilized oligomeric compound may be packaged in a Type I, clear glass vial (ammonium sulfate-treated), stoppered with a bromobutyl rubber closure and sealed with an aluminum FLIP-OFF® overseal. In certain embodiments, the sterile lyophilized oligomeric compound comprises Compound No. 957943. In certain embodiments, the sterile lyophilized oligomeric compound consists or consists essentially of Compound No. 957943.

VIII. Certain Dosing Regimens

Pharmaceutical compositions disclosed herein may be suitable for acute treatment, temporary treatment, ongoing (prophylactic) treatment, chronic treatment, or a combination thereof. In certain embodiments, methods comprise continually administering a pharmaceutical composition disclosed herein as a prophylactic measure. In certain embodiments, methods comprise temporarily administering a pharmaceutical composition disclosed herein. For example, methods may comprise administering a pharmaceutical composition disclosed herein to an animal within 24 hours of the animal experiencing a thromboembolic event. In certain embodiments, methods comprise administering a pharmaceutical composition disclosed herein to an animal before surgery, during surgery, after surgery, or a combination thereof. In certain embodiments, methods comprise prophylactically administering a pharmaceutical composition disclosed herein on a monthly basis to an animal with a FXI associated disease or condition who is at risk for a thrombotic event. In certain embodiments, the pharmaceutical composition comprises Compound No. 957943. In certain embodiments, the pharmaceutical composition consists or consists essentially of Compound No. 957943 and a pharmaceutically acceptable carrier or diluent.

In certain embodiments, pharmaceutical compositions disclosed herein are useful for treating an animal with a FXI associated disease or condition. In certain embodiments, methods comprise administering a pharmaceutical composition disclosed herein to an animal only once. In certain embodiments, methods comprise administering a pharmaceutical composition disclosed herein to an animal at least twice. In certain embodiments, methods comprise administering a pharmaceutical composition disclosed herein at least 3, at least 4, at least 5, at least 6, at least 8, or at least 10 times. In certain embodiments, methods comprise administering a pharmaceutical composition disclosed herein less than 20 times, less than 15 times, less than 10 times, or less than 5 times.

In certain embodiments, methods comprise administering to an animal a first dose and a second dose of an oligomeric compound disclosed herein. In certain embodiments, the first dose and the second dose are the same. In certain embodiments, the first dose and the second dose are different. In certain embodiments, the first dose is greater than the second dose. In certain embodiments, the second dose is greater than the first dose. In certain embodiments, the first dose is at least 10%, at least 20%, at least 30%, at least 40%, at least 50%, at least 60%, at least 70%, at least 80%, at least 90%, or at least 100% greater than the second dose. In certain embodiments, the second dose is at least 10%, at least 20%, at least 30%, at least 40%, at least 50%, at least 60%, at least 70%, at least 80%, at least 90%, or at least 100% greater than the first dose. In certain embodiments, the first dose and the second dose are separated by 5, 10, 15, 20, 25, 30, 35, or 40 days. In certain embodiments, the first dose and the second dose are separated by 1, 2, 3, 4, 5, or 6 months. In certain embodiments, the first dose and the second dose are separated by 20, 21, 22, 23, 24, 25, 26, 27, 28, 29, 30, 31, 32, 33, 34, 35, 36, 37, 38, 39, or 40 days. In certain embodiments, the first dose and the second dose are separated by 20 to 40 days, 22 to 38 days, 24 to 36 days, 26 to 34 days, 27 to 32 days, 28 to 32 days, or 29 to 31 days. In certain embodiments, the first dose and the second dose are separated by 1, 2, 3, 4, 5, 6, 7, 8, 9, or 10 weeks. In certain embodiments, the first dose and the second dose are separated by 1 to 2 days, 2 to 4 days, 3 to 5 days, 4 to 6 days, 5 to 7 days, 6 to 8 days, 7 to 9 days, 8 to 10 days, 9 to 11 days, 10 to 12 days, 11 to 13 days, 12 to 14 days, 13 to 15 days, 14 to 16 days, 15 to 17 days, 16 to 18 days, 17 to 19 days, or 18 to 20 days.

In certain embodiments, methods comprise administering a pharmaceutical composition disclosed herein monthly or about monthly. In certain embodiments, methods comprise administering a composition disclosed herein to an animal monthly or about monthly for at least two months, at least three months, at least four months, at least five months, or at least six months. In certain embodiments, methods comprise administering a pharmaceutical composition disclosed herein weekly or about weekly. In certain embodiments, methods comprise administering a composition disclosed herein to an animal weekly or about weekly for less than 2 weeks, less than 3 weeks, less than 4 weeks, less than 5 weeks, less than 6 weeks, less than 8 week, less than 12 weeks, less than 16 weeks, or less than 20 weeks.

In certain embodiments, methods comprise administering an oligomeric compound according to a first dosing regimen and subsequently administering the oligomeric compound according to a second dosing regimen. In certain embodiments, the first dosing regimen comprises administering the oligomeric compound at a first dose and at a first frequency and the second dosing regimen comprises administering the oligomeric compound at a second dose and at a second frequency. In certain embodiments, the first frequency is greater than the second frequency. By way of non-limiting example, the first frequency may be greater than once monthly (2 times, 3 times or 4 times per month) and the second frequency may be once monthly. In certain embodiments, the first frequency is less than the second frequency. In certain embodiments, the first dose is greater than the second dose and the first frequency is greater than the second frequency. In certain embodiments, the first dose is less than the second dose and the first frequency is greater than the second frequency. In certain embodiments, the first dose is greater than the second dose and the first frequency is less than the second frequency. In certain embodiments, the first dose is less than the second dose and the first frequency is less than the second frequency. In certain embodiments, the first dose and the second dose are the same, and the first frequency is greater than the second frequency. In certain embodiments, the first dose and the second dose are the same and the first frequency is less than the second frequency. In certain embodiments, the first dose is greater than the second dose, and the first frequency and the second frequency are the same. In certain embodiments, the first dose is less than the second dose and the first frequency and the second frequency are the same. In certain embodiments, at least one of the first frequency and the second frequency are selected from about every 5, about every 10, about every 15, about every 20, about every 25, about every 30, about every 35, or about every 40 days. In certain embodiments, at least one of the first frequency and the second frequency is monthly. In certain embodiments, at least one of the first frequency and the second frequency is weekly. In certain embodiments, the first dose is at least 10%, at least 20%, at least 30%, at least 40%, at least 50%, at least 60%, at least 70%, at least 80%, at least 90%, or at least 100% greater than the second dose. In certain embodiments, the second dose is at least 10%, at least 20%, at least 30%, at least 40%, at least 50%, at least 60%, at least 70%, at least 80%, at least 90%, or at least 100% greater than the first dose.

In certain embodiments, methods comprise a human subject self-administering a pharmaceutical composition disclosed herein. In certain embodiments, methods disclosed herein comprise a human subject self-administering a pharmaceutical composition disclosed herein by subcutaneous injection. In certain embodiments, methods disclosed herein comprise self-administering monthly. In general, pharmaceutical compositions disclosed herein are prepared for subcutaneous administration and a single dose can be provided with a single injection, which makes these pharmaceutical compositions amenable to self-administration. A single injection is possible because oligomeric compounds disclosed herein are highly potent and only a small amount needs to be dissolved in a small volume of a carrier or diluent to provide a dosage unit. Due to the potency and efficacy of oligomeric compounds disclosed herein, in certain embodiments, the animal may only need to receive a dose on a monthly basis to experience therapeutic effects. Such dosing regimens that allow for self-administration on a monthly basis are desirable to patients when compared to dosing regimens of other therapies aimed to treat subjects with FXI associated conditions and diseases, the latter of which may require in-clinic intravenous injection and more frequent administration.

In certain embodiments, administration of a therapeutically effective amount of a pharmaceutical composition as described herein is accompanied by monitoring an amount of a FXI RNA, an amount of a FXI protein, and/or FXI activity in the plasma or serum of an animal, to determine the animal's response to administration of the pharmaceutical composition. An animal's response to administration of the pharmaceutical composition may be used by a physician to determine the amount and duration of therapeutic intervention.

IX. Certain Combination Therapies

In certain embodiments, methods comprise co-administering one or more pharmaceutical compositions described herein with one or more other pharmaceutical agents. In certain embodiments, such one or more other pharmaceutical agents are designed to treat the same disease or condition as the one or more pharmaceutical compositions described herein. In certain embodiments, such one or more other pharmaceutical agents are designed to treat a different disease or condition as the one or more pharmaceutical compositions described herein. In certain embodiments, such one or more other pharmaceutical agents are designed to treat an undesired side effect of one or more pharmaceutical compositions described herein. In certain embodiments, methods comprise co-administering one or more pharmaceutical compositions described herein with one or more other pharmaceutical agents to treat an undesired effect of the other pharmaceutical composition. In certain embodiments, methods comprise co-administering one or more pharmaceutical compositions described herein with one or more other pharmaceutical agents to produce a combinational effect. In certain embodiments, methods comprise co-administering one or more pharmaceutical compositions described herein with one or more other pharmaceutical agents to produce a synergistic effect. In certain embodiments, the pharmaceutical composition comprises Compound No. 957943. In certain embodiments, the pharmaceutical composition consists or consists essentially of Compound No. 957943 and a pharmaceutically acceptable carrier or diluent.

In certain embodiments, methods comprise co-administering one or more pharmaceutical compositions described herein with one or more other pharmaceutical agents at the same time. In certain embodiments, methods comprise co-administering one or more pharmaceutical compositions described herein with one or more other pharmaceutical agents at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include anticoagulant or antiplatelet agents. In certain embodiments, pharmaceutical agents that may be co-administered with a pharmaceutical composition described herein include NSAID/Cyclooxygenase inhibitors, such as, aspirin. In certain embodiments, pharmaceutical agents that may be co-administered with a pharmaceutical composition described herein include adenosine diphosphate (ADP) receptor inhibitors, such as, clopidogrel (PLAVIX) and ticlopidine (TICLID). In certain embodiments, pharmaceutical agents that may be co-administered with a pharmaceutical composition described herein include phosphodiesterase inhibitors, such as, cilostazol (PLETAL). In certain embodiments, pharmaceutical agents that may be co-administered with a pharmaceutical composition described herein include, glycoprotein IIB/IIIA inhibitors, such as, abciximab (REOPRO), eptifibatide (INTEGRILIN), tirofiban (AGGRASTAT), and defibrotide. In certain embodiments, pharmaceutical agents that may be co-administered with a pharmaceutical composition described herein include, adenosine reuptake inhibitors, such as, dipyridamole (PERSANTINE). In certain embodiments, pharmaceutical agents that may be co-administered with a pharmaceutical composition described herein include, but are not limited to, warfarin (and related coumarins), heparin, direct thrombin inhibitors (such as lepirudin, bivalirudin), apixaban, LOVENOX (enoxaparin), and small molecular compounds that interfere directly with the enzymatic action of particular coagulation factors (e.g. rivaroxaban, which interferes with Factor Xa). In certain embodiments, the anticoagulant or antiplatelet agent is administered prior to administration of a pharmaceutical composition described herein. In certain embodiments, the anticoagulant or antiplatelet agent is administered following administration of a pharmaceutical composition described herein. In certain embodiments the anticoagulant or antiplatelet agent is administered at the same time as a pharmaceutical composition described herein. In certain embodiments, the dosage unit of a co-administered anticoagulant or antiplatelet agent is the same as the dosage unit that would be administered if the anticoagulant or antiplatelet agent was administered alone. In certain embodiments the dosage unit of a co-administered anticoagulant or antiplatelet agent is lower than the dosage unit that would be administered if the anticoagulant or antiplatelet agent was administered alone. In certain embodiments the dosage unit of a co-administered anticoagulant or antiplatelet agent is greater than the dosage unit that would be administered if the anticoagulant or antiplatelet agent was administered alone.

In certain embodiments, methods may comprise co-administering a pharmaceutical composition described herein with an anti-inflammatory agent. In certain embodiments, the anti-inflammatory agent modifies a symptom of the inflammatory disease or condition. In certain embodiments, the anti-inflammatory agent modifies progression of the inflammatory disease or condition. Non-limiting examples of inflammatory diseases and conditions are autoimmune diseases (e.g. arthritis, colitis or diabetes), trauma, surgery, sepsis, allergic inflammation, and asthma. Non-limiting examples of anti-inflammatory agents include, but are not limited to, methotrexate, abatacept, infliximab, cyclophosphamide, azathioprine, corticosteroids, cyclosporin A, aminosalicylates, sulfasalazine, hydroxychloroquine, leflunomide, etanercept, efalizumab, 6-mercapto-purine (6-MP), and tumor necrosis factor-alpha (TNFalpha), and other cytokine blockers or antagonists. In certain embodiments, the anti-inflammatory agent comprises a non-steroidal anti-inflammatory drug (NSAID). In certain embodiments, NSAIDs reduce inflammatory reactions in an animal. NSAIDS include, but are not limited to, acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol. In certain embodiments, methods comprise administering a pharmaceutical composition disclosed herein and an anti-inflammatory agent concomitantly or sequentially. In certain embodiments, methods comprise administering the anti-inflammatory agent prior to administering the pharmaceutical composition described herein. In certain embodiments, methods comprise administering the anti-inflammatory agent after administering a pharmaceutical composition described herein. In certain embodiments, methods comprise administering the anti-inflammatory agent and a pharmaceutical composition described herein at the same time. In certain embodiments, the dosage unit of a co-administered anti-inflammatory agent is the same as the dosage unit that would be administered if the anti-inflammatory agent was administered alone. In certain embodiments the dosage unit of a co-administered anti-inflammatory agent is lower than the dosage unit that would be administered if the anti-inflammatory agent was administered alone. In certain embodiments the dosage unit of a co-administered anti-inflammatory agent is greater than the dosage unit that would be administered if the anticoagulant or antiplatelet agent was administered alone.

In certain embodiments, the co-administration of a second pharmaceutical agent enhances the anticoagulant or anti-inflammatory effect of a pharmaceutical composition described herein, such that co-administration of the two results in an anticoagulant or anti-inflammatory effect that is greater than the effect of administering the pharmaceutical composition described herein. In certain embodiments, the co-administration results in anticoagulant or anti-inflammatory effects that are additive of the effects of the two when administered alone. In certain embodiments, the co-administration results in anticoagulant or anti-inflammatory effects that are supra-additive of the effects of the two when administered alone. In certain embodiments, co-administration of a second pharmaceutical agent increases an anti-thrombotic activity or anti-inflammatory activity of the pharmaceutical composition relative to that provided by the pharmaceutical composition alone, without increased bleeding risk.

In certain embodiments, methods comprise co-administering a pharmaceutical composition described herein and an antiplatelet therapy to an animal in need thereof. In certain embodiments, the animal in need thereof may be an animal having a condition selected from thromboembolism, atrial fibrillation, a heart valve disorder, valvular heart disease, stroke, coronary artery disease (CAD), and a mechanical heart valve, and a combination thereof. In certain embodiments, administering a pharmaceutical composition described herein in combination with an antiplatelet therapy results in little to no detectable increase in risk of bleeding as compared to antiplatelet therapy alone. In certain embodiments, the risk profile or risk indications are unchanged over antiplatelet therapy alone.

In certain embodiments, methods comprise administering a pharmaceutical composition described herein to a dialysis patient, including but not limited to an animal with end stage renal disease (ESRD) or chronic kidney disease (CKD), wherein the animal is co-administered at least one pharmaceutical agent selected from heparin, erythropoietin, darbopoetin, iron, Vitamin D or analogues thereof, phosphate binders, and a combination thereof. In certain embodiments, the animal receives dialysis. In certain embodiments, the pharmaceutical agent is administered at a dose that does not differ from a comparative dose that would be prescribed in the absence of administering the pharmaceutical composition.

X. Certain Indications

In certain embodiments, methods comprise administering a pharmaceutical composition described herein to an animal with a thromboembolic condition. In certain embodiments, methods comprise administering a pharmaceutical composition described herein to an animal at risk for a thromboembolic condition. Thromboembolic conditions include, but are not limited to, thrombosis, embolism, thromboembolism, infarct, deep vein thrombosis, pulmonary embolism, myocardial infarction, stroke, and coronary artery disease (CAD). Risk factors for developing a thromboembolic condition include, a genetic, situational, disease, or environmental factor, or a combination thereof. In certain embodiments, such factors may include, but are not limited to, surgery, cancer, malignancy, pregnancy, older age, use of oral contraceptives, immobility, including travel-related immobility, sepsis, having a mechanical heart valve, valvular heart disease, atrial fibrillation, atherosclerosis atrial fibrillation, genetic predisposition, antiphospholipid syndrome, and inherited or acquired prothrombotic clotting disorders, such as Factor V Leiden. Identifying an animal at risk for developing a thromboembolic condition may be accomplished by any method including evaluating an animal's medical history and standard clinical tests or assessments. In certain embodiments, the pharmaceutical composition comprises Compound No. 957943. In certain embodiments, the pharmaceutical composition consists or consists essentially of Compound No. 957943 and a pharmaceutically acceptable carrier or diluent.

In certain embodiments, methods comprise administering a pharmaceutical composition described herein to an animal with a disease or condition of the kidney. In certain embodiments, the condition is nephrotoxic drug exposure. In certain embodiments the condition is a genetic or developmental malformation of the kidney, such as that caused by a cystic kidney disease. Non-limiting examples of cystic kidney diseases are autosomal dominant polycystic kidney disease, autosomal recessive polycystic kidney disease, medullary cystic kidney disease and glomerulocystic kidney disease. In certain embodiments, the condition is primary or secondary vesicoureteral reflux. In certain embodiments, the condition is a urethral stricture. In certain embodiments, the condition is a primary or secondary nephrotic syndrome. In certain embodiments, the condition is a primary or secondary glomerulonephritis. In certain embodiments, the condition is lupus nephritis, giant cell arteritis, chronic urinary outflow obstruction, or nephrolithiasis. In certain embodiments, the condition is kidney failure. In certain embodiments, the disease is chronic kidney disease (CKD). In certain embodiments, the disease is end stage renal disease (ESRD). In certain embodiments, the animal is a human subject at risk for CKD or ESRD. Subjects at risk for CKD or ESRD include human subjects who smoke, are obese (e.g., body mass index greater than 30), have hypertension, have diabetes mellitus, receive dialysis, or a combination thereof. In certain embodiments, the human subject is a dialysis patient. The dialysis patient may have previously received dialysis, undergoes dialysis, will receive dialysis, or a combination thereof. In certain embodiments, the human subject is a dialysis patient with ESRD or CKD. Dialysis patients may be at high risk for thrombotic events. Dialysis patients may also be at risk for bleeding events. For example, blood vessels of ESRD patients may be compromised resulting in an increased risk of a thrombotic event or a hemorrhagic event. Thus, dialysis patients may benefit from therapeutic agents that are anti-coagulatory, but do not increase risk of bleeding, such as pharmaceutical compositions described herein. In certain embodiments, the pharmaceutical composition comprises Compound No. 957943. In certain embodiments, the pharmaceutical composition consists or consists essentially of Compound No. 957943 and a pharmaceutically acceptable carrier or diluent.

In certain embodiments, methods comprise administering a pharmaceutical composition described herein to an animal who has been identified as in need of anticoagulation therapy. Examples of such animals include, but are not limited to, those undergoing major orthopedic surgery (e.g., hip/knee replacement or hip fracture surgery) and patients in need of chronic treatment, such as those suffering from arterial fibrillation to prevent stroke. In certain embodiments, methods comprise administering an oligomeric compound described herein, thereby prophylactically reducing a FXI RNA or protein in an animal. Certain embodiments include treating an animal in need thereof by administering to an animal a therapeutically effective amount of a pharmaceutical composition comprising a modified oligonucleotide complementary to a nucleic acid encoding human FXI. In certain embodiments, the pharmaceutical composition comprises Compound No. 957943. In certain embodiments, the pharmaceutical composition consists or consists essentially of Compound No. 957943 and a pharmaceutically acceptable carrier or diluent.

In certain embodiments, methods comprise administering one or more pharmaceutical compositions described herein to an animal who has an inflammatory condition. In certain embodiments, an inflammatory condition means any disease or condition related to an inflammatory response to injury or stimulus characterized by clinical signs of increased redness (rubor), temperature (calor), swelling (tumor), pain (dolor) and/or loss of function (functio laesa) in a tissue. In certain embodiments, examples of such diseases, disorders, and conditions include, but are not limited to, arthritis, colitis, diabetes, sepsis, allergic inflammation, asthma, immunoproliferative disease, antiphospholipid syndrome, graft-related disorder, trauma, autoimmune diseases, vasculitis, or surgery-related disorders. Examples of arthritis include, but are not limited to, rheumatoid arthritis, juvenile rheumatoid arthritis, arthritis uratica, gout, chronic polyarthritis, periarthritis humeroscapularis, cervical arthritis, lumbosacral arthritis, osteoarthritis, psoriatic arthritis, enteropathic arthritis and ankylosing spondylitis. Examples of colitis include, but are not limited to, ulcerative colitis, Inflammatory Bowel Disease (IBD) and Crohn's Disease. Examples of graft-related disorders include, but are not limited to, graft versus host disease (GVHD), disorders associated with graft transplantation rejection, chronic rejection, and tissue or cell allografts or xenografts. Examples of immunoproliferative diseases include, but are not limited to, cancers (e.g., lung cancers) and benign hyperplasias. Examples of autoimmune diseases include, but are not limited to, lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, rheumatic diseases (e.g., rheumatoid arthritis), polymyositis, scleroderma, psoriasis, and mixed connective tissue disease. In certain embodiments, such animal has been identified as at risk for developing an inflammatory condition. In certain embodiments, the animal has a protein C deficiency or a protein S deficiency. In certain embodiments, such animals are at risk of developing an inflammatory condition due to various genetic, situational, disease, or environmental factors. In certain embodiments, such factors may include, but are not limited to, familial history of inflammatory disease such as diabetes, colitis or arthritis, exposure to allergens such as pollen, exposure to material such as asbestos or environmental pollutants. Identifying an animal at risk for developing an inflammatory condition may be accomplished by any method including evaluating the animal's medical history and standard clinical tests or assessments. In certain embodiments, the animal has been identified as in need of anti-inflammatory therapy. Examples of such animals include, but are not limited to, those animals who have been diagnosed with an inflammatory condition and those animals who have a risk factor for developing an inflammatory condition. In certain embodiments, the pharmaceutical composition comprises Compound No. 957943. In certain embodiments, the pharmaceutical composition consists or consists essentially of Compound No. 957943 and a pharmaceutically acceptable carrier or diluent.

XI. Potency and Efficacy

In certain embodiments, pharmaceutical compositions disclosed herein are sufficiently potent to reduce FXI RNA, FXI protein, FXI activity, or a combination thereof in an animal. In certain embodiments, a single dosage unit of a pharmaceutical composition disclosed herein is sufficiently potent to reduce FXI RNA, FXI protein, FXI activity, or a combination thereof in an animal. In certain embodiments, potency can be determined by determining a first amount of a FXI RNA, FXI protein, or FXI activity before administering a pharmaceutical composition comprising an oligomeric compound disclosed herein and determining a second amount of the FXI RNA, FXI protein, or FXI activity at a relative timepoint after administering, and comparing the first amount to the second amount. In certain embodiments, the relevant timepoint after administering is 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the relevant timepoint after administering is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In certain embodiments, the relevant timepoint after administering is greater than 30 days. In certain embodiments, the relevant timepoint after administering is after a final dosage unit of the oligomeric compound is administered to an animal. In certain embodiments, the relevant timepoint is after an intermediate dosage unit of the oligomeric compound is administered to the animal. An amount of reduction in the second amount relative to the first amount may serve as an indication of potency. The amount of reduction may be expressed as percent reduction as demonstrated herein.

In certain embodiments, methods comprise reducing a FXI RNA in an animal. In certain embodiments, methods comprise reducing a FXI protein in an animal. FXI is expressed in the liver but secreted to the blood where it is active. Thus, FXI RNA, FXI protein, and FXI activity levels may be measured in plasma or serum. In certain embodiments, methods disclosed herein reduce a FXI RNA, a FXI protein, and/or a FXI activity. FXI activity may cause a change in blood clotting activity in the animal. The FXI activity may cause a reduction in blood clotting activity in the animal. Blood clotting may be measured by a standard test, for example, but not limited to, activated partial thromboplastin time (aPTT) test, prothrombin time (PT) test, thrombin time (TCT), bleeding time, or presence of D-dimer in a blood sample of the animal. In certain embodiments, a FXI RNA is reduced in a liver or in plasma/serum of an animal by 1-100%, or a range defined by any two of these values. In certain embodiments, a FXI RNA, FXI protein, or FXI activity is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In certain embodiments, pharmaceutical compositions and methods described herein are efficacious because they improve a cardiovascular outcome in an animal. In certain embodiments, pharmaceutical compositions and methods improve a cardiovascular outcome in a population treated with a pharmaceutical composition disclosed herein and/or according to a method disclosed herein relative to a population that is not treated with the pharmaceutical composition and/or according to the method. In certain embodiments, the improved cardiovascular outcome is a reduction of the risk of developing a thromboembolic condition. In certain embodiments, the improved cardiovascular outcome is a reduction in the occurrence of one or more major cardiovascular events. Cardiovascular events include, but are not limited to, death, myocardial infarction, reinfarction, stroke, cardiogenic shock, pulmonary edema, cardiac arrest, and atrial dysrhythmia. In certain embodiments, the cardiovascular event is an ischemic stroke. In certain embodiments, the cardiovascular event is a peripheral arterial ischemic event, e.g., amputation ischemia or limb ischemia. In certain embodiments, the improved cardiovascular outcome is evidenced by improved carotid intimal media thickness. In certain embodiments, improved carotid intimal media thickness is a decrease in thickness. In certain such embodiments, improved carotid intimal media thickness is a prevention an increase of intimal media thickness.

XII. Certain Comparator Compositions

In certain embodiments, Compound No: 416858, a 5-10-5 MOE gapmer, having a sequence of (from 5' to 3') ACGGCATTGGTGCACAGTTT (incorporated herein as SEQ ID NO: 3), wherein each internucleoside linkage is a phosphorothioate internucleoside linkage, each cytosine is a 5'-methyl cytosine, and each of nucleosides 1-5 and 16-20 (from 5' to 3') comprise a 2'-MOE modified sugar, which was previously described in WO 2010/045509, incorporated herein by reference, is a comparator compound. Compound No. 416858 was selected as a comparator compound because it was selected for clinical development and was confirmed to be tolerable in phase 1 clinical trials, and is currently in phase 2 clinicals. See, e.g., BETHUNE, et al, "Pharmacokinetics and Pharmacodynamics of Ionis-FXI$_{Rx}$, an Antisense Inhibitor of Factor XI, in Patients with End-Stage Renal Disease on Hemodialysis," *Blood* (2017)130: 1116; BÜLLER, et al, "Factor XI antisense oligonucleotide for prevention of venous thrombosis." *N Engl J Med* (2015) 372(3): 232-240 and LIU, et al, "ISIS-FXI$_{Rx}$, A Novel and Specific Antisense Inhibitor of Factor XI, Caused Significant Reduction in FXI Antigen and Activity and Increased aPTT without Causing Bleeding in Healthy Volunteers" *Blood* (2011)118:209.

In certain embodiments, Compound No. 957943 described herein, is superior relative to Compound No. 416858 because it demonstrates one or more improved properties, such as, potency and tolerability. Compound No. 957943 may be dosed at lower amounts than Compound No. 416858. Compound No. 957943 may be dosed less frequently than Compound No. 416858. For example, as provided in Example 5, below, in the phase 1 human clinical trial for Compound No. 957943, individuals were administered Compound No. 957943 once every four weeks.

For example, as provided in Example 1 (hereinbelow), Compound No. 957943 demonstrated an $ED_{50}$ for FXI RNA reduction of 0.41 mg/kg in hFXI transgenic mice. Comparator Compound No. 416858 demonstrated an $ED_{50}$ for RNA reduction of 8.35 mg/kg in the same study. Therefore, Compound No. 957943 is demonstrably more potent than comparator Compound No. 416858 in hFXI transgenic mice for RNA reduction.

For example, as provided in Example 1 (hereinbelow), Compound No. 957943 demonstrated greater FXI protein reduction at each dosage level as compared to Compound No. 416858 when Compound No. 957943 was dosed at one-tenth the amount of Compound No. 416858.

For example, as provided in Example 2 (hereinbelow), Compound No. 957943 demonstrated lack of platelet reduction in cynomolgus monkeys. Also, as provided in Example 4 (hereinbelow), Compound No. 957943 demonstrated lack of platelet reduction in human subjects.

For example, as provided in Example 3 (hereinbelow), Compound No. 957943 demonstrated an $EC_{50}$ for FXI RNA reduction of 0.02 μM with primer probe set RTS2966 and 0.03 μM with primer probe set RTS36807 in HepatoPac® cells. Comparator Compound No. 416858 demonstrated an $EC_{50}$ for FXI RNA reduction of 0.98 μM with primer probe set RTS2966 and 1.07 μM with primer probe set RTS36807 in the same study. Therefore, Compound No. 957943 is demonstrably more potent than comparator Compound No. 416858 in this study.

For example, as provided in Examples 4 and 5 (provided hereinbelow) Compound No. 957943 effectively reduced plasma concentrations of FXI protein and FXI activity in human subjects at all doses and time points tested when administered weekly and monthly.

XIII. Certain Compositions

1. Compound No. 957943

In certain embodiments, Compound No. 957943 is characterized as an oligomeric compound consisting of a conjugate group and a modified oligonucleotide, wherein the conjugate group is a THA-GalNAc$_3$ that is directly attached to the 5' end of the modified oligonucleotide through a phosphodiester linkage, (THA-GalNAc$_3$)o; wherein (THA-GalNAc$_3$)o is represented by the following structure:

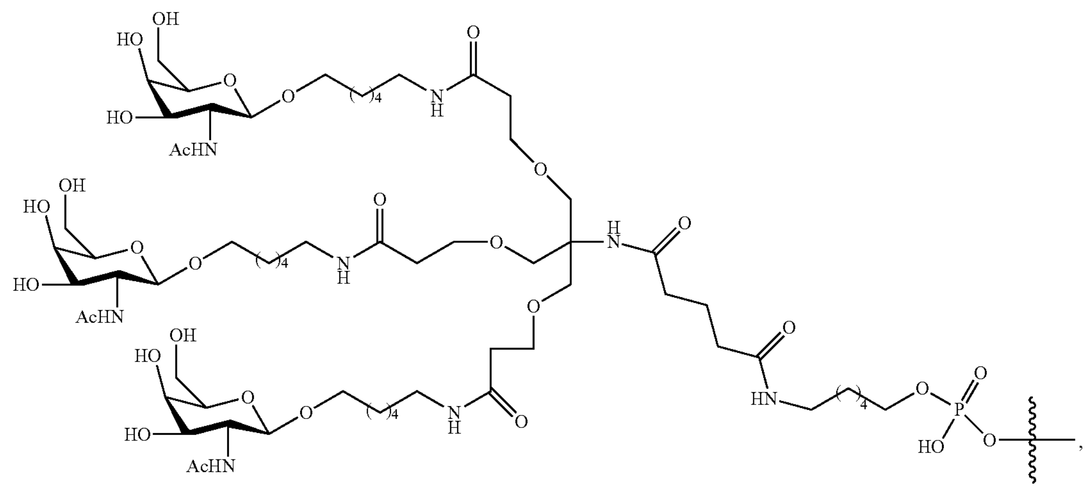

and wherein the modified oligonucleotide is a 5-10-5 MOE gapmer, having a sequence of (from 5' to 3') ACGGCATTGGTGCACAGTTT (incorporated herein as SEQ ID NO: 3), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5'-methyl cytosine.

In certain embodiments, Compound No. 957943 is characterized by the following chemical notation: (THA-GalNAc$_3$)o Aes mCeo Geo Geo mCeo Ads Tds Tds Gds Gds Tds Gds mCds Ads mCds Aeo Geo Tes Tes Te; wherein, (THA-GalNAc3)o is represented by the following structure:

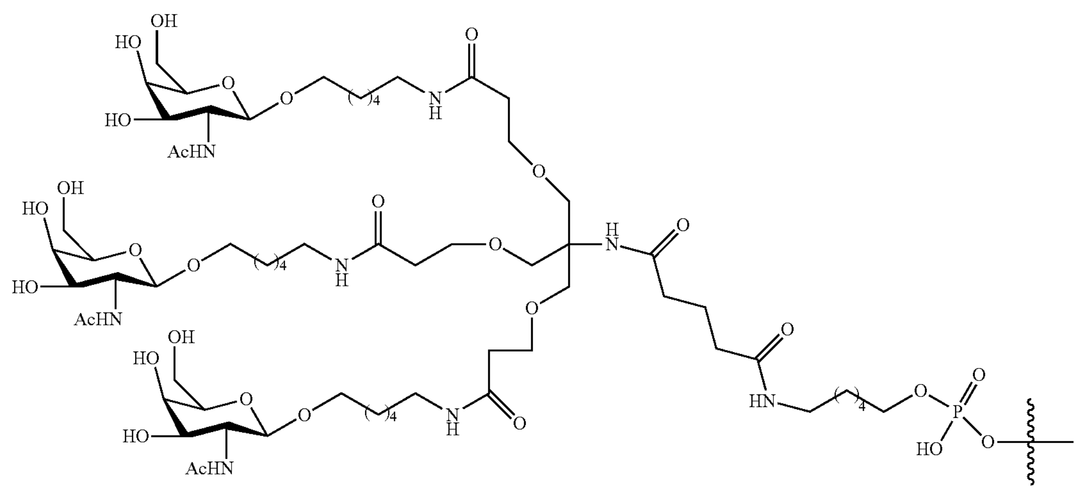
and wherein,
A=an adenine nucleobase,
mC=a 5'-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.
In certain embodiments, Compound No. 957943 is represented by the following chemical structure:

Structure 1. Compound No. 957943
(SEQ ID NO: 3)
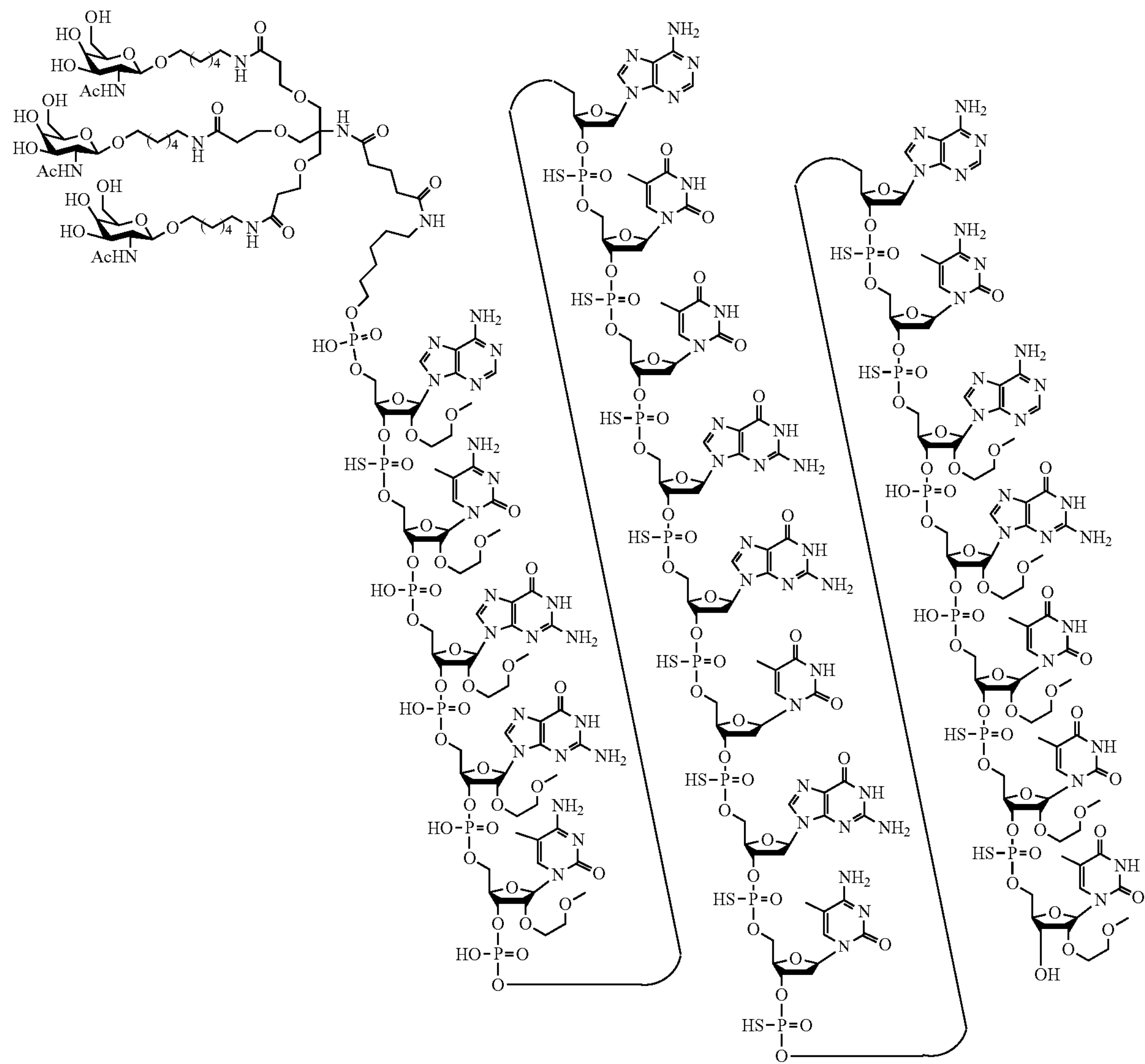

In certain embodiments, the sodium salt of Compound No. 957943 is represented by the following chemical structure:

Structure 2. Sodium salt of Compound No. 957943

(SEQ ID NO: 3)

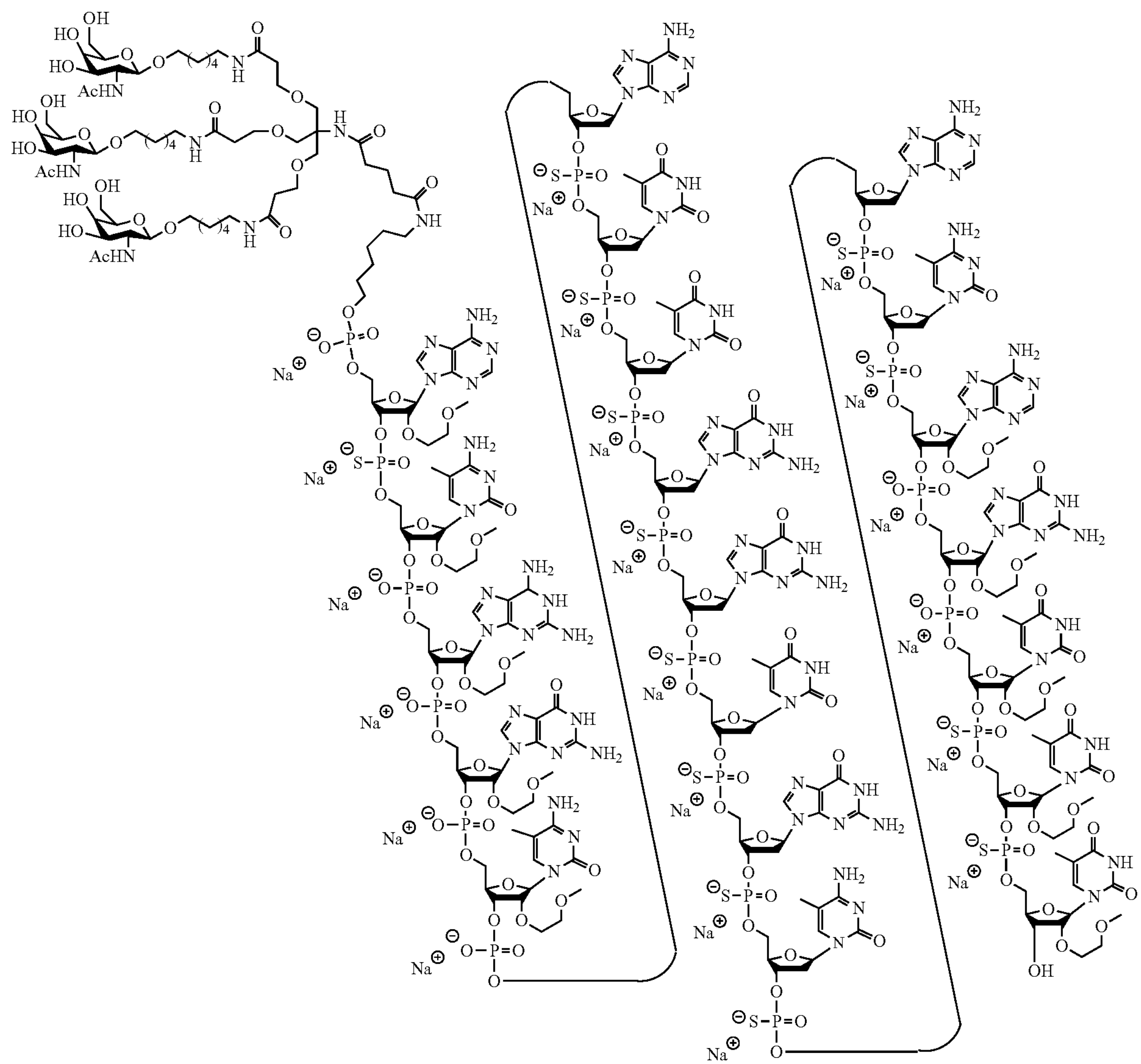

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Potency of Compound No. 416858 and Compound No. 957943 in Transgenic Mice Oligomeric compounds No. 416858 and 957943 were tested in a Factor XI PAC transgenic mouse model which uses bacterial PI artificial chromosome (PAC) containing the entire WT human Factor XI gene. The mouse model was generated from a human FXI gene fragment containing the entire 24 Kb human FXI transgene as well as 9 Kb upstream and 6 Kb downstream. The gene fragment was microinjected into the pronucleus of fertilized mouse eggs, and the complete BAC integration of the transgene was confirmed by PCR using human specific primer probe sets. The established founder has predominate liver expression of human FXI RNA and circulating human FXI in plasma.

TABLE 1

Oligomeric compounds complementary to human FXI

| Compound Number | 5'modification | Chemistry notation (5'to 3') | SEQ ID NO: |
|---|---|---|---|
| 416858 | none | $A_{es}{}^{m}C_{es}G_{es}G_{es}{}^{m}C_{es}A_{ds}T_{ds}T_{ds}G_{ds}G_{ds}T_{ds}G_{ds}{}^{m}C_{ds}A_{ds}{}^{m}C_{ds}A_{es}G_{es}T_{es}T_{es}T_{e}$ | 3 |
| 957943 | (THA-GalNAc$_3$)o | $A_{es}{}^{m}C_{eo}G_{eo}G_{eo}{}^{m}C_{eo}A_{ds}T_{ds}T_{ds}G_{ds}G_{ds}T_{ds}G_{ds}{}^{m}C_{ds}A_{ds}{}^{m}C_{ds}A_{eo}G_{eo}T_{es}T_{es}T_{e}$ | 3 |

Subscripts: 'd'represents a 2'-deoxyribose sugar; 'e'represents a 2'-MOE modified sugar. All cytosine residues throughout each gapmer are 5'-methyl cytosines, represented by a superscript 'm'. The internucleoside linkages are represented by subscript 'o'or 's', wherein 'o'represents a phosphodiester internucleoside linkage and 's'represents a phosphorothioate internucleoside linkage.

Treatment

Transgenic hFXI mice were divided into groups of 8 mice each, 4 male and 4 female. Five groups of mice were administered 1.0, 2.5, 5.0, 10.0, or 25.0 mg/kg of Compound No. 416858. Five groups of mice were administered 0.1, 0.25, 0.50, 1.00, or 2.50 mg/kg of Compound No. 957943. Mice were administered oligomeric compounds twice a week for two weeks by subcutaneous injection and sacrificed at the end of the study. A group of 6 mice (3 male and 3 female) was administered PBS twice a week for two weeks and sacrificed at the end of the study. The PBS-injected group served as the control group to which oligomeric compound treated groups were compared.

RNA Analysis

After two weeks, mice were sacrificed and RNA was extracted from liver for real-time PCR analysis of measurement of RNA expression of human Factor XI using primer probe set RTS2965 (forward sequence ACGGTGTTTGCAGACAGCAA, designated herein as SEQ ID NO: 4; reverse sequence TGCAGATTCGGCCACAGA, designated herein as SEQ ID NO: 5; probe sequence ACAGTGTCATGGCTCCCGATGCTTTT, designated herein as SEQ ID NO: 6). Results are presented as percent change of RNA, relative to PBS control, normalized to total RNA levels determined with Ribogreen®. Compound No. 416858 achieved an $ED_{50}$ of 8.35 mg/kg and Compound No. 957943 achieved an $ED_{50}$ of 0.41 mg/kg. $ED_{50}$ values reported in Table 2 are an average of $ED_{50}$ values that were calculated based on data from a single daily dosing.

TABLE 2

Percent reduction of human Factor XI RNA in female transgenic mice

| Compound No. | Daily Dose (mg/kg/dose) | Liver Factor XI (% control) | $ED_{50}$ (mg/kg) |
|---|---|---|---|
| PBS | — | 100 | |
| 416858 | 1.0 | 80 | 8.35 mg/kg |
| | 2.5 | 85 | |
| | 5.0 | 79 | |
| | 10.0 | 40 | |
| | 25.0 | 28 | |
| 957943 | 0.10 | 74 | 0.41 mg/kg |
| | 0.25 | 62 | |
| | 0.50 | 56 | |
| | 1.00 | 27 | |
| | 2.50 | 7 | |

Protein Analysis

Reduction of FXI plasma protein was demonstrated by ELISA. At the end of the study, blood was collected under anesthesia via cardiac puncture into sample tubes coated with citric acid. Blood was centrifuged at 4000 g for 15 minutes and platelet poor plasma was collected and stored at −80° C. prior to analysis. Pooled plasma samples from all groups were analyzed by VisuLize FXI Antigen Kit (Affinity Biologicals INC). Data are presented as the mean of the individual samples.

TABLE 3

Percent reduction of human Factor XI protein in the plasma of transgenic mice

| Compound No. | Dose (mg/kg/dose) | Plasma Factor XI (% control) |
|---|---|---|
| PBS | — | 100 |
| 416858 | 1.0 | 81 |
| | 2.5 | 82 |
| | 5.0 | 71 |
| | 10.0 | 56 |
| | 25.0 | 30 |
| 957943 | 0.1 | 77 |
| | 0.25 | 72 |

TABLE 3-continued

| Percent reduction of human Factor XI protein in the plasma of transgenic mice | | |
|---|---|---|
| Compound No. | Dose (mg/kg/dose) | Plasma Factor XI (% control) |
| | 0.50 | 59 |
| | 1.00 | 33 |
| | 2.50 | 21 |

Example 2: Tolerability of Oligomeric Compounds Complementary to Human Factor XI in Cynomolgus Monkeys Compound No. 416858 was administered to cynomolgus monkeys at 4, 8, 12, and 40 mg/kg/week by subcutaneous injection for 13 weeks, as described in Husam, et. al., "Antisense inhibition of coagulation factor XI prolongs APTT without increased bleeding risk in cynomolgus monkeys", *Blood,* 2012, 119: 2401-2408, incorporated by reference herein in its entirety.

Compound No. 957943 was administered to groups of 14-18 cynomolgus monkeys, half male and half female, at 1, 6, and 25 mg/kg once a month or 1.5 mg/kg weekly by subcutaneous injection. Platelet levels were measured during routine CBC measurements.

TABLE 4

| Platelet Counts in Cynomolgus Monkeys after Treatment with Compound No. 416858, measured at day 93 | | | | | |
|---|---|---|---|---|---|
| Dose (weekly) | none (PBS) | 4 mg/kg | 8 mg/kg | 12 mg/kg | 40 mg/kg |
| Platelets (× $10^3$/μL) | 506 | 516 | 452 | 404 | 357 |

TABLE 5

| Platelet Counts in Cynomolgus Monkeys after treatment with Compound No. 957943 for up to 87 days | | | | | |
|---|---|---|---|---|---|
| Dose | none (PBS) | 1.5 mg/kg, weekly | 1 mg/kg, monthly | 6 mg/kg, monthly | 25 mg/kg, monthly |
| Platelets (× $10^3$/μL) baseline (9 days pre-treatment) | 367 | 380 | 355 | 398 | 409 |
| Platelets (× $10^3$/μL) day 31 | 378 | 366 | 347 | 372 | 370 |
| Platelets (× $10^3$/μL) day 59 | 381 | 386 | 359 | 391 | 396 |
| Platelets (× $10^3$/μL) day 87 | 373 | 369 | 352 | 378 | 379 |

Example 3: Potency of Compound No. 416858 and Compound No. 957943 In Vitro in HepatoPac® Cells The HepatoPac® kit is a commercially-available in vitro liver model system available from BIOIVT that consists of micropatterned hepatocyte "islands" co-cultured with supportive stromal cells. A 96-well HepatoPac plate was equilibrated for 48 hours at 37° C. and 10% $CO_2$ in fresh maintenance medium prior to treatment. Oligomeric compounds were diluted into maintenance medium at 0.0002, 0.0020, 0.0200, 0.2000, 2.0000, or 20.0000 μM for 48 hours. After 48 hours, medium was replaced with fresh maintenance medium without additional compound. Cell lysates were collected at 96 hours post compound addition and analyzed by RT-PCR using primer probe set RTS2966 (forward sequence CAGCCTGGAGCATCGTAACA, designated herein as SEQ ID NO: 7; reverse sequence TTTATCGAGCTTCGTTATTCTGGTT designated herein as SEQ ID NO: 8; probe sequence TTGTCTACTGAAGCACACCCAAACAGGGA designated herein as SEQ ID NO. 9). $IC_{50}$ was calculated using a linear regression on a log/linear plot of the data in excel. Compound No. 416858 exhibited an $IC_{50}$ of 0.98 μM and Compound No. 957943 exhibited an $IC_{50}$ of 0.02 μM. Data was confirmed using a second primer probe set RTS36807 (forward sequence GCCAGGTAGTCTGCACTTAC, designated herein as SEQ ID NO: 10; reverse sequence GTCCTATTCACTCTTGGCAGT, designated herein as SEQ ID NO. 11; probe sequence CCACCCGATGGTTTACTTGTGTCCT, designated herein as SEQ ID No. 12). $IC_{50}$ was calculated as described above. Compound No. 416858 exhibited an $IC_{50}$ of 1.07 μM and Compound No. 957943 exhibited an $IC_{50}$ of 0.03 μM.

TABLE 6

| Percent reduction of human Factor XI mRNA in Hepatopac ® cells | | | | | |
|---|---|---|---|---|---|
| Compound No. | Dose (μM) | Factor XI (% control) RTS2966 | $IC_{50}$ (μM) RTS2966 | Factor XI (% control) RTS36807 | $IC_{50}$ (μM) RTS36807 |
| PBS | — | 100 | | 100 | |
| 416858 | 0.0002 | 104 | 0.98 | 125 | 1.07 |
| | 0.0020 | 107 | | 110 | |
| | 0.0200 | 102 | | 109 | |
| | 0.2000 | 93 | | 100 | |
| | 2.0000 | 32 | | 28 | |
| | 20.0000 | 8 | | 6 | |
| 957943 | 0.0002 | 91 | 0.02 | 101 | 0.03 |
| | 0.0020 | 64 | | 56 | |
| | 0.0200 | 62 | | 63 | |
| | 0.2000 | 18 | | 20 | |

TABLE 6-continued

| Percent reduction of human Factor XI mRNA in Hepatopac ® cells | | | | | |
|---|---|---|---|---|---|
| Compound No. | Dose (μM) | Factor XI (% control) RTS2966 | $IC_{50}$ (μM) RTS2966 | Factor XI (% control) RTS36807 | $IC_{50}$ (μM) RTS36807 |
| | 2.0000 | 9 | | 7 | |
| | 20.0000 | 11 | | 11 | |

Example 4: Phase 1 Human Clinical Trial with Compound No. 957943—Single Dose Cohorts Varying doses of Compound No. 957943 were evaluated in a randomized, double-blind, placebo-controlled study to evaluate the safety, tolerability, pharmacokinetics and pharmacodynamics of single doses of Compound No. 957943 in healthy volunteers.

Subjects received doses according to Table 7. Four cohorts of healthy volunteers were enrolled sequentially and randomized to receive Compound No. 957943 or placebo by subcutaneous injection.

TABLE 7

Single Dose Cohorts

| Treatment Assignment | Healthy Volunteers | Doses | Total Dose of Compound No. 957943 |
|---|---|---|---|
| Placebo | 8 | 1 | 0 mg |
| A | 6 | 1 | 40 mg |
| B | 6 | 1 | 60 mg |
| C | 6 | 1 | 80 mg |
| D | 6 | 1 | 120 mg |

FXI protein concentrations in plasma were measured at baseline, 8 days after treatment, 15 days after treatment, 30 days after treatment and 60 days after treatment. Plasma FXI protein concentrations were measured by a standard ELISA assay. To assay FXI activity, plasma samples from test subjects were added to plasma samples that were immunodepleted of FXI and clotting time for each sample was assayed. Clotting time is proportional to the level of FXI activity in the patient plasma since all other factors are initially present at normal levels. The FXI content of the patient plasma was determined from a reference curve prepared with the FXI deficient plasma and varying dilutions of standard human plasma. The reference value, which was derived from control plasma, was 1.0 unit per milliliter.

Figure 1B:
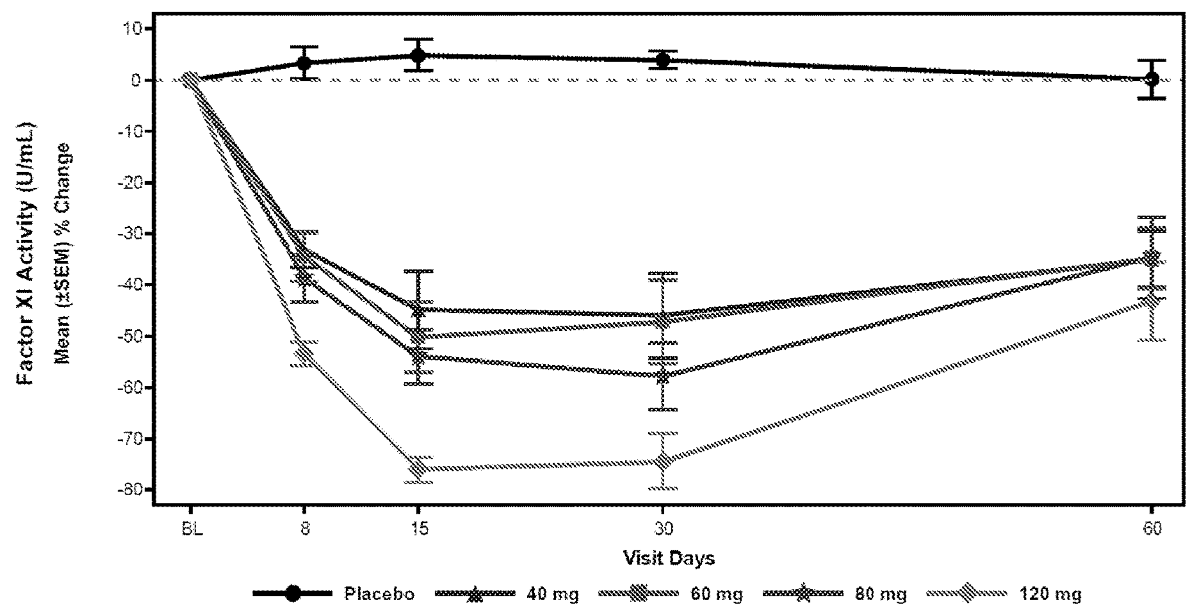
Figure 2A:
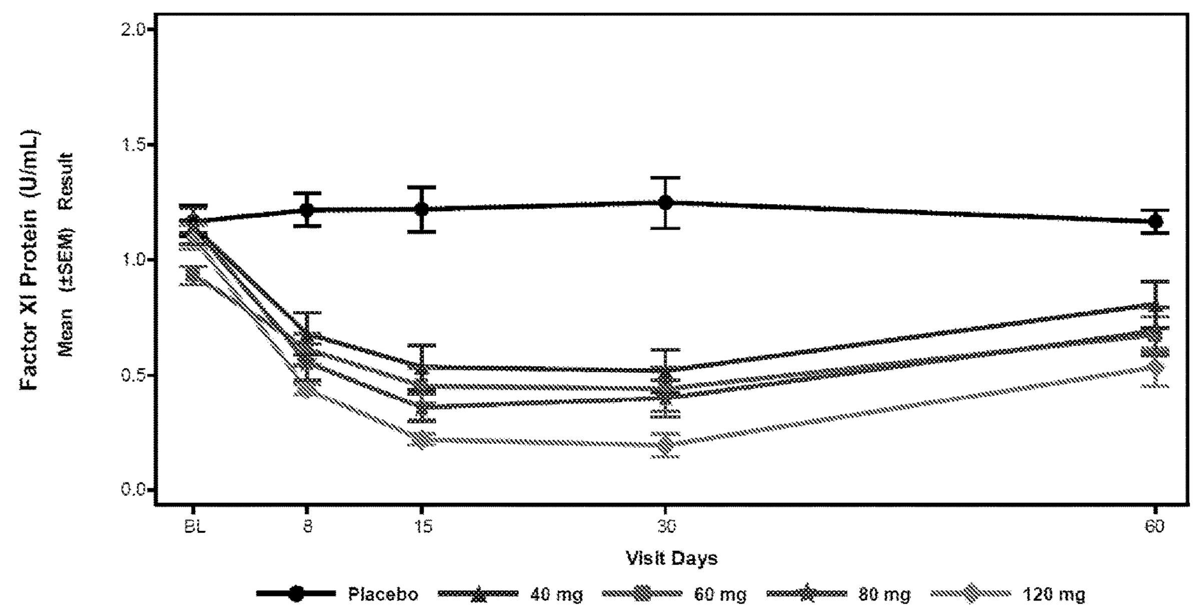
FIGS. 2A and 2B show pharmacodynamic results over time for single dose cohorts receiving Compound No. 957943, as measured by ELISA.
Figure 2B:
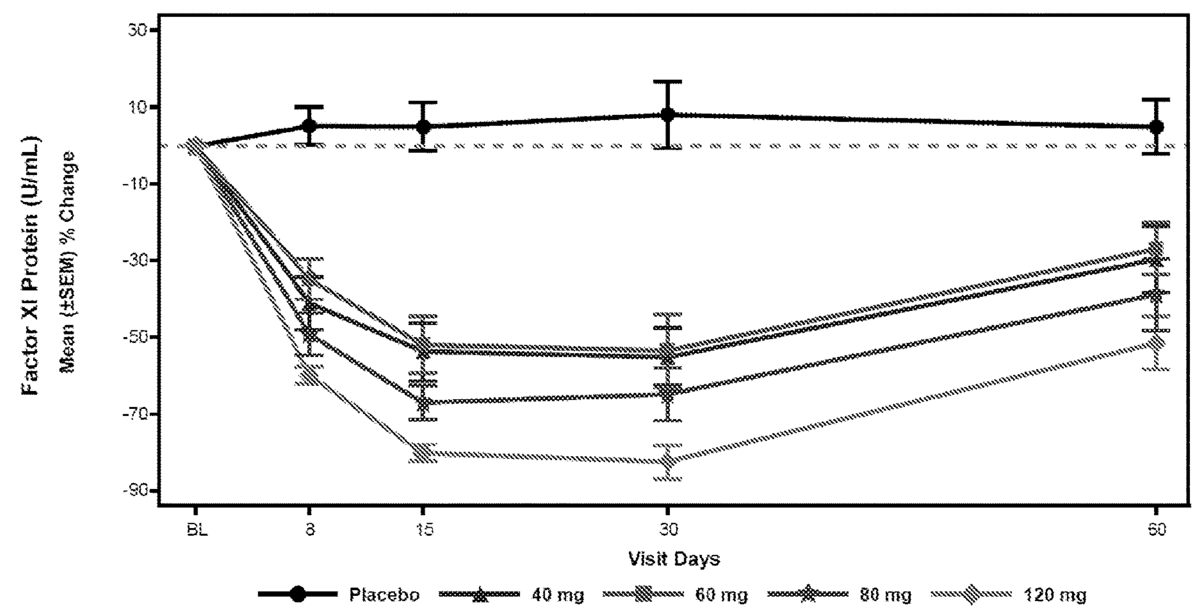

Results of the single dose study are presented in Tables 9-10 and FIGS. 1A-1B, and FIGS. 2A-2B. Table 9 and FIGS. 1A-1B show results of the activity assay. Table 10 and FIGS. 2A-2B show the results of the ELISA assays.

TABLE 9

Plasma Factor XI Activity for Single Dose Cohorts

| | | Baseline | Day 8 | Day 15 | Day 30 | Day 60 |
|---|---|---|---|---|---|---|
| Placebo | Mean | 0.999 | 1.076 | 1.063 | 1.034 | 0.983 |
| (N = 8) | Mean SEM | 0.037 | 0.055 | 0.055 | 0.039 | 0.046 |
| | % change | | 8.2 | 6.2 | 3.6 | 0.7 |
| | % change SEM | | 5.6 | 2.9 | 1.6 | 3.1 |
| 40 mg | Mean | 1.07 | 0.718 | 0.605 | 0.593 | 0.702 |
| (N = 6) | Mean SEM | 0.042 | 0.057 | 0.098 | 0.103 | 0.07 |
| | % change | | −33.1 | −44.8 | −45.9 | −34.9 |
| | % change SEM | | 3.6 | 7.5 | 8.3 | 5.3 |
| | % change P-value | | <0.001 | <0.001 | <0.001 | 0.001 |
| 60 mg | Mean | 0.978 | 0.642 | 0.487 | 0.52 | 0.656 |
| (N = 6) | Mean SEM | 0.041 | 0.057 | 0.071 | 0.087 | 0.074 |
| | % change | | −34.5 | −50.2 | −47.2 | −34.8 |
| | % change SEM | | 4.8 | 6.8 | 8.2 | 6 |
| | % change P-value | | <0.001 | <0.001 | <0.001 | 0.003 |
| 80 mg | Mean | 0.987 | 0.588 | 0.446 | 0.417 | 0.647 |
| (N = 6) | Mean SEM | 0.053 | 0.067 | 0.072 | 0.071 | 0.087 |
| | % change | | −38.8 | −54.0 | −57.8 | −34.7 |
| | % change SEM | | 4.6 | 5.2 | 6.5 | 7.8 |
| | % change P-value | | 0.002 | 0.002 | <0.001 | 0.001 |
| 120 mg | Mean | 0.94 | 0.438 | 0.227 | 0.245 | 0.542 |
| (N = 6) | Mean SEM | 0.042 | 0.029 | 0.027 | 0.058 | 0.084 |
| | % change | | −53.4 | −75.9 | −74.4 | −43.1 |
| | % change SEM | | 2.3 | 2.5 | 5.5 | 7.6 |
| | % change P-value | | <0.001 | <0.001 | <0.001 | 0.001 |

Input datasets: ADSL and ADEFF.

Note: Baseline is defined as the last non-missing measurement prior to the first dose of study drug. [A]ANOVA test P-value, [T]Wilcoxon rank sum t approximation test two-sided P-value, [E]Wilcoxon rank sum exact test two-sided P-value.

TABLE 10

Plasma Factor XI Protein Concentrations for Single Dose Cohorts

| | | Baseline | Day 8 | Day 15 | Day 30 | Day 60 |
|---|---|---|---|---|---|---|
| Placebo | Mean | 1.19 | 1.22 | 1.22 | 1.22 | 1.18 |
| (N = 8) | Mean SEM | 0.07 | 0.06 | 0.08 | 0.1 | 0.04 |
| | % change | | 3.3 | 3.1 | 3.9 | 3.0 |
| | % change SEM | | 4.6 | 5.8 | 8.5 | 6.2 |
| 40 mg | Mean | 1.14 | 0.68 | 0.54 | 0.52 | 0.81 |
| (N = 6) | Mean SEM | 0.03 | 0.09 | 0.1 | 0.09 | 0.1 |
| | % change | | −41.2 | −53.8 | −55.1 | −29.7 |
| | % change SEM | | 6.8 | 7.6 | 7.6 | 8.6 |
| | % change P-value | | <0.001 | <0.001 | <0.001 | 0.014 |
| 60 mg | Mean | 0.93 | 0.61 | 0.45 | 0.44 | 0.68 |
| (N = 6) | Mean SEM | 0.04 | 0.07 | 0.08 | 0.1 | 0.08 |
| | % change | | −35.0 | −52.1 | −53.5 | −26.9 |
| | % change SEM | | 5.3 | 7.4 | 9.5 | 6.8 |
| | % change P-value | | <0.001 | <0.001 | 0.003 | 0.018 |
| 80 mg | Mean | 1.14 | 0.56 | 0.36 | 0.4 | 0.69 |
| (N = 6) | Mean SEM | 0.08 | 0.08 | 0.06 | 0.08 | 0.1 |
| | % change | | −49.2 | −67.0 | −64.9 | −38.9 |
| | % change SEM | | 5.4 | 4.6 | 6.9 | 9.2 |
| | % change P-value | | 0.002 | 0.002 | <0.001 | 0.005 |
| 120 mg | Mean | 1.1 | 0.44 | 0.22 | 0.2 | 0.54 |
| (N = 6) | Mean SEM | 0.05 | 0.02 | 0.03 | 0.05 | 0.08 |
| | % change | | −59.8 | −80.0 | −82.4 | −51.5 |
| | % change SEM | | 2.2 | 2.1 | 4.3 | 6.9 |
| | % change P-value | | <0.001 | <0.001 | <0.001 | 0.001 |

Input datasets: ADSL and ADEFF.

Note: Baseline is defined as the last non-missing measurement prior to the first dose of study drug. [A] ANOVA test P-value, [T] Wilcoxon rank sum t approximation test two-sided P-value, +E+ Wilcoxon rank sum exact test two-sided P-value.

Notably, all doses reduced plasma FXI protein concentration and activity by an average of at least 30% at 8 days after receiving the single dose, including the lowest dose of 40 mg. Also, it is noted that plasma FXI protein concentration and activity was reduced by an average of at least 50% at 8 days after receiving the single dose of 120 mg. Plasma FXI protein concentration and activity were further reduced by an average of at least 30% of baseline levels by 15 days after receiving the 120 mg dose. This reduction was maintained at 30 days after dosing. These data suggest that a monthly dosing regimen is sufficient to obtain therapeutic effects of a single dose of Compound No. 957943.

Safety and Tolerability Evaluations

Patient safety was monitored closely during the study. Safety and tolerability evaluations included: physical examination, vital signs (HR, BP, orthostatic changes, weight), ECG, adverse events and concomitant medications, plasma laboratory tests (clinical chemistry, hematology), urinalysis, and complete blood counts (CBC). Platelet levels were measured during routine CBC measurements. Overall, Compound No. 975943 was well-tolerated. There were no safety concerns in vital signs including heart rate and blood pressure, and no clinically relevant changes in liver chemistry, renal function, or platelet values. There were no deaths, no serious adverse events or spontaneous bleeding events.

Example 5: Phase 1 Human Clinical Trial with Compound No. 957943 Multiple Dose Cohorts Varying doses of Compound No. 957943 were evaluated in a randomized, double-blind, placebo-controlled study to evaluate the safety, tolerability, pharmacokinetics and pharmacodynamics of multiple doses of Compound No. 957943 in healthy volunteers. Subjects received doses according to Table 11. Healthy volunteers enrolled in the weekly multiple-dose treatment cohorts (AA, BB, and CC) received six subcutaneous doses of Study Drug (Compound No. 957943 or placebo) starting on Week 1, Day 1 followed by once-weekly subcutaneous administration during Weeks 2 to 6 (Days 8, 15, 22, 29, and 36). Healthy volunteers enrolled in the multiple-dose treatment cohort (DDD) received four subcutaneous doses of Study Drug starting on Week 1, Day 1 followed every four weeks with SC administration during Week 5 (Day 29), Week 9 (Day 57), and Week 13 (Day 85).

TABLE 11

Multiple Dose Cohorts

| Cohort and Dose Level | Healthy Volunteers | Doses | Total Dose of Compound No. 957943 |
|---|---|---|---|
| AA: 10 mg weekly for 6 weeks (3:1) | 8 | 6 | 60 mg |
| BB: 20 mg weekly for 6 weeks (3:1) | 8 | 6 | 120 mg |
| CC: 30 mg weekly for 6 weeks (3:1) | 8 | 6 | 180 mg |
| DDD: 80 mg every four weeks for 13 weeks (3:2) | 10 | 4 | 320 mg |

Figure 3A:
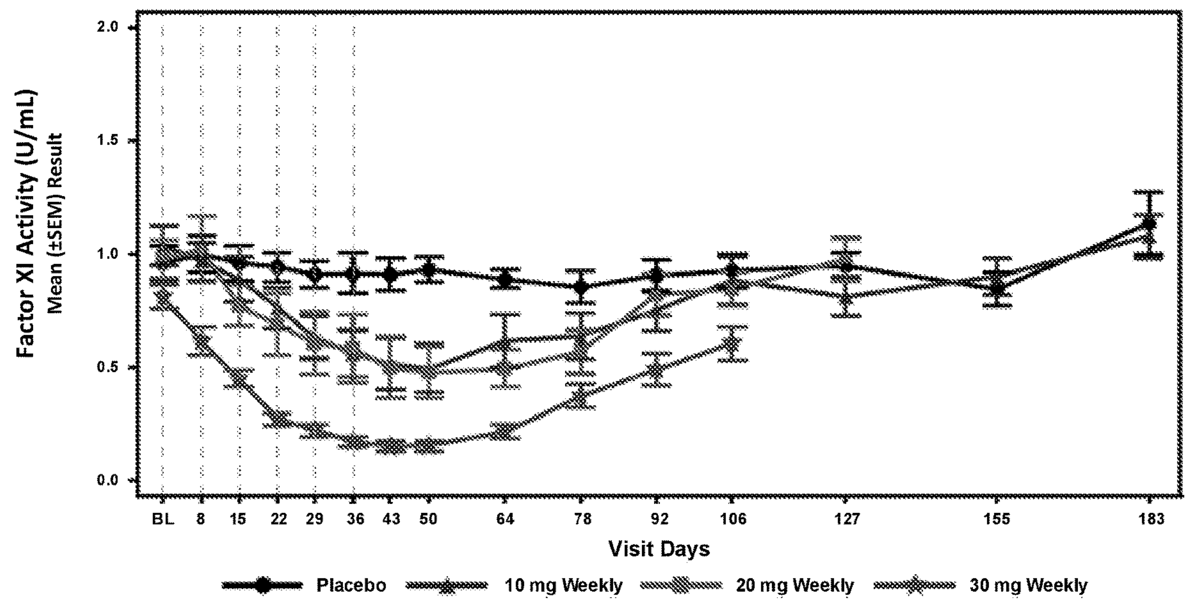
FIGS. 3A and 3B show pharmacodynamic results over time for multiple dose cohorts receiving Compound No. 957943, as measured by relative plasma FXI protein activity.
Figure 3B:
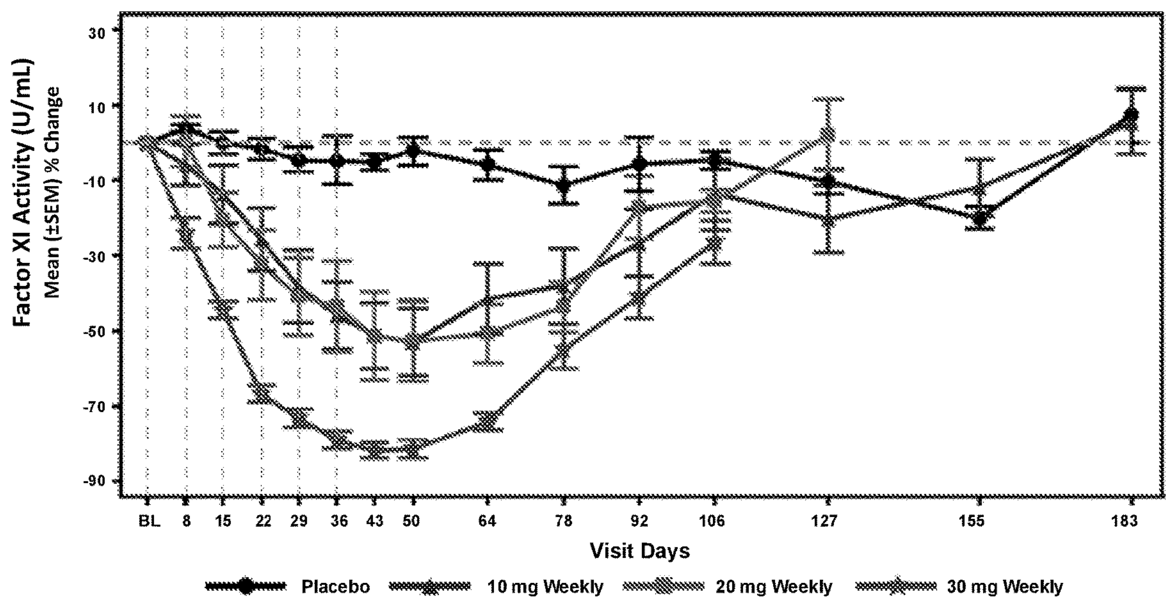
Figure 4A:
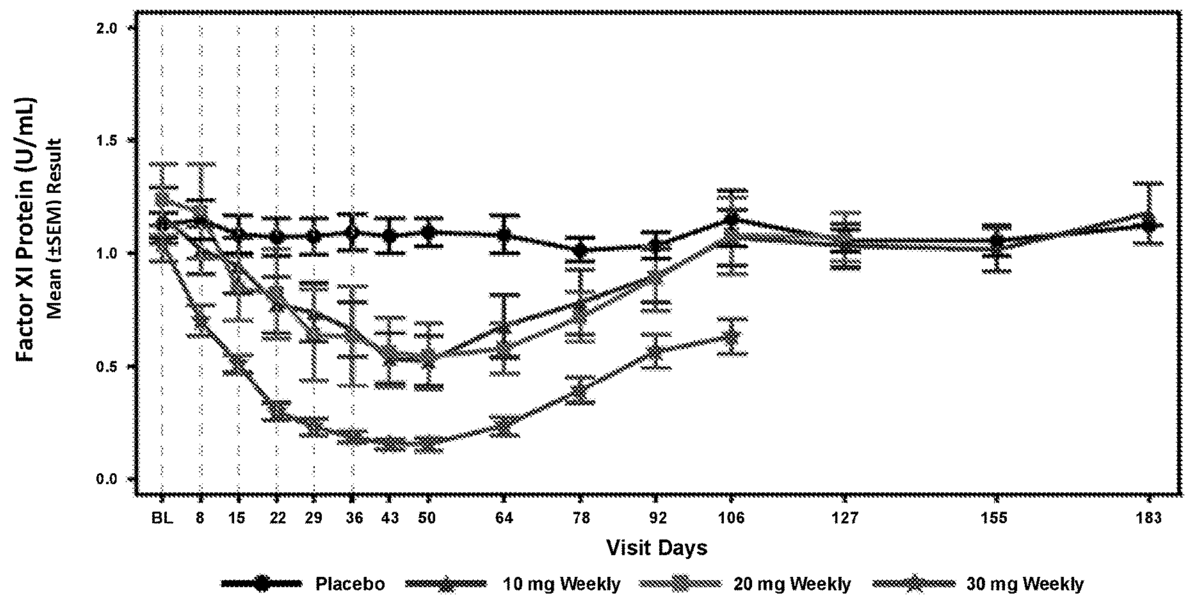
FIGS. 4A and 4B show pharmacodynamic results over time for multiple dose cohorts receiving Compound No. 957943, as measured by ELISA.
Figure 4B:
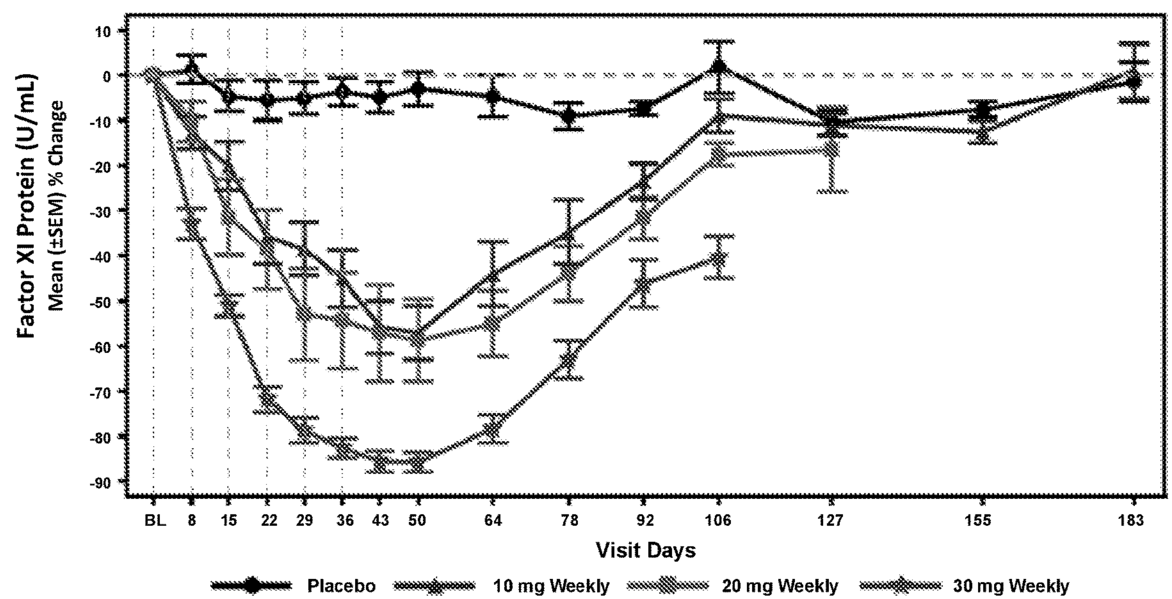

Plasma FXI concentrations for cohorts AA, BB and CC were measured by a standard ELISA assay at various time points. Results of the ELISA assay are presented in Table 12, FIG. 3A and FIG. 3B. Plasma FXI activity was also measured (as described in Example 4) at various time points. Results of the activity assay are presented in Table 13, FIG. 4A and FIG. 4B.

TABLE 12

Plasma Factor XI Activity for Multiple Dose Cohorts AA, BB, CC

| | | Baseline | Day 15 | Day 29 | Day 43 | Day 64 | Day 78 | Day 92 |
|---|---|---|---|---|---|---|---|---|
| Placebo | Mean | 0.962 | 0.96 | 0.91 | 0.91 | 0.89 | 0.856 | 0.906 |
| (N = 6) | Mean SEM | 0.074 | 0.078 | 0.06 | 0.07 | 0.041 | 0.07 | 0.073 |
| | % change | | −0.2 | −4.6 | −5.1 | −6.0 | −11.4 | −5.8 |
| | % change SEM | | 2.9 | 3.5 | 2.2 | 4.1 | 5 | 7.3 |
| 10 mg | Mean | 1.035 | 0.89 | 0.635 | 0.515 | 0.615 | 0.637 | 0.75 |
| weekly | Mean SEM | 0.089 | 0.099 | 0.095 | 0.113 | 0.119 | 0.101 | 0.092 |
| (N = 6) | % change | | −13.8 | −38.2 | −51.3 | −41.6 | −38.1 | −26.8 |
| | % change SEM | | 7.8 | 9.6 | 8.6 | 9.1 | 10 | 8.9 |
| | % change P-value | | 0.093 | 0.065 | 0.002 | 0.009 | 0.082 | 0.126 |
| 20 mg | Mean | 0.98 | 0.775 | 0.608 | 0.498 | 0.494 | 0.568 | 0.822 |
| weekly | Mean SEM | 0.083 | 0.091 | 0.14 | 0.136 | 0.082 | 0.096 | 0.091 |
| (N = 6) | % change | | −20.6 | −40.8 | −51.4 | −50.8 | −43.7 | −17.3 |
| | % change SEM | | 7.3 | 10.2 | 11.6 | 7.7 | 6.8 | 8.2 |
| | % change P-value | | 0.065 | 0.017 | 0.004 | 0.004 | 0.008 | 0.31 |
| 30 mg | Mean | 0.812 | 0.448 | 0.22 | 0.15 | 0.215 | 0.372 | 0.49 |
| weekly | Mean SEM | 0.054 | 0.036 | 0.028 | 0.021 | 0.03 | 0.053 | 0.069 |
| (N = 6) | % change | | −44.6 | −73.2 | −81.7 | −74.1 | −55.1 | −41.1 |
| | % change SEM | | 2.1 | 2.6 | 2.2 | 2.2 | 4.7 | 5.6 |
| | % change P-value | | 0.004 | 0.004 | 0.002 | 0.002 | 0.004 | 0.004 |

Input datasets: ADSL and ADEFF.

Note: Baseline is defined as the last non-missing measurement prior to the first dose of study drug.

[A] ANOVA test P-value, [T] Wilcoxon rank sum t approximation test two-sided P-value, [E] Wilcoxon rank sum exact test two-sided P-value.

TABLE 13

| Plasma Factor XI Protein Concentrations for Multiple Dose Cohorts AA, BB, CC | | | | | | | | |
|---|---|---|---|---|---|---|---|---|
| | | Baseline | Day 15 | Day 29 | Day 43 | Day 64 | Day 78 | Day 92 |
| Placebo | Mean | 1.13 | 1.08 | 1.08 | 1.08 | 1.08 | 1.01 | 1.03 |
| (N = 6) | Mean SEM | 0.06 | 0.08 | 0.08 | 0.08 | 0.08 | 0.05 | 0.06 |
| | % change | | −4.6 | −5.1 | −4.9 | −4.6 | −9.1 | −7.3 |
| | % change SEM | | 3.5 | 3.6 | 3.4 | 4.6 | 3 | 1.6 |
| 10 mg | Mean | 1.17 | 0.94 | 0.74 | 0.54 | 0.68 | 0.78 | 0.9 |
| weekly | Mean SEM | 0.12 | 0.12 | 0.13 | 0.11 | 0.14 | 0.14 | 0.12 |
| (N = 6) | % change | | −20.1 | −38.5 | −55.8 | −44.1 | −35.0 | −23.6 |
| | % change SEM | | 5.3 | 5.9 | 5.8 | 7.1 | 7.1 | 4.2 |
| | % change P-value | | 0.041 | 0.002 | 0.002 | 0.004 | 0.017 | 0.017 |
| 20 mg | Mean | 1.24 | 0.84 | 0.64 | 0.56 | 0.58 | 0.72 | 0.89 |
| weekly | Mean SEM | 0.16 | 0.14 | 0.2 | 0.15 | 0.11 | 0.11 | 0.14 |
| (N = 6) | % change | | −31.5 | −53.0 | −57.1 | −55.1 | −43.9 | −31.6 |
| | % change SEM | | 8.3 | 10.1 | 10.6 | 7.3 | 6.2 | 4.6 |
| | % change P-value | | 0.065 | 0.004 | 0.004 | 0.004 | 0.008 | 0.008 |
| 30 mg | Mean | 1.05 | 0.51 | 0.23 | 0.15 | 0.23 | 0.39 | 0.57 |
| weekly | Mean SEM | 0.08 | 0.04 | 0.04 | 0.03 | 0.04 | 0.06 | 0.07 |
| (N = 6) | % change | | −51.0 | −78.7 | −85.5 | −78.2 | −63.0 | −46.3 |
| | % change SEM | | 2.3 | 2.8 | 2.3 | 2.9 | 4.1 | 5.3 |
| | % change P-value | | 0.004 | 0.004 | 0.002 | 0.002 | 0.004 | 0.004 |

Input datasets: ADSL and ADEFF.

Note: Baseline is defined as the last non-missing measurement prior to the first dose of study drug.

[A] ANOVA test P-value, [T] Wilcoxon rank sum t approximation test two-sided P-value, [E] Wilcoxon rank sum exact test two-sided P-value.

Figure 5A:
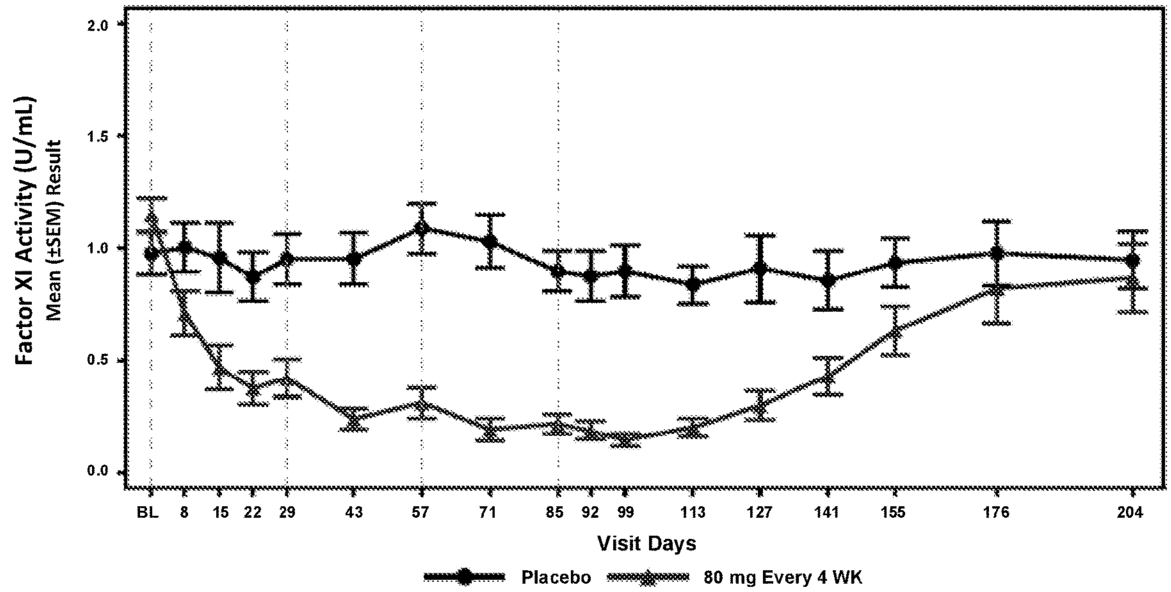
FIGS. 5A and 5B show pharmacodynamic results over time for multiple dose cohorts receiving 80 mg Compound No. 957943 every four weeks for thirteen weeks, as measured by relative plasma FXI protein activity.
Figure 5B:
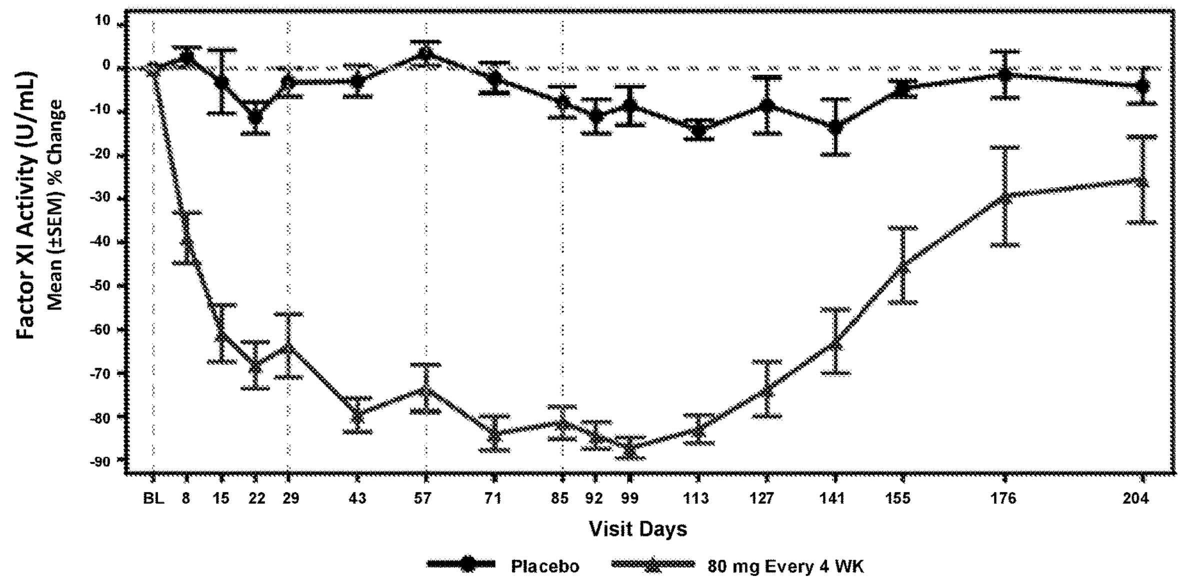
Figure 6A:
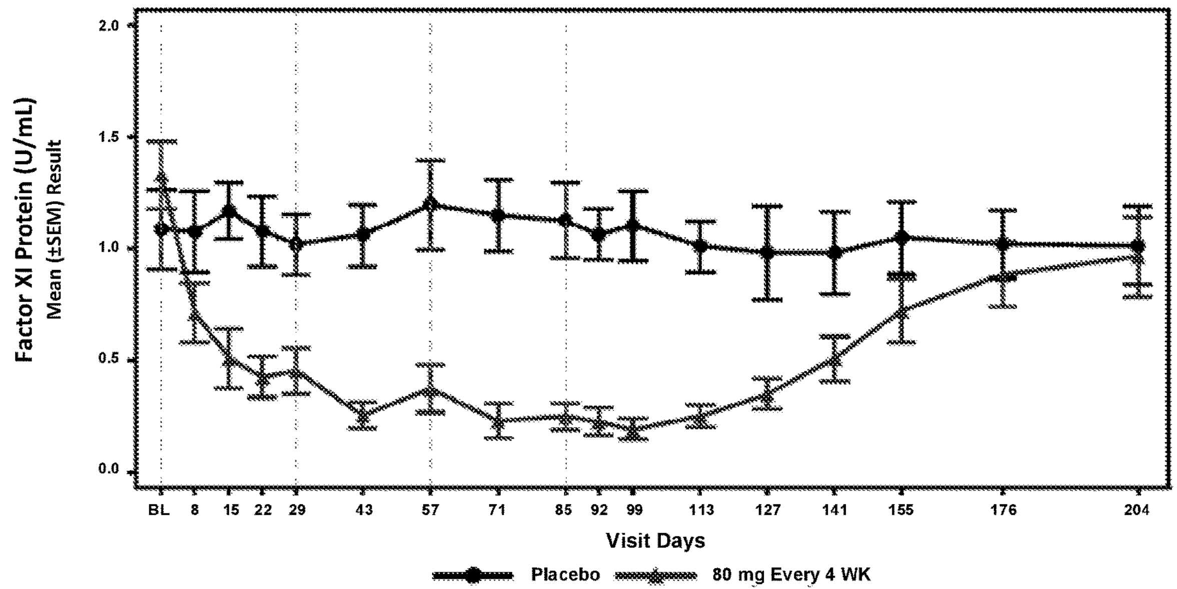
FIGS. 6A and 6B show pharmacodynamic results over time for multiple dose cohorts receiving 80 mg Compound No. 957943 every four weeks for thirteen weeks, as measured by ELISA.
Figure 6B:
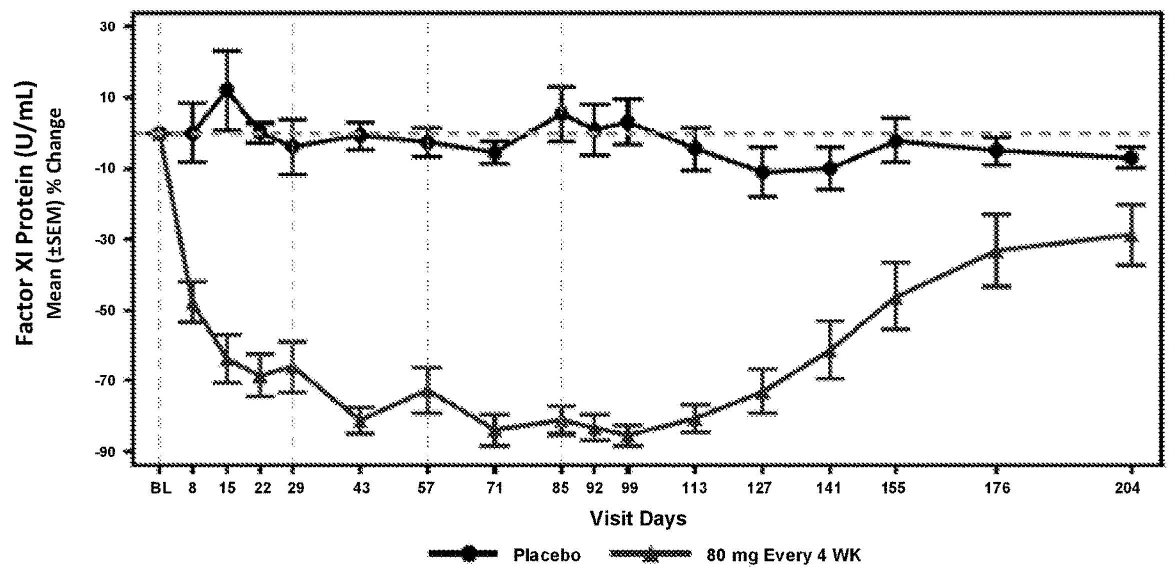

Plasma FXI concentrations for cohort DDD were measured by a standard ELISA assay at various time points. Results of the ELISA assay are presented in Table 14 and FIG. 5A and FIG. 5B. Plasma FXI activity was measured with an assay conducted in FXI-depleted plasma as described in Example 4 at various time points. FXI activity is presented in Table 15, FIG. 6A and FIG. 6B.

TABLE 14

| Plasma Factor XI Activity for Multiple Dose Cohort DDD | | | | | | | | |
|---|---|---|---|---|---|---|---|---|
| | | Baseline | Day 15 | Day 29 | Day 43 | Day 71 | Day 99 | Day 113 |
| Placebo | Mean | 0.975 | 0.958 | 0.95 | 0.953 | 1.03 | 0.898 | 0.838 |
| (N = 4) | Mean SEM | 0.095 | 0.153 | 0.114 | 0.115 | 0.118 | 0.115 | 0.085 |
| | % change | | −3.0 | −3.0 | −2.9 | −2.1 | −8.5 | −14.1 |
| | % change SEM | | 7.3 | 3.2 | 3.5 | 3.5 | 4.4 | 2 |
| 80 mg | Mean | 1.145 | 0.467 | 0.422 | 0.238 | 0.192 | 0.147 | 0.198 |
| every 4 | Mean SEM | 0.073 | 0.099 | 0.085 | 0.048 | 0.051 | 0.028 | 0.039 |
| weeks | % change | | −60.8 | −63.7 | −79.6 | −83.9 | −87.3 | −82.8 |
| (N = 6) | % change SEM | | 6.4 | 7.2 | 3.9 | 3.9 | 2.4 | 3.4 |
| | % change P-value | | 0.01 | 0.01 | 0.01 | 0.024 | 0.01 | 0.01 |

Input datasets: ADSL and ADEFF.

Note: Baseline is defined as the last non-missing measurement prior to the first dose of study drug.

[A] ANOVA test P-value, [T] Wilcoxon rank sum t approximation test two-sided P-value, [E] Wilcoxon rank sum exact test two-sided P-value.

TABLE 15

| Plasma Factor XI Protein Concentrations for Multiple Dose Cohort DDD | | | | | | | | |
|---|---|---|---|---|---|---|---|---|
| | | Baseline | Day 15 | Day 29 | Day 43 | Day 71 | Day 99 | Day 113 |
| Placebo | Mean | 1.09 | 1.17 | 1.02 | 1.06 | 1.15 | 1.1 | 1.01 |
| (N = 4) | Mean SEM | 0.18 | 0.12 | 0.14 | 0.14 | 0.16 | 0.16 | 0.12 |
| | % change | | 12.0 | −3.9 | −0.7 | −5.6 | 3.2 | −4.4 |
| | % change SEM | | 11.3 | 7.7 | 3.8 | 3.1 | 6.6 | 6 |
| 80 mg | Mean | 1.33 | 0.51 | 0.45 | 0.26 | 0.23 | 0.19 | 0.25 |
| every 4 | Mean SEM | 0.15 | 0.13 | 0.1 | 0.06 | 0.08 | 0.05 | 0.05 |
| weeks | % change | | −63.8 | −66.1 | −81.1 | −83.9 | −85.5 | −80.6 |

TABLE 15-continued

Plasma Factor XI Protein Concentrations for Multiple Dose Cohort DDD

| | | Baseline | Day 15 | Day 29 | Day 43 | Day 71 | Day 99 | Day 113 |
|---|---|---|---|---|---|---|---|---|
| (N = 6) | % change SEM | | 6.9 | 7 | 3.7 | 4.5 | 3.1 | 3.9 |
| | % change P-value | | 0.01 | 0.01 | 0.01 | 0.024 | 0.01 | 0.01 |

Input datasets: ADSL and ADEFF.

Note: Baseline is defined as the last non-missing measurement prior to the first dose of study drug.

[A] ANOVA test P-value, [T] Wilcoxon rank sum t approximation test two-sided P-value, [E] Wilcoxon rank sum exact test two-sided P-value.

FXI plasma protein and activity was reduced in all subjects receiving Compound No. 957943 at all doses at all time points. Results of these studies support a monthly dosing regimen.

Safety and Tolerability Evaluations

Patient safety was monitored closely during the study. Safety and tolerability evaluations included: physical examination, vital signs (HR, BP, orthostatic changes, weight), ECG, adverse events and concomitant medications, plasma laboratory tests (clinical chemistry, hematology), urinalysis, and complete blood counts (CBC). Platelet levels were measured during routine CBC measurements. Overall, Compound No. 975943 was well-tolerated. There were no safety concerns in vital signs including heart rate and blood pressure, and no clinically relevant changes in liver chemistry, renal function, or platelet values. No deaths, spontaneous bleeding, or serious adverse events were observed.

Example 6: Phase 2 Human Clinical Trial with Compound No. 957943

Multiple doses of Compound No. 957943 are evaluated in a Phase 2 multicenter, randomized, placebo-controlled study in ESRD patients receiving hemodialysis. Patients are randomized to receive subcutaneous treatment (low, mid, high dose) with either Compound No. 957943 or placebo. All standard of care hemodialysis therapies as prescribed by their providers are continued, except anticoagulants or antiplatelet medications other than acetylsalicylic acid (e.g., aspirin) up to 150 mg daily.

All cohorts consist of a screening and approximately 6 months treatment period followed by a post-treatment follow-up period.

Pharmacodynamics and efficacy are assessed at multiple time points. Patient safety is monitored closely during the study. Safety and tolerability evaluations may include e.g. physical examination, vital signs, adverse events, concomitant medications, and plasma laboratory tests.

The invention claimed is:
1. An oligomeric compound according to the following chemical structure:
(SEQ ID NO: 3)
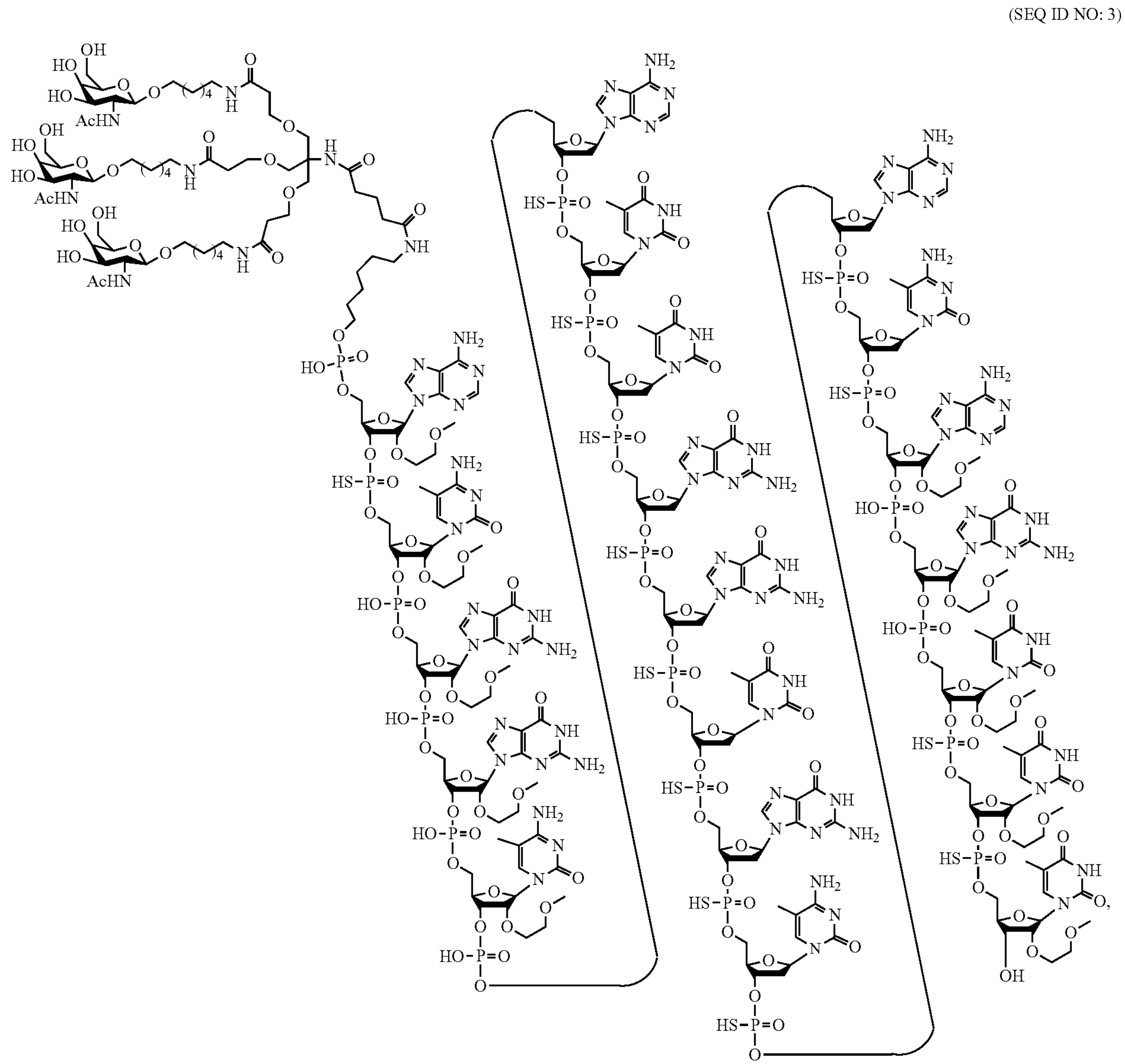
or a salt thereof.
2. An oligomeric compound according to the following chemical structure:

(SEQ ID NO: 3)
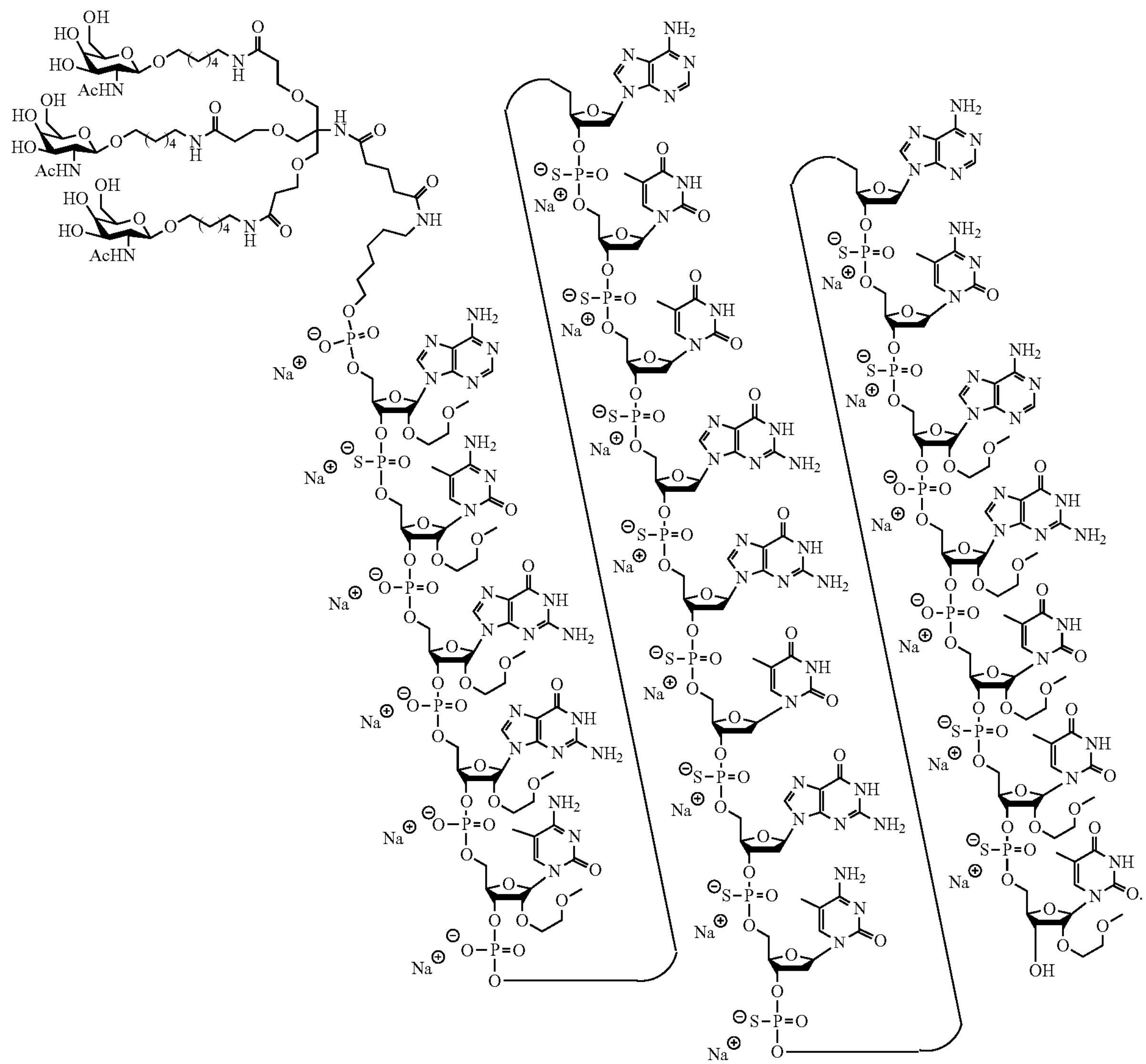
3. An oligomeric compound comprising a modified oligonucleotide and conjugate group according to the following formula:
(THA-GalNAc$_3$)o Aes mCeo Geo Geo mCeo Ads Tds Tds Gds Gds Tds Gds mCds Ads mCds Aeo Geo Tes Tes Te (SEQ ID NO: 3); wherein, (THA-GalNAc3)o is represented by the following chemical structure:

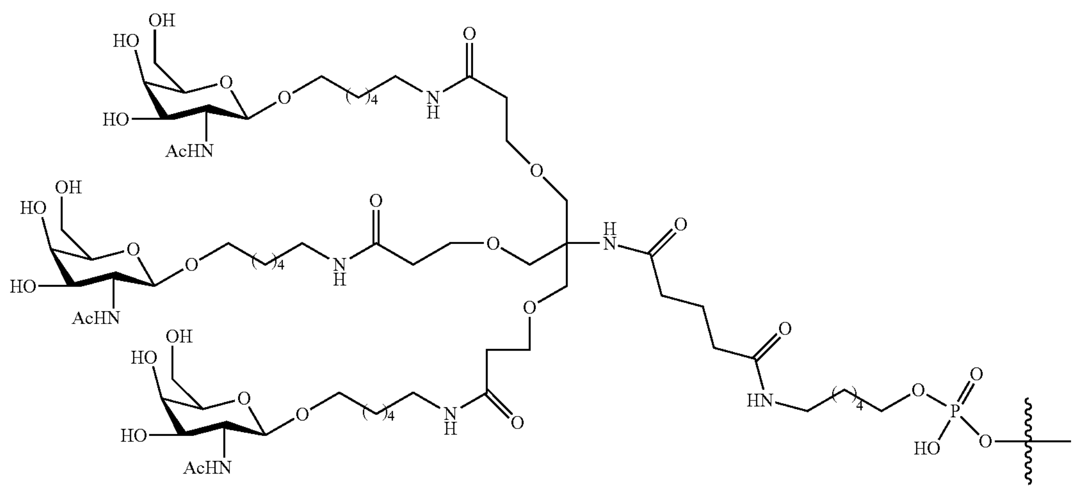

and wherein,

A=an adenine nucleobase, mC=a 5'-methyl cytosine nucleobase,

G=a guanine nucleobase,

T=a thymine nucleobase, e=a 2'-MOE modified sugar, d=a 2'-deoxyribose sugar, s=a phosphorothioate internucleoside linkage, and o=a phosphodiester internucleoside linkage;

or a salt thereof.

4. The oligomeric compound of claim 1, which is a sodium salt or a potassium salt.

5. A chirally enriched population of the oligomeric compound of claim 1, wherein the population is enriched for oligomeric compounds having a modified oligonucleotide comprising at least one particular phosphorothioate internucleoside linkage having a particular stereochemical configuration.

6. The chirally enriched population of claim 5, wherein the population is enriched for oligomeric compounds having a modified oligonucleotide comprising at least one particular phosphorothioate internucleoside linkage having the (Sp) configuration.

7. The chirally enriched population of claim 5, wherein the population is enriched for oligomeric compounds having a modified oligonucleotides comprising at least one particular phosphorothioate internucleoside linkage having the (Rp) configuration.

8. The chirally enriched population of claim 5, wherein the population is enriched for oligomeric compounds having a modified oligonucleotide having a particular, independently selected stereochemical configuration at each phosphorothioate internucleoside linkage.

9. The chirally enriched population of claim 8, wherein the population is enriched for oligomeric compounds having a modified oligonucleotide having the (Sp) configuration at each phosphorothioate internucleoside linkage.

10. The chirally enriched population of claim 8, wherein the population is enriched for oligomeric compounds having a modified oligonucleotide having the (Rp) configuration at each phosphorothioate internucleoside linkage.

11. The chirally enriched population of claim 8, wherein the population is enriched for oligomeric compounds having a modified oligonucleotide having at least 3 contiguous phosphorothioate internucleoside linkages in the Sp-Sp-Rp configurations, in the 5' to 3' direction.

12. A population of oligomeric compounds having a modified oligonucleotide of claim 1, wherein all of the phosphorothioate internucleoside linkages of the modified oligonucleotide are stereorandom.

13. A pharmaceutical composition comprising the oligomeric compound of claim 1, and a pharmaceutically acceptable carrier or diluent.

14. The pharmaceutical composition of claim 13, wherein the pharmaceutically acceptable diluent is phosphate buffered saline or water.

15. The pharmaceutical composition of claim 13, wherein the pharmaceutical composition consists essentially of the oligomeric compound, and phosphate buffered saline or water.

16. A pharmaceutical composition comprising the oligomeric compound of claim 2, and a pharmaceutically acceptable carrier or diluent.

17. The pharmaceutical composition of claim 16, wherein the pharmaceutically acceptable diluent is phosphate buffered saline or water.

18. The pharmaceutical composition of claim 16, wherein the pharmaceutical composition consists essentially of the oligomeric compound, and phosphate buffered saline or water.

* * * * *

UNITED STATES PATENT AND TRADEMARK OFFICE

CERTIFICATE OF CORRECTION

PATENT NO. : 11,021,710 B2
APPLICATION NO. : 17/091891
DATED : June 1, 2021
INVENTOR(S) : Huynh-Hoa Bui It is certified that error appears in the above-identified patent and that said Letters Patent is hereby corrected as shown below:

In the Specification

At Column 15, Line 36, please replace “mC=a 5'-methyl cytosine nucleobase” with --mC=a 5-methyl cytosine nucleobase--;

At Column 82, Line 65 to Column 82, Line 66, please replace “each cytosine is a 5'-methyl cytosine” with --each cytosine is a 5-methyl cytosine--;

At Column 85, Line 24, please replace “mC=a 5'-methyl cytosine nucleobase” with --mC=a 5-methyl cytosine nucleobase--;

In the remarks accompanying Table 1, at Column 91, please replace “cytosine residues throughout each gapmer are 5'-methyl cytosines” with --cytosine residues throughout each gapmer are 5-methyl cytosines--; and In the Claims At Column 137, Line 24 (Claim 3), please replace “mC=a 5'-methyl cytosine nucleobase” with --mC=a 5-methyl cytosine nucleobase--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 12

<210> SEQ ID NO 1
<211> LENGTH: 26001
<212> TYPE: DNA
<213> ORGANISM: Homo sapien

<400> SEQUENCE: 1

atgccctcca taggctttca gaccttcttc aaggccaaag ggaaggcctt catggaaata      60

taattatgtg aaacacccca gaatttttc acaaactttc ctgcctataa acgccaggtc     120

ctaccactgt ccagtgtccc acttcccact gtccagtggg aagactccct ccaggacaaa     180

accaccettt ccttcaggga tgtgacgtgc tgtgctttcg ttgacagtca tgcagctgct     240

agacatgtca cttcctagct ctccattcgg gtctgtgtcc caggacctaa agaaagctaa     300

aagaagccgg gcgtggtggc tcatgcctgt catcccagca ttttgggagg ctgaggctgg     360

cggatcactg gagatcagga gtttgagacc agtctgacca gcatggtgaa accctgtctc     420

tactaaaaat acaaaaaaag aaaagaaaaa agaaaaaaaa ataagctggg cgtggtggcg     480

cgggcctgta gtcccagcta ctccggaggc ggaggcagga caatcacttg aacctggaag     540

gcggaggttg cagtgagctg agatcgcgtc attgcactcc agcctgtgcg acgagagact     600

ctgtctcaaa agaaagaaag aaagagagaa agaaagaaag aaagaaaaga aagaaagaaa     660

gaagaaagaa agaaaagaaa gaaagtaaga agcaagcaag ctgaaatagc ttattttct     720

gttttaaaaa atagactttt agtgttcaca agtaagaata aaaaaaaaa aagcttggcc     780

ttaggaggaa tcctatctgc ttaggcctct gagaggcagc gtcacctgaa gggaaactga     840
```

```
ctgggcaaga gccaggctct taggagctgt ctgtactttg cttcccatcc gtccgctctc    900
ccccagcagc caaagtctcc tccctccatt atattgcaaa tcaatgaatc cattagactt    960
tccatgtttt ctttttagac tttgagattc aaggtcagct agaattaatg gttaacagct   1020
gacaggtgaa agtgtggtta aatgcagctt tggctagcag gcacacaggc aaaatcaagt   1080
tctacatctg tccctgtgta tgtcacttgt ttgaatacga aataaaatta aaaaaataaa   1140
ttcagtgtat tgagaaagca agcaattctc tcaaggtata tttctgacat actaagattt   1200
taacgacttt cacaaatatg ctgtactgag agagaatgtt acataacatt gagaactagt   1260
acaagtaaat attaaagtga agtgaccatt tcctacacaa gctcattcag aggaggatga   1320
agaccatttt ggaggaagaa aagcaccctt attaagaatt gcagcaagta agccaacaag   1380
gtcttttcag gtacagtttc agaacttact atttaacatt cctctcaagc aaatacgcct   1440
tgaaatgctt tttttaaatc ataggaattt aaaaacactt tacaatagag aatgattgat   1500
ttttaaaatg tgtctgattt agctttgtag agatgttccg ctaatatcca taactaatct   1560
gagaggaaat gtggaacaac agaagagtaa cagtgtctac tcagtaacaa gcgttttacg   1620
agttaaaaag acatccaaat gcagtactga aaaatcagaa gtcttgattt gtctcactga   1680
tgactccgtt tttcctagag cagtctgttt aatgcttact ggagataaat agatttatag   1740
gtgaccaaga caatcgatta atgtatcagc cacagacttt tttaaataga aaattttcta   1800
agtaggaaat cattcatagc tctttgaaag atatagggag aggcctcaag gaaagaaaga   1860
aaggaaaaaa attgggaaag gaaacaaaga tgaaaaattg gggtggggag agcggtcaga   1920
tggtggccat gagaaggatc tgaacacaga gagcggcggg gccggcgggg aaggagggag   1980
gaggggagag cgctgcttcc ctgtgggttc cggcttctgc agagctgtaa gagttgaatg   2040
ccacacacag tcacactaag gaatgctcca ggattgggaa agaaaattca acattataat   2100
gagaacactg tgaatgctat tgaattaact actcccctct ctccctattt cttgtaagtc   2160
ttagtgtcag taaactaatt ataaatttac attttatgtt ctaaaagcat gcaccttttt   2220
ctcattgtag gatgatttc ttatatcaag tggtacattt cattttattt acttcagttt   2280
ctggtggtaa gtagagtgtt atcttaacta tgggctggga gagggaaatc acactgcaat   2340
ctccacacat gtgggagaat cccacaccat ttatgccggg aaggaaataa aatgttttta   2400
ttaacttcct gcctgaggct ccagaggttt tcaaagcagg gtaggaattg aggtgaaaaa   2460
attgtttgta ctggtaggaa tctgtgtcta tatgtgtacc atatctacat ccatgcctac   2520
atacatcatt catttaaatg atatttaaaa gcaatattaa aaagaagaaa tcttgatttg   2580
cctcactaat tagttggttt ttcataaagc agtcagttca atggaacata cacacacaca   2640
taaaatagga attttgtact gaaaaatgtt atgtaactat tcatacacag tttatgcatt   2700
tcaataattt aactaccctg ttaattctcc accctatgtc acatctgcta aatttgttta   2760
taaattactt agccaatatt aagtaggata tatcagtaca ggtattgttt agttccatga   2820
ccattcttta tttaaaatga aagctgaagc attcctttag aaaaatagct tatgtctaca   2880
tgttatattt aatttctgat actattgcta gcattttaag catagtaaat tctttttgct   2940
ggcctatgtg aaaaaaggca aacctaggtg aagatattaa aagtaaattc cacttaatat   3000
attaaattac acagctcata atttcaattt tctctgtgac aagactactg ctcaggttat   3060
aatattcctt tgttataatt atctggaaat tgtattgtta tttcattgat aaatatgtca   3120
gcgctaaata atttgatata ttttgaacac tggacccaat aactacataa acaattgacc   3180
```

```
ctgaatcagg ggttccacat ccatggattt aaacaacatt gaagtgaaat tttttaaaaa   3240
aaattatatc tgcactcaac atgtgcagag ttttttcttg tcattattcc cgaaacaaca   3300
cagtataaca acaatttgca tagtatttac attgtactag gtattataag taatctagag   3360
atgatttaaa gtacacagga ggctgtgagt aggttatatg taaatactat gccattttct   3420
atcagggact tgagcgttca tggattttgg tatctgcagg aggtctggca gccaatccct   3480
catagatatc aaggaatgat agtgtacata tttaggtcct ttatacatgc acatggaaca   3540
tttacaaata ttgaccacac acaagcctct gaaacaaggc tcaacaaatt ttaaggggtt   3600
aaaattatac tgatcatgtt attcaatcac cgtgaatggg agctagaata ataataaaaa   3660
gggaattgaa aatctgcaaa cgtttgaaaa ttgagtattt ataatcaccg tgaatgggag   3720
ctagaataat aataaaaagg gaattgaaaa tctgcaaatg tttgaaaatt gagtatttat   3780
acctttttag attaagatga atcagagatg aaatcacaat ggtaattaga aaaggaattg   3840
tacaataatg aaagtacagt atatcaaaac tttgagatgt aaccgaatca gtgttgagat   3900
caaatgtata gatttacatg tatacattag aatacagaaa agggaaaaat taatgatata   3960
agatgacaag aagatagaga atagcaactt aagtgctaag aaattagaag gcagaaagaa   4020
gaaatcgcag aaattaatta aatggaagac acacatattt gagaggtcaa cataacccct   4080
ttctagccca ttttataagg tcagggtaat cttgacacca aaatctgata ggaaaattct   4140
gaggaaaaaa agtcacaggt cttttatctt atgaacatat gtacaaatgt cctaaacaaa   4200
atattatcca acttaaccca gtagattgtt aaaaaaatta aaggatgatt acattgtgat   4260
attgtgacaa agttgggttt attccaggaa tgaaaagttg atttaacatt caaaaatcaa   4320
tagatgtgtg acttcggggt acataccgaa aaaaaagaag ggaaagcagg aactcacaca   4380
gatatacttg tacacccatc tcatagcagc attattcaca ctaacccaaa ggtggaagca   4440
gcccatgtgt ttatcaacag gtgactggat aaagtgtggt acatacatac aaaggaatat   4500
tactcaaccc taaaaagaaa ggaaattctg acacatgcta tgacatggat gaaccttgag   4560
gacattacgc taagtgaaat aagccagtca caaaagaaca aatactgtgg gatctcactg   4620
ataggaggta cttagggtag tcaatttcat caagacggaa attagaacag aggttgccag   4680
gggccgaggg gccaggggaa gggctgaggg ttggtgttta atgggcacag agcatcagct   4740
ggcgaagttg aaaagttctg gaggtggatg gtgctgatgg ttgcacagca atgtaaatac   4800
ccttagtgcc acagaactgt acactcaaga tggctacatg gcacatggta tgctatctgt   4860
cataataaaa aataaaaata attttaaatg ttaatatgtg ccgaaaaatg cttgctaaaa   4920
ttctattaat gatcaaaact ttaaataaac tggaaatgga agagaacttt catcagctat   4980
taaacgatat tttaaacaaa agcaaacaaa aatccaaacc aaaaatcttc aagaaacata   5040
atacgtaata gcggaatatt gaaagctttc ccaagggatt gagaatagga caagaatact   5100
tcccattatt tccatttact cttgactgga ggtactcgtt ggtgcggtaa ggaagggaaa   5160
taaaaggaaa acgattagga ggaacataag ctctcgtttt tcacagatga tgtgattgag   5220
tacctagaaa aatccaaaat taaccatcac ataaattatt tgagccaatt aattaaatga   5280
gtaagaagtc tcgatacaac gtcaatatac aacagcaagc acttgctcgt tcgcaaaagc   5340
agatgaacta gtttttactg acactagaag cagcatgtgt tccatgtgtt ccacatccat   5400
gcactcaaac aaccttgacg tgaaatattt ttttaaaaaat tgtatctgta ctcaacgtgt   5460
gcagagtttt tttccaaaat tgttttccaa aaatttttaa atgtttatat gtttaggggg   5520
tgtaagtgca gatttcttac atacatatat tatgcggcgg tgaagtgccg gcttttggtg   5580
```

```
tacccatcac ccaagtagtg aacacagcct ccaacaggta atttttcaac gctcacccca   5640
ctcccatcct cccatctagt ggcatattga aaatcaattt gtcttgtaaa attaaataat   5700
ccaattagga gggggatata ttctaaggaa attagtgcat gatgcacaca cacacacaca   5760
cacagaacac gtgtgtgcgc atgtgcacat gagagagagt gagagagaaa ctgggtcttg   5820
ctctgtcgcc caggctggat tgcagtggta aaatcacagc tcactgcagc ctcaaactcc   5880
caggctcagg agatcctcct acctcagcct cccgagtagc tgggattaca ggtggaaaca   5940
accatgccca gctagtattt tttttttttt ttgtattttt tatagagaca gggtcttgcc   6000
atgttgccca ggctggtctt gaactcctca gctcaagcaa tctacctacc ttagcctccc   6060
aaagtgctgg gattacacgc atgagccact gcgcccactc cgcattatta aatatagaac   6120
atttatttga ttcatcagtt aatattcttc ttaaaagtac tattttaatg tagcaagatt   6180
gctttccacc aaaaggtggg gtttccacgg tggggtttcc aaattattct caatggggtg   6240
aggatgtgtg ttatcacacc cccgagccat cagatgctgt cagaaagtga tcactctgaa   6300
gtctttgttt caaataagca cagggtttgg ataaagagac gcaattagga aaggaaaaag   6360
cagaaggctc gttccagacc tggatgagat cctaaaaagc agcagctttt gccagtaaag   6420
atccttgaaa tgattcaatt accctcaaag cactccttgt ctccaagaca atcactcata   6480
agcacaattc cattgaagcc aacgtaccat tttgtgattt tcgtttccac ctgaggctgt   6540
tcattcaata aactcacata aaagtgttta ttgccttgat ttccaaattc aggcgtattt   6600
cctggtaagt agagctactt gccttgcctt tatgagatta ccacctaact agatgtatgc   6660
ccagtaaaat ccaacataac gcatgccatg tactacatca cagaatgtgt gactcagttg   6720
ttgaaggaca cctgctttga aggaggggac attactacgg tcttcacacc aagcgccaag   6780
tactgccagg tagtctgcac ttaccaccca agatgtttac tcttcacttt cacggcggaa   6840
tcaccatctg aggatcccac ccgatggtaa atgcttatgt ttctacatcg aggagacaga   6900
tttttaaagg gagattgcta ttcttaacac atttccatct aacattttat aaaatttaac   6960
attaacaact ggaagataaa ttgtctttca gttgaaatat tgttacagaa agaagtgatg   7020
gtgtttacgc aatttagaaa agaataaata tgcctccaag tgtagacttt ccagcctctc   7080
ctatagtctc atattaatgg tatgtttctt ctgtttgtct caatttttac acttcttaaa   7140
catttcacac tttgcttttc tatcgattat taatttttgt cgtgcttctc aacaaactgg   7200
aacttctccc aactatttta ttagaaaaaa ataaaatatt taaaaagaaa atttgaaaaa   7260
aagtacagta cagtgatccc cctgccacca ccaaaaccgc aatgtttgct atatttgtac   7320
agcaatatac aatatacaat acctatattt gtatacatgt ttaaccgttt gaaataattt   7380
taaaacatga cactttaccc ctaaatactt cagcatgcac tatcctacac aaaagacata   7440
cgaaatttaa caagaattcc tttatattat ttcagttttc cctcaaatat aatttatagt   7500
aattaaccag aatcttacca agagtcactc actgcattgg gtggtttgtc aggtttaaaa   7560
cattttaaac agtccaccaa ccatttgtat tcccatcctg agcttgaaaa tttaataata   7620
agcctttctg tagaattaag ttttcaacat ctttattatt gctacattca caggcattta   7680
tgtagcaccc agaacttata aaatttacta ttccagaacc tagagcaggg attggcaaat   7740
gtcttcttaa taacgcagag taaatatgtt aggctttgtg ggcaaaaccc acagtaaagc   7800
caaggatatt atttaagtat ttatgtcacc acttaaaatg taacaatttg aaaatataaa   7860
aatcattttg tatagctaac aggctaaaca gaaacacaca gatttttggt tgcattttac   7920
```

```
caacaggtcc tagttgacac attcctgttt gttcctatta gaaaggagta ttacatgcag   7980
tctcttaagt gtagggatat tgaagtaaaa aacaaactca gaatcttgct aagaaaatat   8040
ttgttttggc atgagataaa gtagtttgtt tccttctttt tggctttctg tgtgctgact   8100
tttaagatcc attattttaa aaacataaat tcctattcat taatatgtat tttttaaaaa   8160
aacaggttta cttgtgtcct gaaagacagt gttacagaaa cactgccaag agtgaatagg   8220
acagcagcga tttctgggta ttctttcaag caatgctcac accaaataag cggtaagata   8280
tgttctcaga atcaacaaat accagctgtg atgtacacat atcgccacat cggatgtggt   8340
tttaaggcta tgaaatgaaa cactgctatg tggaaataaa ccccccttaat gaagttcttt   8400
cagtgtagag tataaactag tatacataca tgcctgccct ccaacacact gtaaaaacct   8460
ctttacctca tagaaagaca tatcttacta cctcacttcc catcatttat ttatattctt   8520
tctatttccc agcctaaaat cttaaatgaa agtctttttt tttttgagac agggtctcac   8580
tctgttgtcc aggctggagt gcagtggtgc aatcacagct cactccagcc tcaacctcct   8640
gggttcaagt gatcttcctg ccttagcctc tggagtagct gggaccagag gcatgcacca   8700
acattcccag ctaatttgtt catttttcct agagacaggg tctcactgta ttgcccaggc   8760
tggtctcaaa ctcttggcct caagtgatct gcccgcctcg gccttccaga gtgccgggat   8820
tccatggtgc ccagtcgaaa ttctttatta aacgtattaa tccaaattga aaggagcaaa   8880
tataaaggtt gaagtgacac ttgtcttaat agtgaataga tacttgaatc agttaattag   8940
cgaaataatc agtgcagtta gggagaagag aggctaggtc agaaaatcaa aatgtgaatt   9000
tacaagtcta aaattgttac agtgtaagaa ggacattggc attcttttac tgcttccatt   9060
caagaataag aattttgcag attaatataa cgaaagacct ctgaggaaag gtgggtgaaa   9120
aagttgaaag gatgagtcag gagggacagt tgcttaggtc attgccccta gaatctggaa   9180
ggtactcatg tcttctgctt ttatttccag cttgcaacaa agacatttat gtggacctag   9240
acatgaaggg cataaactat aacagctcag ttgccaagag tgctcaagaa tgccaagaaa   9300
gatgcacgga tgacgtccac tgccactttt tcacgtacgc cacaaggcag tttcccagcc   9360
tggagcatcg gtgagtgagt cccaggacat tcgagtggtc gatgaaaaac agaatcgtga   9420
tttactaaaa agcttttgcc atcaacttta tgccagaatt tattttgaac ccctaaaaga   9480
catttctata atagtactcc tagttttctt catgaaaaat acacttaaag cctaatttgg   9540
atgcatttca tttatggtaa ggagtctatc ttttaataac actgtcagaa aaatatatat   9600
acttggctaa tttcaaaagc gctacacttt taaattggca cttttgaaac agctgcaatt   9660
ggtatgattg tcagtgccct tcccagtcta aaaaatgtta cagtctaaca gaataaaaat   9720
aaaaacctac tctctctctc tctaaataac agttccttac ctaagacaaa atactcatgt   9780
aaaaagtctt atcctgctcc atactggatt ttgaaatatt tcaaggataa atctatcaca   9840
taaggattta aaaattatct gatctctaat aaccaaatct gtgttctcat ctttaaaaat   9900
ttactaggga aatagattat taatttgtat attcagaaat atttgagatg atttagattt   9960
tcatagtaaa ctgcatttat ctggaatcaa cagaaaagtg aaaaacattc aaattactaa  10020
tacttgcgtt ttaacattgg attttaacat tctgctctcc acattcacaa agaggagtga  10080
acagaaagca aacaaagcat caacgagtta tttcaaaaac aacagtggtg aaaaacacac  10140
acaccaaacc cctaaattca tgatttgact tgtaaggctt atctttagct cagctcagac  10200
gacagctttt atgtctaaga cttaacagaa tgtgaactgc aagacaagaa attggaggtt  10260
tctaagcaag ataaagttaa gtcattaaaa gtaagaagga cttagccagg cgcggtggct  10320
```

```
cacacctgta atcccagcac tttgggaggc cgaggcgggc agatcacctg aggtcaggag  10380
ttcgacacca gcctgaccaa tatggtgaaa ccccgtctct actaaaaaag aatacaaaaa  10440
ttagccaggc gcggtggtgg gcgcttgtaa tcccagctac ttgggaggct gagacaagag  10500
aatcgcttga acccaggagg cggaggttgc agtgagccaa gatcgtgcca ttgcactcca  10560
acctgggcaa cagagtgaga ctccgtctca aataaaaaaa aacaaaaaat gagaagggct  10620
tgagaagtca ttcattcatg cactctcctt cttcatgtgg tcactctctc aagctgtcat  10680
tatactgaag aagaaataaa cttacacaat tcacaggtgc ttagcaacac tgctgggacc  10740
atgcccagcc attcagcctc ccagatggat gcttcggggt ctcgcaggtc ctctctccaa  10800
aggggacttt cttaatatct catgtttttt cctccttgca gttggaagaa taagacactt  10860
ttcctttttc tttttattca gtaacatttg tctactgaag cacacccaaa cagggacacc  10920
aaccagaata acgaagctcg ataaagtggt gtctggattt tcactgaaat cctgtgcact  10980
ttctaatctg ggtaattatc gacttcttga tgatgtaatt caaccattaa atatgctgat  11040
gattacagta gatctcactc aggataccag cttatgctca cgatgaaacg gacccaaaga  11100
tctttacctt cttcatgtga tagatttcat catgtcctat acagttagat cctctattta  11160
aatttccagt ttaaaataat catgccattt tcttctaaat aaaaaaaaat taaaagatct  11220
tgggatacac ttaaattttt taatatggaa tttacacata ctgtgaccgg aattttcctg  11280
atagctggtg aattgagtcc ctgacatagt tcttccgtcg cgcagcttgt attagggaca  11340
ttttccctaa tacggtgttt gcagacagca acatcgacag tgtcatggct cccgatgctt  11400
ttgtctgtgg ccgaatctgc actcatcatc ccggttgctt gtttttttacc ttcttttccc  11460
aggaatggcc caaagaatct caaaggtaag gagttaacaa gtaaggataa tttgttatct  11520
tctaaaaata gctgatcaaa atccatcatt aaaaattcca agtaactaaa aatttactct  11580
aaatgtcagt ataggataaa agttgcaaag aatttctagc cctctccct ttctattccc  11640
cacctactta ccacaaaccc aacattaccg aggactcttt tttttttttt tttttttttg  11700
agatggagtc tcgctctgct gcccaggctg gagtgcggtg gcatgatttc agctcactgc  11760
aaccttcgcc tcccaggtcc aagcgattct cctgcctcag cctcctgagt agctgggact  11820
acaggcatgg gacaccacgc ccagtaattt tttttgtatt tttagtagag atggggtttc  11880
accatgttgg ccaggctggt ctcaaactcc tgacttcagg tgatccacct gcctcggcct  11940
cccaaagtgc tgagattaca gggttgggcc accgtgcccg gccagtaaat tttaaaataa  12000
atataaatat tacttcacct aaataaattt taggtacagg tacagttgtg ttacatggat  12060
atactgtgta gtggtgaagt ctgggctttc agtgtagcca aatagtatac attattccca  12120
ttagataatt tctcctgcct caccctcctc tatcctccca actctctgag tctccaatag  12180
ctttcattcc actgtctctg tgcctgtgta cactttattt agctcccact taaaagtgag  12240
aatctacaat atttgacttt ctgtttctga gttgtttcac ttgagataat agcctccagt  12300
tctatccatg ttgctgcaaa agatatgatt ttatgatttt tttatggcta agtaacattc  12360
tatagtatat tctatacacc acattttctt tatccattca tttgctgata gactcttagg  12420
ttgatccata tctttgttat tgtgaatagt gctgcagtaa acatgtgagt gtaggtatct  12480
ttgtgacatg attttttttt ctttcttttc ctttggctat gtacccagta gtgggattgc  12540
tggaggtctc caccttggca aaggggcagt tgtctagttc taaatgaaat gaagagattc  12600
catttccatt tcatgacaac taaaagacaa ttcagtccaa tgctttgttt aaaataattg  12660
```

```
aaccaggaac agaaagagct gaaaatgtca gtgaaatgtc aaacccaaag tggagagaga  12720
gagagaggtg gaaatgaatg tctccatcaa gtgggttagg gtggtggtgg agggaggttt  12780
gagaattgag tccctgtttc cttaccaatg gaaattaaca taggacatca gaaacagcat  12840
ggaaaatttc tttgattatc aaaagtacac tagctaaggt tgctgtccct cttttattta  12900
tttatttatt tgagacaggg tcttgctctg tcactcagat ttggttgcac tgggtgtgat  12960
ctcagcccac tgcagcctcc acttcctagg ctcaagcaat ccacccgtct catcctccca  13020
agttgctggg accacaggtg tgcaccacca cccccagcta atgtttgttt ttttgtagag  13080
acagagtttc gccatgttgg ccaggctggt ctagaactcc tggcctcaag caatccacct  13140
gccttggtct cccacagtgc agggattaca agcctgagcc actatgccca gcttgctatt  13200
cctcattgac aacattcact taaacaagca aacaaatatc cgtaaaatta agtcagcttt  13260
aaaacctggc ttgtatatat ctctgaattg gaactctcag agccctcagc acttgcctga  13320
ttggcctcct gttgatgaaa agttgtcctc cagacaactc agccaaggga ggccctgtgt  13380
gccttgccta tcacatgagc ctcactttcc actgagtgag gctgtcattt cagaagcacc  13440
gggtctgtca catgaaaata tatctgttac catcacttac taaacaaatt tagtagaatt  13500
tgtttggtgc ttattatgta tcaggcattg ttctgaaggc tggggatacc atttagtgaa  13560
ctaaatcgac aaaaactttg cctattggac cagagtggag atgagagaga agtgaccaga  13620
tcgatctgtg ttatcagcag acagccaata agatttgctg ataggttgga ccacggattg  13680
tgaaggagtc agtgatagca ccaagacttt tggcccaagg aactggaaag atggaaatgt  13740
caatgacaga atgtggagga tttcgcaagc agcagagtgt aggagaagca atgcccttgg  13800
ctcatctagg gcaaagggtt gaattggcaa ctggaaatag aagtcaaatt cagaagagag  13860
gtttatgtgg acatctgtgt ttaggtgtca ccaatataca gctgatactt tttaaaaatc  13920
tagtgaaatt atcaaagggt taaatgcaga gagggaagaa agtaggtcca aagatcaagc  13980
cttgggacat tggaagttta gaaataagaa agatgtcatt gtcacttgta attttgtgct  14040
agtcactgct ctttttcttt gtcttattac cttactgacc aattcctaga ataggaataa  14100
cacatttgat ctttaataca gtatgtgata ggaacatggc ttctataagc ccaaacttgg  14160
caatttaaat ttaaatttat taaaattaaa taaaactggc tgggtgcagt ggctcacgcc  14220
tgtaatccca gcactttggg aggccgaggc ggtgaatcac gaggtcagga gtacgagacc  14280
atcctggcca acatggtgaa accccgtctc tactaaaaat acaaaagtta gccaggtgtg  14340
gtggcatgtg cctgtaatcc cagctactca agaggctgag gcaggagaat cacttgaacc  14400
cgggaggcgg aggttgcagt gagccaagat cgcgacactg cactccagcc tgggtgacaa  14460
gagaaagact atgtctcaaa aaaaaaaaaa attttaaata aaactaaaaa ttcaccttcc  14520
cagctgtgtt agccacattt caagtgccca atagccacat gtagttggca gttactgtat  14580
tggatggcac aggcatagaa tatttccatc actgcagaaa gatctatgga cagtcttgct  14640
ctagactgtg attttgtcta cttaggaaaa gtcactcttt tccaggaaga tgcttccagg  14700
gtgtggagta aacgacggac ttcacccatc tccttataaa cctattgcaa ccctggatag  14760
gaggtttcta ggtagcatga agactcttga atctttaaga taggctggga gtgttgaaag  14820
gaaggaaatg aaaagggaag atactaggaa gactgacaat agagcaagct cagaaaattt  14880
ttatggaggt gatttagtta gaaaatttgt ctgcaaccta agggccatgg agtgtgactc  14940
catggtttat gggtgtaact ccgtggttta tgaagagtac tttcaaaata ggaaaatctt  15000
cacaactaag tgctagcatg agctgacttt actttctcta ggtgctgtaa aaatgttttt  15060
```

```
atgtgtttga tatgatatat ttctacttcc cttttgtttt tgttagaaat ctttgtctcc  15120
ttaaaacatc tgagagtgga ttgcccagta cacgcattaa aaagagcaaa gctctttctg  15180
gtttcagtct acaaagctgc aggcacagca tcccaggtaa actgagagtt ctgcattctg  15240
gctgagagtg accagccccg aggaggctga tacatgctga gggagggtct cactctgaca  15300
tgtggtctgc tgtctagtgt tctgccattc ttcattttac catgacactg atttcttggg  15360
agaagaactg gatattgttg ctgcaaaaag tcacgaggcc tgccagaaac tgtgcaccaa  15420
tgccgtccgc tgccagtttt ttacctatac cccagcccaa gcatcctgca acgaagggaa  15480
gtaagccata tgaagggtta tgcagacacc cttgtcccgt ctgcctgtga ggtgcattat  15540
gtttataccg ttttgtttcc aactgcaggg gcaagtgtta cttaaagctt tcttcaaacg  15600
gatctccaac taaaatactt cacgggagag gaggcatctc tggatacaca ttaaggttgt  15660
gtaaaatgga taatggtgag tataatgtca cttgaaaaaa tatagctgaa ggaattattc  15720
catgcttcat acatcacaat caagactgtc agttatagcc acagaaggga gaacattcag  15780
gaaataacaa attttgcaat tttctattat tttcactcct gtcactcaag ctgaccatgt  15840
tttaaaggta aatattgagg cttgactaaa ctgtacattg cctagtatta actaaatata  15900
tgctttaatt tgacacattt atacacctgg catttctgtt ttctttcttt cttttttttt  15960
tttttttttt tgagacacag tctcactctg ttgcccaggc tggagtgcag tgatgtggtc  16020
agtgttcact gcagcctctg gcttgaactc ctggactcga acaatcctcc caccttagct  16080
ccctgagtag ctggggctac aggcgtgcac cacaacactc ggctaatttg ttgtagagat  16140
gggatcttgc catgttgccc aggctggtct tgaactcctg ggctcaagca atcctcccgc  16200
tttggcctcc caaagttctg ggattacagg cttcagccac tgcacccagc cacaactggc  16260
atttcctaat gagacccaga ctctgccaac actcctgtta tcaaggccag taatctttcc  16320
tattatcctt tgtaagggaa ttatcgatca gcactttggt tagtcaaatt actaattttc  16380
ttccaaaaat tgtgtatcta ttcaagaaat actggagcac ctccttttta gggtctttat  16440
tcagattcca tgcagggttc tggagactta gggattggca aaggttaagg taaaacttta  16500
ctagtaacaa tgagtgtggt aggatggaaa taagtgttta gattacacga gacctgtaat  16560
aacataaaag ttacaataaa aatccaacca gcagtgtttc catcccagtg gccaatttct  16620
gagcatagtc acgagagatg ctttgtaggc aaacagaatt gttctaaggg acaaaatccc  16680
caacaggaaa gaacacacca caaacactcc tgcttaaatt accatagtaa cttaggatgg  16740
ctttactata tattgattta cataaagctg catgttctta tactgtttat tgccaaatgt  16800
ccaatattac aatacactat aaggtgcaac tgagatttaa tgaataaaat ggaagtaaca  16860
atcctgcctc gtgatagttt tagaagcaca aaaacattct gtgtcagatt atctgctgta  16920
ccgagaaggc gaatcaatcc ttaatttctg agaacttgtt ttgtagaaca taaagacgtt  16980
atattgcctc caacactggt atcctaacta acagactatg ccttcctaga gcttagaggc  17040
gctccgatga aaatctctgg atggctcaag acttcttaaa aagcaagtca attacgtcgt  17100
atctcataca ttctgttttc ctcacaataa atttccctaa gacaagaagg agcattcggc  17160
accattctgt tgtctttctt ctacttctaa gcgttagaag ggacacttag caaatgttgc  17220
tgttaagtaa tgttgacatg gtttaataaa atgggaatga gcacgtatac ctcaatacat  17280
tgcagactgc attttccccc ttccttcttc attatggttt tctctgttgg atttatagac  17340
tctggcctgt agaagttaca gaatatgcca ggtatagatt gatagctaca ggagaaaatg  17400
```

```
taagataaag gaaaataaag tcttacgtct tttcagtgca actttggagg gagtgaatta  17460
gataactagg tttttactgc gctgtatttg atgaaataac cccctaatgt gaaagggaat  17520
agctgcgtga gatatttatg gtgccttgtc tgtcactggt ctacaatgta acttaacttt  17580
ctgaagatag atagcagcac cattaaaata aacatttctt accacaaaat atgattctaa  17640
acacatattt tcagcatttc gtttaaactg agaaacagca taggatgaac ctcaaggcct  17700
ctcacctgga ccttgagtta tttctaaaat atcttagtta ctatttacct attaattttc  17760
ctaaaattta cctttatgac gcttcccacc ttgcagaaat tccagaatag atggccctcc  17820
aaaatgaatg ttcacccttc cggctctaaa atgagagcct ctgttcaggc ttccgaagtc  17880
acatcgtgct cgttctcacc tcagttgctg ttagctgctg tttccttccg aactccttct  17940
ctcatcctct cctcctattt gaaatctgcc ccagaattat acactcattt tcctaccaag  18000
gaaaaaaagg cctagaaagg ttgttttaca cccacaaaac tagtgaatgg accttctagg  18060
acccggcttc tcatcagtga ttcttctgtt aacttagact cctcccttag ctcaggacgc  18120
ggagccttct gagcacctga gcctggttat tctaaatgtg atctgggcac agcacattga  18180
catcacctgg gagcttgtta gaaagaattt caggacccac acagatgtta ctgagtcaga  18240
atctgcattt tgaaagctac acaggcaacc cacaggcaca taaattttga gtcgcatagg  18300
tgtgtgcgtg tgtgtgcgca tgtatgtgtg cgtgtgtttg tgtgcacgtg tgtgtgtgtg  18360
tgtctagaat actgctgtct acgaacaccc tattcccatc catctgtgtt ccatggctcc  18420
aaccgggagg gtgggttctt gtgtcgggca tccagtaagt agaaatagag ggcactgtcc  18480
tgtctaggca gccccaagag aaaagaaaca gagggatgag cctgagtcaa agtccctgaa  18540
aagtaccaag gaccccagag aatcccaaac tgtcaacaag gccaaaggtc agaggaagtt  18600
catagcagat cagtcttact ttggacgtgg gtggagcagg agtgactggg atcatggtca  18660
gcagagtcac tgggacaggg caggaactgg acaatggctg cagcctgcgg gcaaggtgct  18720
tgccttttct ttctaagagc agttctcaaa cgccagcagg gctggttcaa acacagatgg  18780
ctgagcttcc aggctggagt ttctcattca ctggatctga ggttgggctg aagaatgtgc  18840
atttctaaca cgttcccagg tgacgctgtt ggtctggaga ctgcacttga caaccactgg  18900
tttaaaaaca ccattcacgt tatcatttga aggagggtaa gacagccttg tagtaccaca  18960
caaggagggc tacattctta ggggtgtgta attacaagat gacttagtca attccatttt  19020
tcatgtgcat gttttgcttt ggcagcttga ttataaagtc tctgtaactc agggtcatga  19080
taaactattg acttgaggaa aggttttctt cttgttcctg aaggagcata attactgatg  19140
gaaaggaaga tgtaggaagc tgctcatcac aatgcttctg ttgcagagtg taccaccaaa  19200
atcaagccca ggatcgttgg aggaactgcg tctgttcgtg gtgagtggcc gtggcaggtg  19260
accctgcaca caacctcacc cactcagaga cacctgtgtg gaggctccat cattggaaac  19320
cagtggatat taacagccgc tcactgtttc tatgggtcag taccacggct gtttttatta  19380
gttcatcttc ttcacacatt tataaaaaat attactagca tgttaggaaa taaatacttt  19440
aaccaattag attgtcttat ttgcaaaatt aattaattgc ttcagtggta aaaaacgcaa  19500
aaaggaagag ctcatggtct cccagcatca gaacaggtgc aggtacaagg ctgcttgact  19560
gcctgctatt ccgcttccca tttaaccgca ttcacatccc caagggcctt catgttattc  19620
cctgcaagag catacctccc tctgtgcctc gctctgtgca ctgtgcccgg aactaaactc  19680
acagaggatt taccattgtc tgaatcaaat ttctaatatg tgtgtgtgtg tgtgtgcgtg  19740
tgtgtttaaa tacagaaagt ggccaggtgt ggtggttcac gcctgtcatc tcagcacttt  19800
```

gggtggctga ggtgggagga ttgctcaatg ccaggagtct gaggtcagcc tgggcaacat 19860
agtgagacct cgtctctaaa aaatatttaa aaactagcct ggcatggtgt tttgtgtgcc 19920
tgtagcacca gctgctcaga agtctgaggt aggaggattg cttgagccca agagttcaag 19980
ggtgcagtga gttactacag tgccactgtg ctccagcctg agcaacagag caagacccta 20040
tctctaagta aataaataaa atacagaacg agttcggtat gcatcctcac attggattcc 20100
ttacttaggt cactttcagc gttggccaaa caaaaaggct ccagctgggg gtatatatat 20160
tccagggaag ttaagttggc caaactttcc gtttgctact tcagtatcct ccgagttgtt 20220
tccagacaca gttttgtgtg ctttttagtt ttggttttct tttttaatca atctgcagca 20280
cactcatgtt aaactcaaga acacatgtga ggccaagagt tcccgttacc tgtcacatat 20340
gggaatggag tagcagaaag cctagtttct gtcacagcta gttactggcg agattgagac 20400
tgagtccagc ggtcttcgtg tgtgtgtgtg cgtgtgtgtc tgtgcagtgt gcgtgtgtgt 20460
gcgtgtctgt gtgtgcgtgt gcgggtgtgt gcgtgtgtgt gtgttggagc acggagggag 20520
tgctcattca tttttgtgt ataatggatt ttctttatag ggtgaatatg tttttatcc 20580 cgaaaaatct taggataaaa tcactttttt ctacctaaat gtccatcatt ggcagaaaat 20640
attagtaata attaaacagc cacacacttc acaatgtctg ggaattattt ttagtaaagg 20700
aaatttcttt ccctctgttg tttgctcctt agggtagagt cacctaagat tttgcgtgtc 20760
tacagtggca ttttaaatca atctgaaata aaagaggaca catctttctt tggggttcaa 20820
gaaataataa tccatgatca gtataaaatg gcagaaagcg ggtatgatat tgccttgttg 20880
aaactggaaa ccacagtgaa ttacacaggt acggagaatt ttatccggaa agttgtctcc 20940
aatggtgaac tggataaaat gtttaacact actagactta cggcctgacc ctgccaatct 21000
ctccatgcgt tatcatcatg aaagggagag ggcctggaat gctagtcatt cactctgcta 21060
aggctgacac actttcctgg ctattgaaac ttattttggg aatgtgggta aagagatacg 21120
ttttcctgag tcttcttcag gtgcatagaa tgacataatt tcataatact ttggaatagt 21180
aaagataatt tagtctaaag ataatttatt aaagataatt tagggatgaa ggattgaagg 21240
ttagaacaat taagcaactt gtgcaggatc aaagtgagtt ggatgaggag ttagcggtga 21300
gggtgaggct tgtctctctc tcgccctctc atcctggcac atgtgcgata tcgtgctgaa 21360
cctgagggag gaaaatacac gacaacaagg caaaaaatga atatagtaaa caaagaaaac 21420
acagataatg tacagtggaa gaagagtctc ttctggaaaa gaggatatat tttgcgtctc 21480
atatttaaac cacgattttt taaatttaga ttctcaacga cccatatgcc tgccttccaa 21540
aggagataga aatgtaatat acactgattg ctgggtgact ggatgggggt acagaaaact 21600
aagaggtaaa aatgatgttg ttatatgtgc tccatcctag aaatgaagag cggaaccttt 21660
tctgccctgt caagtcatgt agctgaagca caactcgagt cacactactc agttgcagga 21720
agcggattaa taaagatgga gaggcaaaaa tcacccaagt gaggctggtg cctcatatgt 21780
ttgattggaa attttaaatg tgactaaatc tctttaaaga ctaattatat ttaatgaagt 21840
ttaatgtgaa gcctagcact tttcagtaaa tgttctagcc tgctatccaa ttactttctt 21900
gggaagtcat tccagttaga gtcataatta atttttgaac ttaattaaca ttaacaaaat 21960
ggtacacgca atagtgggaa taatgtcttc ttcatacttg taattataaa aggtctgtga 22020
agtaaatcta acatttttc cttctagatt tttatataga catgagtttt gtgttgttgt 22080
tgttttgaga tggactctcg ctctgtcgcc caggctggag tgcagtggca cgatctcggc 22140

```
tcactgttac ctccacctcc cgggttcaag tgattctcct gcctcagcct cccgagtagc  22200
tgggattata ggtacccaac caccacccca agctaatttt ttgtattttt agtagagacg  22260
gggtttcatc atgttagcca ggatggtctc aatctcctga cctcgtgatc cacctgcctc  22320
ggccttccaa agtgctggaa ttacaggcgt gagcccccac acccgtccat gatttttatt  22380
ttaaatatat gtggcccagc accactggtg gctcacgcct gtaatcccag cactttggga  22440
ggccaagatg ggtggatcac ttgaggtcag gagttcaaga ctggcctggc caacatggtg  22500
aaaccctgtc tctactaaaa atacaaaaat tagctgggca tggtggtgtg tgcctgtaat  22560
cccagctact cgggaggctg aggcaagata atcgcttgaa cttgggaggt ggaggtagca  22620
gtgagctgag attgcaccac tgcactccag cctgggcgac agaaagagac tccgtctcaa  22680
ttaaaaatat atatatatat atatttatat gtatgcatat atgtttatgt gtattgtgta  22740
tggttattct acaaacgaac caaaaaaatt tttttcagac aaaatacaaa atactctcca  22800
gaaagccaag atacccttag tgaccaacga agagtgccag aagagataca gaggacataa  22860
aataacccat aagatgatct gtgccggcta cagggaagga gggaaggacg cttgcaaggt  22920
aacagagtgt tcttagccaa tggaatatat gcaaattgga atgcttaatg cgttggggtt  22980
tttttgtttg ttttgttttt tttgtttgtt ttttttttgag acagagtctc gctctgttgc  23040
ccaggctgga gtgcagtggc tcgatctcag ctcactgcaa gctctgcctc ccaggttcac  23100
gccattctcc tgcctcagcc tcccaaatag ctgggactac aggcgccagc taccaagccc  23160
agctagcgtc tttttttttt ttagttttag tagagacggg gtttcaccat gttggccagg  23220
atggtctcga tctcctgacc tcatgatctg cctgcctggg cctcccaaag tgctgggatt  23280
acaggcgtga gccaccgcgc cgggccgctt aatgcatttt aaaaagcagt cttctgccaa  23340
tgagcaggga acacagtgta tttgtttgac ttagactgaa atcaaaagca aggagattga  23400
ctggatgaac gcaagcaccc aggttctctg cagtatatta aggggccaag acaacatttt  23460
aggcaaaatc agcctgagca agatgtgctg aagatgggaa gcgtctgagt tgatctgtgc  23520
accttttctt gtctcccctc gttctaggga gattcgggag gccctctgtc ctgcaaacac  23580
aatgaggtct ggcatctggt aggcatcacg agctggggcg aaggctgtgc tcaaagggag  23640
cggccaggtg tttacaccaa cgtggtcgag tacgtggact ggattctgga gaaaactcaa  23700
gcagtgtgaa tgggttccca ggggccattg gagtccctga aggacccagg atttgctggg  23760
agagggtgtt gagttcactg tgccagcatg cttcctccac agtaacacgc tgaaggggct  23820
tggtgtttgt aagaaaatgc tagaagaaaa caaactgtca caagttgtta tgtccaaaac  23880
tcccgttcta tgatcgttgt agtttgtttg agcattcagt ctctttgttt ttgatcacgc  23940
ttctatggag tccaagaatt accataaggc aatatttctg aagattacta tataggcaga  24000
tatagcagaa aataaccaag tagtggcagt ggggatcagg cagaagaact ggtaaaagaa  24060
gccaccataa atagatttgt tcgatgaaag atgaaaactg gaagaaagga gaacaaagac  24120
agtcttcacc attttgcagg aatctacact ctgcctatgt gaacacattt cttttgtaaa  24180
gaaagaaatt gattgcattt aatggcagat tttcagaata gtcaggaatt cttgtcattt  24240
ccattttaaa atatatatta aaaaaaatca gttcgagtag acacgagcta agagtgaatg  24300
tgaagataac agaatttctg tgtggaagag gattacaagc agcaatttac ctggaagtga  24360
taccttaggg gcaatcttga agatacactt tcctgaaaaa tgatttgtga tggattgtat  24420
atttatttaa aatatcttgg gaggggaggc tgatggagat agggagcatg ctcaaacctc  24480
cctaagacaa gctgctgctg tgactatggg ctcccaaaga gctagatcgt atatttattt  24540
```

gacaaaaatc accatagact gcatccatac tacagagaaa aaacaattag ggcgcaaatg 24600
gatagttaca gtaaagtctt cagcaagcag ctgcctgtat tctaagcact gggattttct 24660
gtttcgtgca aatatttatc tcattattgt tgtgatctag ttcaataacc tagaatttga 24720
attgtcacca catagctttc aatctgtgcc aacaactata caattcatca agtgtgattt 24780 ttttttttt tttttgagat gaagtctcac cctgttgccc aagctggagt gcagtggtgt 24840
gatctcggct cactgtaaac tctacctcct ggattcaagc gattgtcctg cctcagtctc 24900
ccaagtagct gagattacag gcacatgcca ccatgcccgg ctaatttttg tatttttagt 24960
agagacgggg tttcactatg ttggccaggc tggtcttgaa ctcctgacct cgtgatctgc 25020
ccacctcggc ctctcaaagt gctgggatta caggtgtgag tcactgcgtc tggccatgga 25080
aaatatttat tgagcacaat tatgtgagag catcatgctg agctttgaag atacagtggt 25140
gagcaaacat atatcctggc ttcatgaaga ttatactcta gttaacatga gcaacaaaat 25200
aaaataatca cacaaaatat ataggttcaa gctgaaatga gtggctgcac cagattctat 25260
gagataagaa aggaagaagg acatttttca ccaagttcaa agactgggat acaaaggaat 25320
ttgtcctgac aaaggcaaaa caaaaacaac aacaaacaaa aaacccaaaa gagcaaaatg 25380
acagtagaac ataacggggc cagatcaaaa atgctgacag gttcccaaaa gaataaaatg 25440
acggtaggac atgacggggc cagatccaaa atgctgacag gttcaaacaa aattggaatt 25500
gaaaatcaga gtgcgttcaa gagtatcaaa caatactatc ttgttacttg cttattacct 25560
tagtagactg gaagcaacac ttcacacaaa aaaagggttt ggatgtaatt tcggataaga 25620
agagatgttt ctgtaaagtc tttcctgaga agcatattat ttgagaaaaa cacatatttc 25680
tgtttttagt atttcacttt gtataatgtc ttaatttttg aagagctggt atattcctat 25740
gattcattaa tgaaagttct ataagatata aaatatacaa tgaggagatc tcctcttctg 25800
taccagaaga gtgcacattc tacacactgc gtagcacctt tctcacttac gttctgtctg 25860
ggcacacttc tgattgacac gcagagggct ctctctgtct ggggatattt ctgatgggta 25920
ccgagagagc ttcctctatc ttgggttatt tctgatgcgt agagaagggc tgcctctgtc 25980
cattatggaa ggctggtgtt c 26001

<210> SEQ ID NO 2
<211> LENGTH: 3278
<212> TYPE: DNA
<213> ORGANISM: Homo sapien

<400> SEQUENCE: 2
aggcacacag gcaaaatcaa gttctacatc tgtccctgtg tatgtcactt gtttgaatac 60
gaaataaaat taaaaaaata aattcagtgt attgagaaag caagcaattc tctcaaggta 120
tatttctgac atactaagat tttaacgact ttcacaaata tgctgtactg agagagaatg 180
ttacataaca ttgagaacta gtacaagtaa atattaaagt gaagtgacca tttcctacac 240
aagctcattc agaggaggat gaagaccatt ttggaggaag aaaagcaccc ttattaagaa 300
ttgcagcaag taagccaaca aggtcttttc aggatgattt tcttatatca agtggtacat 360
ttcattttat ttacttcagt ttctggtgaa tgtgtgactc agttgttgaa ggacacctgc 420
tttgaaggag gggacattac tacggtcttc acaccaagcg ccaagtactg ccaggtagtc 480
tgcacttacc acccaagatg tttactcttc actttcacgg cggaatcacc atctgaggat 540
cccacccgat ggtttacttg tgtcctgaaa gacagtgtta cagaaacact gccaagagtg 600

```
aataggacag cagcgatttc tgggtattct ttcaagcaat gctcacacca aataagcgct    660
tgcaacaaag acatttatgt ggacctagac atgaagggca taaactataa cagctcagtt    720
gccaagagtg ctcaagaatg ccaagaaaga tgcacggatg acgtccactg ccactttttc    780
acgtacgcca caaggcagtt tcccagcctg gagcatcgta acatttgtct actgaagcac    840
acccaaacag ggacaccaac cagaataacg aagctcgata aagtggtgtc tggattttca    900
ctgaaatcct gtgcactttc taatctggct tgtattaggg acattttccc taatacggtg    960
tttgcagaca gcaacatcga cagtgtcatg gctcccgatg cttttgtctg tggccgaatc   1020
tgcactcatc atcccggttg cttgtttttt accttctttt cccaggaatg gcccaaagaa   1080
tctcaaagaa atctttgtct ccttaaaaca tctgagagtg gattgcccag tacacgcatt   1140
aaaaagagca aagctctttc tggtttcagt ctacaaagct gcaggcacag catcccagtg   1200
ttctgccatt cttcatttta ccatgacact gatttcttgg gagaagaact ggatattgtt   1260
gctgcaaaaa gtcacgaggc ctgccagaaa ctgtgcacca atgccgtccg ctgccagttt   1320
tttacctata ccccagccca agcatcctgc aacgaaggga agggcaagtg ttacttaaag   1380
ctttcttcaa acggatctcc aactaaaata cttcacggga gaggaggcat ctctggatac   1440
acattaaggt tgtgtaaaat ggataatgag tgtaccacca aaatcaagcc caggatcgtt   1500
ggaggaactg cgtctgttcg tggtgagtgg ccgtggcagg tgaccctgca cacaacctca   1560
cccactcaga gacacctgtg tggaggctcc atcattggaa accagtggat attaacagcc   1620
gctcactgtt tctatggggt agagtcacct aagattttgc gtgtctacag tggcatttta   1680
aatcaatctg aaataaaaga ggacacatct ttctttgggg ttcaagaaat aataatccat   1740
gatcagtata aaatggcaga aagcgggtat gatattgcct tgttgaaact ggaaaccaca   1800
gtgaattaca cagattctca acgacccata tgcctgcctt ccaaaggaga tagaaatgta   1860
atatacactg attgctgggt gactggatgg gggtacagaa aactaagaga caaaatacaa   1920
aatactctcc agaaagccaa gataccctta gtgaccaacg aagagtgcca gaagagatac   1980
agaggacata aaataaccca taagatgatc tgtgccggct acagggaagg agggaaggac   2040
gcttgcaagg gagattcggg aggccctctg tcctgcaaac acaatgaggt ctggcatctg   2100
gtaggcatca cgagctgggg cgaaggctgt gctcaaaggg agcggccagg tgtttacacc   2160
aacgtggtcg agtacgtgga ctggattctg gagaaaactc aagcagtgtg aatgggttcc   2220
caggggccat tggagtccct gaaggaccca ggatttgctg ggagagggtg ttgagttcac   2280
tgtgccagca tgcttcctcc acagtaacac gctgaagggg cttggtgttt gtaagaaaat   2340
gctagaagaa aacaaactgt cacaagttgt tatgtccaaa actcccgttc tatgatcgtt   2400
gtagtttgtt tgagcattca gtctctttgt ttttgatcac gcttctatgg agtccaagaa   2460
ttaccataag gcaatatttc tgaagattac tatataggca gatatagcag aaaataacca   2520
agtagtggca gtggggatca ggcagaagaa ctggtaaaag aagccaccat aaatagattt   2580
gttcgatgaa agatgaaaac tggaagaaag gagaacaaag acagtcttca ccattttgca   2640
ggaatctaca ctctgcctat gtgaacacat ttcttttgta aagaaagaaa ttgattgcat   2700
ttaatggcag attttcagaa tagtcaggaa ttcttgtcat ttccatttta aaatatatat   2760
taaaaaaaat cagttcgagt agacacgagc taagagtgaa tgtgaagata acagaatttc   2820
tgtgtggaag aggattacaa gcagcaattt acctggaagt gataccttag ggcaatctt    2880
gaagatacac tttcctgaaa aatgatttgt gatggattgt atatttattt aaaatatctt   2940
gggaggggag gctgatggag atagggagca tgctcaaacc tccctaagac aagctgctgc   3000
```

```
tgtgactatg ggctcccaaa gagctagatc gtatatttat ttgacaaaaa tcaccataga   3060

ctgcatccat actacagaga aaaaacaatt agggcgcaaa tggatagtta cagtaaagtc   3120

ttcagcaagc agctgcctgt attctaagca ctgggatttt ctgtttcgtg caaatattta   3180

tctcattatt gttgtgatct agttcaataa cctagaattt gaattgtcac cacatagctt   3240

tcaatctgtg ccaacaacta tacaattcat caagtgtg                            3278


<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3

acggcattgg tgcacagttt                                                  20


<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4

acggtgtttg cagacagcaa                                                  20


<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5

tgcagattcg gccacaga                                                    18


<210> SEQ ID NO 6
<211> LENGTH: 26
<212> TYPE: DNA
<213> ORGANISM: Artificial sequence
<220> FEATURE:
<223> OTHER INFORMATION: Probe

<400> SEQUENCE: 6

acagtgtcat ggctcccgat gctttt                                           26


<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7

cagcctggag catcgtaaca                                                  20


<210> SEQ ID NO 8
<211> LENGTH: 25
<212> TYPE: DNA
<213> ORGANISM: Artificial sequence
<220> FEATURE:
<223> OTHER INFORMATION: Primer
```

<400> SEQUENCE: 8
tttatcgagc ttcgttattc tggtt 25

<210> SEQ ID NO 9
<211> LENGTH: 29
<212> TYPE: DNA
<213> ORGANISM: Artificial sequence
<220> FEATURE:
<223> OTHER INFORMATION: Probe

<400> SEQUENCE: 9
ttgtctactg aagcacaccc aaacaggga 29

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gccaggtagt ctgcacttac 20

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gtcctattca ctcttggcag t 21

<210> SEQ ID NO 12
<211> LENGTH: 25
<212> TYPE: DNA
<213> ORGANISM: Artificial sequence
<220> FEATURE:
<223> OTHER INFORMATION: Probe

<400> SEQUENCE: 12
ccacccgatg gtttacttgt gtcct 25